(12) United States Patent
Lewis et al.

(10) Patent No.: US 9,259,422 B2
(45) Date of Patent: Feb. 16, 2016

(54) ORVINOL AND THEVINOL DERIVATIVES USEFUL IN THE TREATMENT OF DEPRESSION

(71) Applicant: The University of Bath, Bath and North East Somerset (GB)

(72) Inventors: John Lewis, Winscombe (GB); Stephen Husbands, Bath (GB)

(73) Assignee: The University of Bath, Bath and North East Somerset (GB)

(*) Notice: Subject to any disclaimer, the term of this patent is extended or adjusted under 35 U.S.C. 154(b) by 0 days.

(21) Appl. No.: 14/674,578

(22) Filed: Mar. 31, 2015

(65) Prior Publication Data
US 2015/0202200 A1    Jul. 23, 2015

Related U.S. Application Data

(63) Continuation of application No. 14/131,361, filed as application No. PCT/GB2012/051575 on Jul. 5, 2012, now Pat. No. 9,051,334.

(30) Foreign Application Priority Data

Jul. 8, 2011 (GB) .................................. 1111775.1

(51) Int. Cl.
*A61K 31/485* (2006.01)
*C07D 489/12* (2006.01)
*C07D 491/08* (2006.01)

(52) U.S. Cl.
CPC ............ *A61K 31/485* (2013.01); *C07D 489/12* (2013.01); *C07D 491/08* (2013.01)

(58) Field of Classification Search
USPC .......................................................... 514/279
See application file for complete search history.

(56) References Cited

U.S. PATENT DOCUMENTS 3,433,791 A    3/1969 Bentley

FOREIGN PATENT DOCUMENTS

GB            1136214        12/1968
WO     WO 2004/078178 A1     9/2004
WO     PCT/GB2012/051575     8/2012

OTHER PUBLICATIONS

Marton, J. et al.: New nepenthone and Thevinone derivatives. Bioorg. & Med. Chem., vol. 5, pp. 369-382, 1997.*
Rothman, R. et al.: An open-label study of a functional opioid kappa antagonist in the treatment of opioid dependence. J. of Substance Abuse Treatment, vol. 18, pp. 277-281, 2000.*
Walker, B. et al.: Pharmacological evidence for a motivational role of kappa-opioid systems in ethanol dependence. Neuropsychopharmacology, vol. 33, pp. 643-652, 2008.*
Barton, J.W. et al., "Diels-Alder Reactions of Thebaines with Cycloalkenones; Lithium Tetrafluoroborate as a Novel Diels-Alder Catalyst," *Tetrahedron Letts.* 34:6777-6778, Pergamon Press Ltd. (1993).
Bentley, K.W. and Ball, J.C., "Acid-Catalyzed Rearrangements in the Nepenthone Series," *J. Org. Chem.* 23:1720-1725, American Chemical Society (1958).
Bentley, K.W. et al., "Benzflavothebaone," *J. Org. Chem.* 23:941-946, American Chemical Society (1958).
Coop, A. et al., "Methylation of the Enolates of Thevinone and some Analogues," *Tetrahedron* 51:9681-9698, Elsevier Science Ltd. (1995).
Coop, A. et al., "Ring Constrained Analogues of the Thevinones; Diels-Alder Reactions of Thebaines with 1-Indenone and Methylene Cycloalkanones," *Tetrahedron Letts.* 36:1689-1692, Elsevier Science Ltd. (1995).
Husbands, S.M., "Discovery of New Treatments for Drug Abuse," [Grant application 2R01DA007315-17 to the U.S Department of Health and Human Services, National Institutes of Health, National Institute on Drug Abuse], Award Notice Date: Sep. 12, 2009.
Lewis, J.W. et al., "Novel Analgesics and Molecular Rearrangements in the Morphine—Thebaine Group. Part XIX. Further Diels—Alder Adducts of Thebaine," *J. Chem. Soc.* (C):1158-1161, The Chemical Society of London (1971).
Lewis, J.W. et al., "Novel Analgesics and Molecular Rearrangements in the Morpine—Thebaine Group. Part XX. Reaction of 7β-Cyano-6,14-*endo*-etheno-7α-methyl-6,7,8,14-tetrahydrothebaine with Phenylmagnesium Bromide," *J. Chem. Soc.* (C):1161-1163, The Chemical Society of London (1971).
Lewis, J.W. et al., "Novel Analgesics and Molecular Rearrangements in the Morphine—Thebaine Group. Part XXII. Deamination of 7β-Aminomethyl-6,14-*endo*-etheno-7α-methyl-6,7,8,14-tetrahydrothebaine," *J. Chem. Soc.* (C):2298-2300, The Chemical Society of London (1971).
Maat, L. et al., "Chemistry of Opium Alkaloids. Part 44: Synthesis and Opioid Receptor Binding Profile of Substituted Ethenoisomorphinans and Ethenomorphinans," *Bioorg. Med. Chem.* 7:529-541, Elsevier Science Ltd. (1999).

(Continued)

*Primary Examiner* — Charanjit Aulakh
(74) *Attorney, Agent, or Firm* — Sterne, Kessler, Goldstein & Fox P.L.L.C.

(57) ABSTRACT

The invention provides method of treating depression comprising administering to a subject compounds having formula 2:

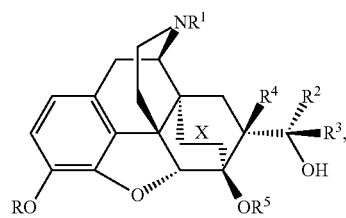

or a pharmaceutically acceptable salt or solvate thereof, wherein R, $R^1$, $R^2$, $R^3$, $R^4$, $R^5$, and X are us defined in the specification.

11 Claims, No Drawings

(56) References Cited

OTHER PUBLICATIONS

Morrison, R.T. and Wishman, M., "Mechanisms of Grignard Reactions. I. Addition to Acid Halides. Metallic Halides as Lewis Acids," *J. Am. Chem. Soc.* 76:1059-1061, American Chemical Society (1954).

Pindur, U. and Keilhofer, D., "New Studies and a Reinvestigation on [4 + 2] Cycloadditions of (−)-Thebaine: Asymmetrical Diels-Alder Reactions with a Conformationally Fixed Chiral Diene," *Liebigs Ann. Chem.*, 947-953, VCH Verlagsesellschaft mbH, Germany (1993).

Ridzwan, I.E. et al., "A Single Compound Alternative to a Buprenorphine/Naltrexone Combination to Prevent Relapse to Drug Addiction," poster presented at the 2011 Winter Meeting of the British Pharmacological Society (Dec. 13-15, 2011).

Carlezon, W.A., Jr. et al., "Kappa-opioid ligands in the study and treatment of mood disorders," *Pharmacol. Ther. 123*:334-343, Elsevier Inc. (2009).

Mague, S.D. et al., "Antidepressant-Like Effects of κ-Opioid Receptor Antagonists and the Forced Swim Test in Rats," *J. Pharmacol. Exp. Ther. 305*:323-330, The American Society for Pharmacology and Experimental Therapeutics (2003).

McLaughlin, J.P. et al., "κ Opioid Receptor Antagonism and Prodynorphin Gene Disruption Block Stress-Induced Behavioral Responses," *J. Neurosci. 23*:5674-5683, Society for Neuroscience (2003).

Harrison, C. "Opioid receptor blocker shows promise in Phase II depression trial," *Nat. Rev. Drug Discov. 12*:415, Macmillan Publishers Limited (2013).

Alt, A., Clark, M., Woods, J.H., and Traynor, J.R. Brit J Pharmacol. 2002, 135, 217-225.

Auriacombe, M.; Fatseas, M.; Dubemet, J.; Daulouede, J.P.; Trignol, J. "French field experience with buprenorphine." Am. J. Addict, 2004, 13, Suppl 1, 817-28.

Beardsley, P.M., Howard, J.L., Shelton, K.L. & Carroll, F.I. "Differential effects of the novel kappa opioid receptor antagonist, JDTic, on reinstatement of cocaine-seeking induced by footshock stressors vs cocaine primes and its antidepressant-like effects in rats." Psychopharmacology (Berl.) 2005, 183, 118-126.

Bloms-Funke P, Gillen C, Schuettler AJ and Wnendt S. "Agonistic effects of the opioid buprenorphine on the nociceptin/OFQ receptor." Peptides 2000, 21,1141-1146.

Ciccocioppo R, Economidou D, Rimondini R, Sommer W, Massi M and Heilig M. "Buprenorphine Reduces Alcohol Drinking Through Activation of the Nociceptin/Orphanin FQ-NOP Receptor System." Bioi Psychiatry. 2007, 61, 4-12.

Comer, S.D.; Sullivan, M.A.; Yu, E.; Rothenberg, J.L.; Kleber, H.D.; Kampman, K.; Dackis, C.; O'Brien, C.P. Injectable, sustained release naltrexone for the treatment of opioid dependence: a randomized, placebo controlled trial. Archives of General Psychiatry, 2006, 63, 210-218.

Corkery, J.M.; Schifano, F.; Ghodse, A. H.; Oyefeso, A. The effects of methadone and its role in fatalities. Hum. Psychopharmacol., 2004, 19, 565-576.

Cowan A, Lewis JW and Macfarlane IR. Agonist and antagonist properties of buprenorphine, a new anti nociceptive agent. Br J Pharmacal. 1977b, 60, 537-545.

Cowan A.; Doxey J.C.; Harry E.J. The animal pharmacology of buprenorphine, an oripavine analgesic agent. Br J Pharmacal., 1977a, 60, 547-554.

Cowan, A. Update on the general pharmacology of buprenorphine. In 'Buprenorphine: Combating drug abuse with a unique opioid. Eds. Cowan and Lewis, Wiley-Liss, New York, 1995, 31-47.

Gerta Cami-Kobeci et al: "Structural Determinants of Opioid and NOP Receptor Activity in Derivatives of Buprenorphine". Journal of Medicinal Chemistry, vol. 54, No. 19, Oct. 13, 2011. pp. 6531-6537.

DAWN—Drug Abuse Warning Network, 2003: Area Profiles of Drug-Related Mortality, DAWN Series D-27,DHHS Publication No. (SMA) 05-4023, Rockville, MD, Mar. 2005.

Gerra, G., Fantoma, A. & Zaimovic, A. Naltrexone and buprenorphine combination in the treatment of opioid dependence. J. Psychopharmacol. 2006, 20, 806-814.

Gonzalez G, Oliveto A, Kosten TR. Combating opiate dependence: a comparison among the available pharmacological options. Expert Opinion on Pharmacotherapy, 2004, 5, 713-725.

Gorelick, D.A. Regarding "Buprenorphine reduces alcohol drinking through activation of the nociceptin/orphanin FQ-NOP receptor system". Biol. Psychiatry 2007, 62, 702.

Huang, P.; Kehner, G.B.; Cowan, A.; Liu-Chen, L.-Y. "Comparison of pharmacological activities of buprenorphine and norbuprenorphine; norbuprenorphine is a potent opioid agonist." J. Pharmacal. Exp. Ther., 2001, 297, 688-695.

Knoll, A.T.; Meloni, E.G.; Thomas, J.B.; Carroll, F.I.; Carlezon Jr, W.A. "Anxiolytic-like effects of kappa-opioid receptor anagonists in models of unlearned and learned fear in rats." J. Pharmacal. Exp. Ther., 2007, 323, 838-845.

Kosten, T.R., Kleber, H.D. & Morgan, C. "Treatment of cocaine abuse with buprenorphine." Biol. Psychiatry 1989, 26, 637-639.

Kotlinska, J., Wichmann, J., Legowska, A., Rolka, K. & Silberring, J. Orphanin FQ/nociceptin but not Ro 65-6570 inhibits the expression of cocaine-induced conditioned place preference. Behav. Pharmacal. 2002, 13, 229-235.

Kovacs, K.M.; Szakalll.; O'Brien D.; Wang R.; Vinod K.Y.; Saito M.; Simonin F.; Kieffer B.L.; Vadasz C.; Decreased oral self administration of alcohol in KOR knockout mice. Alcohol Clin. Exp. Res., 2005, 29, 730-738.

Lewis, J.W. Ring C-bridged derivatives of thebaine and oripavine. Adv. Biochem. Psychopharmacol., 1973, 8, 123-36.

Lewis, J.W.; Bentley, K.W.; Cowan, A. Narcotic analgesics and antagonists. Ann. Rev. Pharmacal., 1971, 11,241-270.

Lewis, J.W.; Husbands, S.M. The Orvinols and Related Opioids—High Affinity Ligands with Diverse Efficacy Profiles. Current Pharmaceutical Design, 2004, 10, 717-732.

Lobmaier, P.; Kornor, H.; Kunoe, N.; Bjomdal, A. Sustained-release naltrexone for opioid dependence (Cochrane review). The Cochrane Library, 2008, Issue 3, pp. 1-58.

Lutfy K, Eitan S, Bryant CD, Yang YC, Saliminejad N, Walwyn W, Kieffer BL, Takeshima H, Carroll FI, Maidment NT and Evans CJ. Buprenorphine-induced antinociception is mediated by mu-opioid receptors and compromised by concomitant activation of opioid receptor-like receptors. J Neurosci 2003, 23:10331-10337.

Mague, S.D.; Pliakas, A.M.; Todtenkopf, M.S.; Tomasiewicz, H.C.; Zhang, Y.; Stevens, W.C.; Jones, R.M.; Portoghese, P.S.; Carlezon, W.A. Antidepressant-like effects of kappa-opioid receptor antagonists in the forced swim test in rats. J. Pharmacal. Exp. Ther., 2003, 305, 323-330.

Marquez, P.; Nguyen, A.T.; Hamid, A.; Lutfy, K. The endogenous OFQ/N/ORL-1 receptor system regulates the rewarding effects of acute cocaine. Neuropharmacology, 2008, 54, 564-568.

Marton, J.; Simon, C.; Hosztafi, S.; Szabo, Z; Marki, A.; Borsodi, A.; Makleit, S. New nepenthone and thevinone derivatives. Bioorg. Med. Chem., 1997, 369-382.

McAleer, S.D.; Mills, R.J.; Polack, T.; Hussain, T.; Rolan, P.E.; Gibbs, A.D.; Mullins, F.G.P.; Hussein, Z. Pharmacokinetics of high dose buprenorphine following single administration of sublingual tablet formulations in opioid naive healthy male volunteers under a naltrexone block. Drug and Alcohol Dependence, 2003, 72, 75-83.

McCann, D.J. Potential of buprenorphine/naltrexone in treating polydrug addiction and co-occurring psychiatric disorders. Clinical Pharmacology & Therapeutics. 2008, 83, 627-630.

McLaughlin, J.P., Marton-Popovici M. & Chavkin C. Kappa opioid receptor antagonism and prodynorphin gene disruption block stress-induced behavioral responses. J. Neurosci. 2003, 23, 5674-5683.

Mello, N.K., Mendelson, J.H. Buprenorphine treatment of cocaine and heroin abuse. in 'Buprenorphine: Combatting drug abuse with a unique opioid.' eds Lewis and Cowan, New York, NY, US: Wiley-Liss, 1995, 241-287.

Mello, N.K., Mendelson, J.H., Bree, M.P. & Lukas, S.E. Buprenorphine suppresses cocaine self-administration by rhesus monkeys. Science 1989, 245, 859-862.

(56) References Cited

OTHER PUBLICATIONS

Minozzi, S.; Amato, L.; Vecchi, S.; Davoli, M.; Kirchmayer, U.; Verster, A. Oral naltrexone maintenance treatment for opioid dependence (Cochrane review). The Cochrane Library. 2006, Issue 1, pp. 1-27.

Montoya, 1.0.; Gorelick, D.A.; Preston, K.L.; Schroeder, J.R.; Umbricht, A.; Cheskin, L.J.; Lange, W.R.; Contoreggi, C.; Johnson, R.E.; Fudala, P.J. Randomized trial of buprenorphine for treatment of concurrent opiate and cocaine dependence. Clin. Pharmacal. Ther., 2004, 75, 34-48.

Bentley K. W. et al: "Novel analgesics and molecular rearrangements in the morphine-thebaine group. II. Alcohols derived from 6,14-endo-etheno- and 6,14-endo-ethanotetrahydrothebaine". Journal of the American Chemical Society Jun. 21, 1967, vol. 89, No. 13, Jun. 21, 1967, pp. 3273-3280.

Redila, V.A.; Chavkin, C. Stress-induced reinstatement of cocaine seeking is mediated by the kappa opioid system. Psychopharmacology, 2008, 200, 59-70.

Rothman, R.B. A review of the role of anti-opioid peptides in morphine tolerance and dependence. Synapse, 1992, 12, 129-138.

Rothman, R.B. Gorelick, D.A.; Heishman, S.J.; Eichmiller, P.R.; Hill, B.H.; Norbeck, J.; Liberto, J.G. I. An openlabel study of a functional opioid kappa antagonist in the treatment of opioid dependence. J. Subst. Abuse Treat. 2000, 18, 277-281.

Rothman, R.B.; Long, J.B.; Bykov, V.; Xu, H.; Jacobson, A.E.; Rice, K.C.; Holaday, J.W. Upregulation of the opioid receptor complex by the chronic administration of morphine: A biochemical marker related to the development of tolerance and dependence. Peptides, 1991, 12, 151-160.

Spagnolo, B.; Calo, G.; Polgar, W.E.; Jiang, F.; Olsen, C.M.; Berzatei-Gurske, 1.; Khroyan, T.V.; Husbands, S.M.; Lewis, J.W.; Toll, L.; Zaveri, N.T. Activities of mixed NOP and D-opioid receptor ligands. Br, J. Pharmacal., 2008, 153, 609-619.

Schottenfeld, R.S., Pakes, J., Ziedonis, D. & Kosten, T.R. Buprenorphine: doserelated effects on cocaine and opioid use in cocaine-abusing opioid-dependent humans. Biol. Psychiatry 1993, 34, 66-74.

Shoblock, J.R.; Wichmann, J.; Maidment, N.T. The effect of a systemically active ORL-1 agonist, Ro64-6198, on the acquisition, expression, extinction and reinstatement of morphine conditioned place preference. Neuropharmacology, 2005, 49, 439-446.

J. W. Lewis et al: "Novel analgesics and molecular rearrangements in the morphine?thebaine group. Part XXI. Alcohols derived from 7-methyl-epi-nepenthone". Journal of the Chemical Society C: Organic, Jan. 1, 1971. p. 2296.

Srisurapanont, M.; Jarusuraisin, N. Opioid antagonists for alcohol dependence (Cochrane review), The Cochrane Library, 2008, issue 3, pp. 1-92.

Traynor, J. R., and Nahorski, S. R. Modulation by mu-opioid agonists of guanosine-5'-0-(3-[35S]thio)triphosphate binding to membranes from human neuroblastoma SH-SY5Y cells. Mol. Pharmacal. 1995, 47, 848-854.

Walker, B.M.; Koob, G. F. Pharmacological evidence for a motivational role of kappa-opioid systems in ethanol dependence, Neuropsychopharmacology, 2008, 33, 643-652.

Wnendt S, Kruger T, Janocha E, Hildebrandt D and Englberger W. Agonistic effect of buprenorphine in a nociceptin/ OFQ receptor-triggered reporter gene assay. Mol Pharmacal 1999, 56, 334-338.

Zaveri N. Polgar WE, Olsen CM, Kelson AB, Grundt P, Lewis JW and Toll L. Characterization of opiates, neuroleptics, and synthetic analogs at ORL 1 and opioid receptors. Eur J Pharmacal 2001, 428, 29-36.

Zhao, R-J.; Woo, R-S.; Jeong, M-S.; Shin, B-S.; Kim, D-G.; Kim, K-W. Orphanin FQ/nociceptin blocks methamphetamine place preference in rats. Molecular Neuroscience, 2003, 14, 2383-2385.

Agabio R, Cortis G, Fadda F, Gessa GL, Lobina C, Reali R, Colombo G. "Circadian drinking pattern of Sardinian alcohol-preferring rats." Alcohol & Alcoholism 1996; 31: 385-8.

Colombo G. "Ethanol drinking behaviour in Sardinian alcohol-preferring rats." Alcohol & Alcoholism 1997; 32: 443-53.

Lobina C, Agabio R, Diaz G, Fa M, Fadda F, Gessa GL, Reali R, Colombo G. "Constant absolute ethanol intake by Sardinian alcohol preferring rats independent of ethanol concentrations." Alcohol & Alcoholism 1997; 32: 19-22.

Janos Marton et al: "Synthesis of New Nepenthone Derivatives", Liebigs Annalen, vol. 1996, No. 10, Oct. 1, 1996, pp. 1653-1656.

Liu Chun-He et al: "Synthesis, crystal structure of 7.alpha.-[(S)-1-hydroxy-1-(2-thienyl)ethyl]-6,14-endoethanotetrahydrothebaine", Journal of Chemical Research, Science Reviews Ltd, GB, No. 3, Jan. 1, 2005, pp. 169-170.

Cowan, A.; Friderichs, E.; Strasburger, W.; Raffa, R.B. Basic pharmacology of buprenorphine, in "Buprenorphine—the unique opioid analgesic" ed.s. Budd, K.; Raffa, R., Thieme, New York, 2005.

Negus, S.S.; Woods, J.H. Reinforcing effects, discriminative stimulus effects and physical dependence liability of buprenorphine, in "Buprenorphine—combating drug abuse with a unique opioid" ed.s. Cowan, A and Lewis, J.W. Wiley-Liss, New York, 1995, p. 71-101.

Shoblock, J.R. The pharmacology of Ro-64-6198, a systemically active, non peptide NOP receptor (opiate receptor-like 1, ORL-1) agonist with diverse preclinical therapeutic activity. CNS Drug Reviews, 2007, 13, 107-136.

* cited by examiner

ORVINOL AND THEVINOL DERIVATIVES USEFUL IN THE TREATMENT OF DEPRESSION

FEDERALLY SPONSOR RESEARCH STATEMENT

This invention was made with government support under DA007315 awarded by the National Institutes of Health. The government has certain rights in the invention.

TECHNICAL FIELD

This invention relates to orvinol and thevinol compounds useful for the treatment of drug and alcohol abuse. The compounds are especially useful for the treatment of opioid abuse, cocaine abuse, alcohol abuse and polydrug abuse, and are useful for the prevention of relapse in recovering addicts.

BACKGROUND

The compounds of the invention are structurally related to buprenorphine. But, unlike buprenorphine, the compounds are mu opioid receptor (MOPr) antagonists that do not also have significant MOPr agonist activity. They share buprenorphine's antagonism at kappa opioid receptors (KOPr) and may also have activity at the NOP/ORL-1 receptor.

Orvinols

The orvinols are a group of ring-C bridged epoxymorphinan compounds of general structure (1) which were originally synthesised by Bentley and co-workers and developed by Reckitt and Colman (Lewis et al. 1971). The most studied members of the series are the extremely potent opiate analgesic and animal immobilising agent etorphine (1a), the very potent opiate antagonist diprenorphine (1b) and the clinical analgesic and treatment for opiate abuse, buprenorphine (1c).

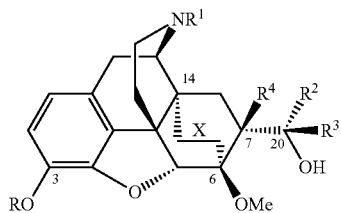

1a: R=H, R$^1$=R$^2$=Me, R$^3$=n-Pr, R$^4$=H
1b: R=H, R$^1$=cycloptopymethyl, R$^2$=R$^3$=Me, R$^4$=H
1c: R=H, R$^1$=cyclopropylmethyl, R$^2$=Me, R$^3$=t-Bu, R$^4$=H
1d: R=R$^2$=R$^3$=R$^4$=H, R$^1$=cyclopropylmethyl
1e: R=R$^2$=R$^4$H, R$^1$=cyclopropylmethyl, R$^3$=Me
1f: R=R$^3$=R$^4$=H, R$^1$=cyclopropylmethyl, R$^2$=Me The orvinols and derivatives of structure 1 are described in a series of UK Patents GB902659, GB925723, GB937214, GB969263 and GB1136214, which discuss their synthesis and potential therapeutic uses as analgesics, antitussives and, in some cases, antagonists of narcotic drugs. The patent applications do not describe compounds in which R4 is anything other than hydrogen. Further, the stereochemistry about C20 was not specified. The inventors have recognised that the stereochemistry about C20 is in fact of utmost importance and the diastereoisomers of structure 1 in which R2 and R3 are interchanged have very different pharmacological profiles.

In their publications, the inventors have described how the structure-activity relationships in the orvinols (1, R=H) and thevinols (1, R=Me) are conventional with respect to substituents on the basic nitrogen atom and at C3, the phenolic position (Lewis and Husbands, 2004), but that the effect of the nature of the substituents and the stereochemistry of C20 is of even greater significance (Lewis and Husbands, 2004). In particular, the inventors have found that there Is only a very limited range of structures which have a lack of opioid agonist activity and are therefore essentially opioid antagonists. Prior to the present invention the only compounds of structure 1 to have been shown to lack agonist activity at opioid receptors were the N-cyclopropylmethyl (N-CPM) primary and secondary alcohols (1d, 1e, 1f) (Lewis, 1973). Thus the discovery of novel orvinols with C20 aryl substituents that lack opioid agonist activity was both unexpected and desirable. Though compounds having structure 1 in which R2 is aryl and R4 is H are within the generic scope of GB969,263 and GB1,136,214, such compounds are not exemplified within those patents.

Orvinols and thevinols of structure 1 where R2 and R3 are interchangeably phenyl and methyl groups, R4 is H and R1 includes cyclopropylmethyl, allyl, dimethylallyl and propargyl were disclosed by Marton et al (Marton et al, 1997) without any definition of opioid activity.

Orvinols and thevinols of structure 1, where R4 is methyl, have not previously been disclosed. In addition, the inventors have found that the key Diels-Alder adduct from which the novel compounds, having R4 as methyl, are prepared in the current invention could not be synthesized by the standard methodology which had previously allowed the standard orvinols, having R4 as H, to be prepared (Lewis et al, 1971).

Buprenorphine in the Treatment of Drug Abuse

Buprenorphine displays a unique and complex pharmacology derived from the manner in which it binds to opioid receptors. Like the opiate analgesics and the antagonists naltrexone, naloxone and nalmefene, buprenorphine's primary actions are at MOPr, but it is neither an opiate agonist like morphine, nor an antagonist like naltrexone. It is classified as a partial MOPr agonist having the characteristics of both an agonist or an antagonist depending on the circumstances. As an MOPr partial agonist buprenorphine shows a ceiling to all the effects associated with MOPr agonism including importantly the potentially lethal effect of respiratory depression (in overdosage) and addiction liability. The latter is also favourably affected by the kinetics of buprenorphine's MOPr binding which has irreversible characteristics. The very slow dissociation of buprenorphine from MOPr is responsible, at least in part, for its long duration of action and the mildness of the abstinence effects when drug is withdrawn following chronic administration. The shape of the dose-response curves for buprenorphine's MOPr agonist effects is uniquely an inverted U-shape. This means that high doses have lesser MOPr agonist effects than intermediate doses which produce peak effects. This applies to respiratory depression, thus further contributing to the drug's extremely favourable acute safety profile and physical dependence liability. The very limited MOPr agonist activity of buprenorphine at high doses is complementary to the predominant MOPr antagonist activity at these doses.

The unique pharmacological profile of buprenorphine at MOPr was recognised when it was approved for the treatment of opiate abuse and dependence as an agent for detoxification and maintenance. But buprenorphine is also unique among drugs having significant MOPr agonist activity in having high affinity but no efficacy at KOPr and delta opioid receptors (DOPr), thus having only antagonist activity at these receptors. Not only does the lack of any KOPr agonist activity mean that buprenorphine avoids KOPr agonist side effects particularly dysphoria and diuresis, but KOPr antagonism is important for its potential use in treatment of substance abuse disorders other than opiate abuse. Thus KOPr antagonism contributes to its ability to inhibit cocaine self-administration in rhesus monkeys (Mello et al, 1995) and in concurrent opiate and cocaine addicts (Montoya et al, 2004). Preclinical studies also support the hypothesis that KOPr antagonists may be of utility against cocaine. The KOPr antagonists norBNI and JDTic have been shown to block stress-induced potentiation of cocaine place preference (McLaughlin et al, 2003) and to block footshock-induced reinstatement of cocaine self-administration behaviour (Beardsley et al. 2005; Redila and Chavkin, 2008). KOPr antagonists have also been shown, in rats, to selectively attenuate ethanol-dependent self-administration while leaving nondependent ethanol self-administration unaffected (Walker and Koob, 2008). This appears consistent with earlier findings of a decrease in alcohol self-administration in KOR knockout mice (Kovacs et al, 2005).

In addition to its binding to the three classical opioid receptors buprenorphine also binds as a partial agonist to the ORL-1 receptor. This receptor has a high degree of amino acid sequence homology with the classical opioid receptors, but traditional opioids, including the opium alkaloids and the antagonists naloxone, naltrexone and nalmefene have low affinity for the ORL-1 receptor. The endogenous ligand for ORL-1 receptors, orphanin FQ has been shown to inhibit the actions of cocaine (Korlinska et al, 2002) so that buprenorphine's ORL-1 activity could be associated with a similar effect. Gorelick (2007) suggested that since it is high doses of buprenorphine that significantly reduce cocaine use in patients who are both opiate and cocaine dependent (Montoya et al, 2004), it is ORL-1 receptor activation which is important for this effect. Buprenorphine at high doses has also been shown to inhibit ethanol self administration in rats, an effect that was prevented by a selective ORL-1 antagonist (Ciccocioppo et al, 2007).

In order to unmask the KOPr antagonist (and NOP/ORL-1 agonist) activity, the MOPr agonist effect of buprenorphine must be nullified. This was achieved by combining sublingual buprenorphine (4 mg/day) with oral naltrexone (50 mg/day) in a study in detoxified opiate addicts. After 12 weeks the combination-treated group showed a lower level of urines positive for opiates and cocaine metabolites than the comparison group on naltrexone (50 mg) (Gerra et al, 2006). This result, which indicated a positive contribution from buprenorphine's KOPr antagonist effect, confirmed an earlier study by Rothman et al (2000) using the same dosing regime, but without a naltrexone comparison group.

The use of naltrexone, a predominantly MOR antagonist, for relapse prevention of alcohol and opioid dependence is approved in a number of countries. There are mixed reports on the effectiveness of oral naltrexone in the treatment of opioid dependence, such that a recent Cochrane review did not find sufficient evidence to unequivocally support its use (Minozzi, 2006). More recently, sustained-release naltrexone has become available and the limited high quality data available suggests this does have advantages over oral naltrexone, including significantly higher rates of retention in treatment (Lobmaier, 2008; Comer et al, 2006). Evidence for the efficacy of naltrexone in treating alcohol dependence is stronger. It has been shown to be effective over both the short and medium term in preventing relapse, particularly when combined with psychosocial treatment (Srisurapanont and Jarusuraisin, 2008). Interestingly, the positive effect in preventing relapse to alcohol is maintained in individuals with dual cocaine/alcohol dependence or abuse (Srisurapanont and Jarusuraisin, 2008), supporting a role for MOR antagonism in reducing alcohol intake in the polydrug using community.

The case is thus made for a potent KOPr antagonist and MOPr antagonist with ORL-1 receptor agonist activity, i.e. buprenorphine with MOPr partial agonism replaced by MOPr antagonism, as a treatment for abuse of a a wide spectrum of substances both individually and collectively.

SUMMARY OF INVENTION

The present invention provides a compound of formula 2, or a pharmaceutically acceptable salt, prodrug or solvate thereof

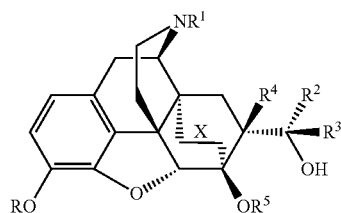

in which
R is H or alkyl
R1 is alkyl, alkenyl, or cycloalkylalkyl,
R2, R4 and R5 are H or methyl
R3 is aryl or heteroaryl, either of which may be substituted or unsubstituted, except that when R4 is H then R3 may not be phenyl when R2 is methyl, including in the diastereoisomers in which R2 and R3 are interchanged.

At C20 R2 and R3 can be interchanged to provide the opposite stereochemistry

X is a saturated bridge (—CH2CH2—) or an unsaturated bridge (—CH=CH—)

When R is alkyl it means a short chain alkyl having four carbon atoms or less and preferably one carbon atom, i.e. methyl. R is preferably H.

In R1 above, alkyl means a chain of between two and four carbon atoms optionally substituted, preferably a n-propyl group. Cycloalkylalkyl preferably means a cycloalkyl group of three to eight carbon atoms, preferably cyclopropyl or cyclobutyl attached to the basic nitrogen atom through a carbon chain of one to three carbon atoms which may be optionally substituted, and is preferably a methylene group (—CH2), with cyclopropylmethyl (CPM) being a most preferred R1 structure. Alkenyl preferably means allyl (—CH2CH=CH2) in which any of the hydrogen atoms may be substituted, preferably by one or more methyl groups. A preferred alkenyl group is allyl.

R3 is an aryl, especially phenyl, or heteroaryl group, especially one with four or five carbon atoms and a sulphur or nitrogen atom, i.e. thiophenyl, pyrrolyl or pyridyl. These may be optionally substituted with, for example, a halogen, especially fluorine or chlorine, or a short chain alkyl such as methyl, or an oxygen, for example hydroxyl or methoxy. R3 is preferably phenyl, optionally substituted with one or more of methyl, a halogen, methoxy and hydroxy.

As indicated above, when R4 is H then R3 may not be phenyl when R2 is methyl, including in the dlastereoisomers in which R2 and R3 are interchanged. This means that when R4 is H, R3 is not phenyl when R2 is methyl. Diastereoisomers are included, such that if the positions of R2 and R3 are interchanged, the exception still applies, in other words, when R4 is H and R2 is phenyl, R3 may not be methyl.

In a preferred embodiment, R is preferably H. In that embodiment, R1 is preferably CPM.

When R1 is CPM, especially when R is H, R3 is preferably aryl, particularly phenyl, or a substituted phenyl.

In some embodiments, R2 is preferably H. In others R2 is preferably methyl. In some embodiments, R4 is preferably H. In others R4 is preferably methyl. When R2 is H, R4 is preferably methyl. When R2 is methyl, R4 is preferably H. R2 may be H when R4 is H, though, and R2 may be methyl when R4 is methyl.

In the compounds of the invention of structure 2 R2 and R3 may be interchanged, but as indicated in the definition of R2, one or other must be H or Me. As mentioned previously, when R4 is H and R2 is methyl then R3 may not be phenyl and, accordingly, when the positions are interchanged, R2 may not be phenyl when R3 is methyl.

The stereochemistry shown in structure 2 when R3 is aryl or heteroaryl is preferred; however, embodiments in which R2 and R3 are interchanged are included. In particular, when the two are interchanged, a preferred embodiment Includes pyridyl as R2, especially with R3 being Me and R4 being H.

X may be —CH2CH2— or —CH=CH—, with —CH2CH2— being preferred. When X is —CH=CH—. R4 is preferably methyl. In addition, R2 is preferably H.

Compounds of the invention may be found in table 1, excluding BU127.

The invention also provides methods for the synthesis of the novel compounds of structure 2 where R, R1, R2, R3, R4, R5 are as specified above.

In particular, there is provided a method of synthesising a compound, especially a compound of the invention, or an intermediate for use in synthesising the compounds of the invention, the method comprising the step of combining an N-acylnorthebaine with methacrolein in the presence of a Lewis acid catalyst Standard methods without Lewis acid catalyst failed to give the desired compound.

The method of synthesising a compound is preferably a method of synthesising an intermediate for use in synthesising a compound of the invention. The intermediate may be a N-acyl-7alpha-formyl-7beta-methyl-6,14-endothenotetrahydronorthebaine.

Lewis acid catalysts are well known in the art. It is particularly preferred that the Lewis acid catalyst is LiBF$_4$, though BF$_3$, OEt$_2$ and NbCl$_5$ may also be used. The invention also provides a composition comprising a compound of formula 2, or a pharmaceutical acceptable salt, prodrug or solvate thereof and a pharmaceutically acceptable excipient or carrier,

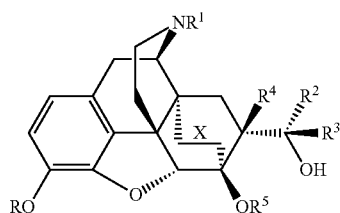

2 in which
R is H or alkyl
R1 is alkyl, alkenyl, cycloalkylalkyl
R2, R4 and R5 are H or methyl
R3 is aryl or heteroaryl either of which may be substituted or unsubstituted and X is a saturated bridge (—CH2CH2—) or an unsaturated bridge (—CH=CH—)

R, R1, R2, R3, R4 and R5 are preferably as defined above in relation to compounds of the invention. The compound to be administered includes the diastereoisomers in which R2 and R3 are interchanged.

It is preferred that when R4 is H then R3 may not be phenyl when R2 is methyl, including in the diastereoisomers in which R2 and R3 are interchanged.

Pharmaceutical compositions of this invention comprise any of the molecules of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. Preferably, the pharmaceutical compositions are administered orally or by injection. The pharmaceutical compositions may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques. Preferably, the route of administration of the composition is transdermal or intrathecal administration.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and Isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Hev or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a molecule of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the molecules of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The composition may also comprise a second active agent or may be for administration with another active agent, such as an NOP agonist or opioid antagonist.

Further is provided a method of treating a substance abuse disorder comprising administering an effective amount of a compound having structure 2 as shown above, in which
R is H or alkyl
R1 is alkyl, alkenyl, cycloalkylalkyl
R2, R4 and R5 are H or methyl
R3 is aryl or heteroaryl either of which may be substituted or unsubstituted, and
X is a saturated bridge (—CH2CH2—) or an unsaturated bridge (—CH═CH—); or a composition comprising such a compound to a subject in need thereof.

R, R1, R2, R3, R4 and R5 are preferably as defined above in relation to compounds of the invention. The compound to be administered includes the diastereoisomers in which R2 and R3 are interchanged.

It is preferred that when R4 is H then R3 may not be phenyl when R2 is methyl, including in the diastereoisomers in which R2 and R3 are interchanged.

The method of treating the substance abuse disorder may comprise a single administration of the compound or composition, or repeated administrations thereof.

The invention also provides a compound of formula 2, or a pharmaceutically acceptable salt, prodrug or solvate thereof

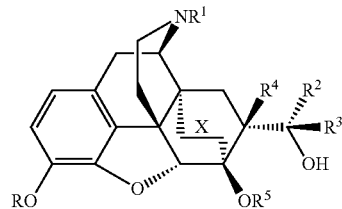

in which
R is H or alkyl
R1 is alkyl, alkenyl, cycloalkylalkyl,
R2, R4 and R5 are H or methyl
R3 is aryl or heteroaryl either or which may be substituted or unsubstituted and
X is a saturated bridge (—CH2CH2—) or an unsaturated bridge (—CH═CH—), for use in therapy, especially in the treatment of a substance abuse disorder.

R, R1, R2, R3, R4 and R5 are preferably as defined in relation to the method of treatment of the invention.

A substance abuse disorder is preferably as opiate use, particularly as a relapse prevention agent, alcohol dependence and excessive alcohol use, cocaine use, stimulant use, polydrug abuse, and nicotine use. In particular it relates to opiate use in recovering addicts. It is particularly preferred that the composition is useful for the treatment of a substance abuse disorder, especially opiate use without the need to co-administer another MOPr antagonist.

The compound may also be useful for the treatment of depression, anxiety and compulsive disorders, e.g. gambling. A combination of buprenorphine and naltrexone, the effects of which are mimicked by the compounds of the invention, has been indicated to have efficacy against a number of psychiatric disorders such as anxiety and depression. Accordingly, the compounds of the invention can also be used to treat such disorders.

The invention will now be described in detail, by way of example only.

EXPERIMENTAL

The compounds can be prepared by, for example, the methods outlined in Schemes 1, 2, 3 and 4. These methods are illustrative of how secondary and tertiary alcohols are made in these series. The exact order of some the chemical steps may be varied (for example, when the nitrogen substituent is introduced).

The compounds (structure 2), having R4=H, can be prepared as shown in Schemes 1 and 2 from N-cyclopropylmethyl-6,14-endoetheno-7-acetyltetrahydronorthebaine (5b) or N-cyclopropylmethyl-6,14-endoetheno-7-formyltetrahydronorthebaine (8b) by methods analogous to those described in British Patents GB969,263 and GB1,136,214. Thus the synthesis of series 1, with stereochemistry at C20 as depicted in 7, is shown in Scheme 1, with the equivalent compounds with opposite stereochemistry at C20 (Series 2, structure 15) shown in scheme 2. However an exception was found in the case of the synthesis of the C20-pyridyl analogues where instead of Grignard reagent the more reactive pyridyl lithium reagents had to be used. The result was that the predominant product had the stereochemistry of structure 15a Instead of the expected structure 7a.

The compounds of the invention, having R4=Me, are most readily prepared from N-cyclopropylcarbonyl northebaine (16) by a Diels-Alder reaction with methacrolein to give 17a and 17b. Addition of an aryl Grignard reagent to 17b provides secondary alcohols 18 and these can be converted to the diasteriomeric alcohols 20 by oxidation and reduction. The orvinol analogues 22 and 23 are then made by 3-O-demethylation using KOH, PrSNa or L-selectride (Scheme 3)

Ethano bridged analogues are prepared by catalytic hydrogenation of adduct 17b and then equivalent chemistry to that described for the etheno series. (Scheme 4)

Scheme 1:

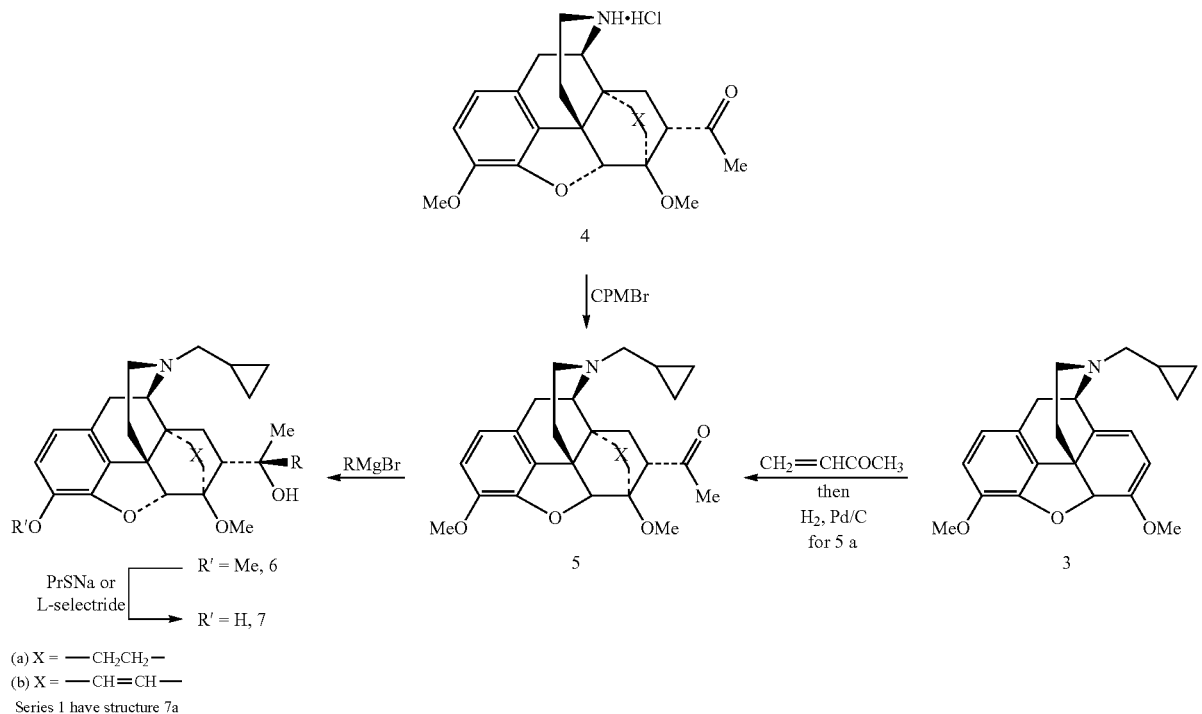

(a) X = —CH$_2$CH$_2$—
(b) X = —CH═CH—
Series 1 have structure 7a

Scheme 2:

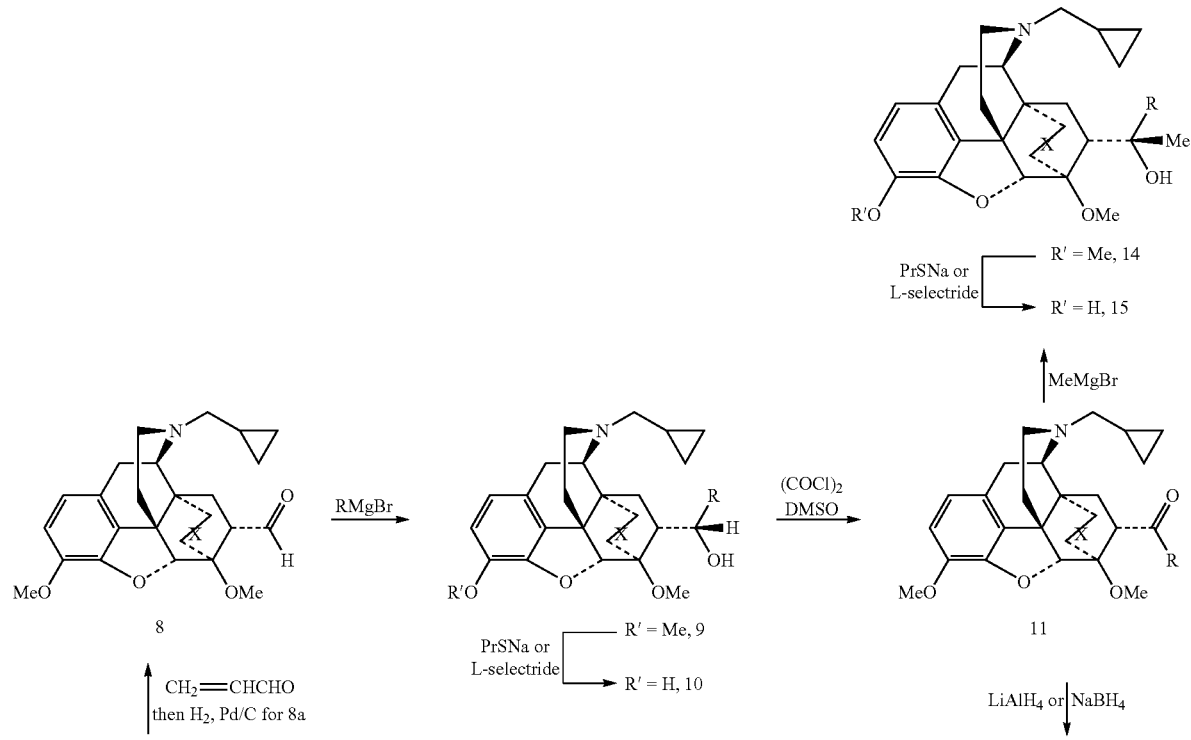

11
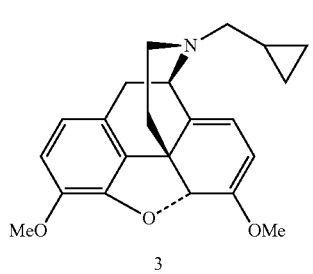
3
12
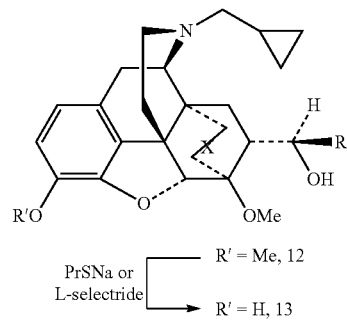
PrSNa or L-selectride → R' = Me, 12
R' = H, 13
(a) X = —CH₂CH₂—
(b) X = —CH=CH—
Series 2 have structure 15a
Series 3 have structure 13a
Series 4 have structure 10a
Scheme 3
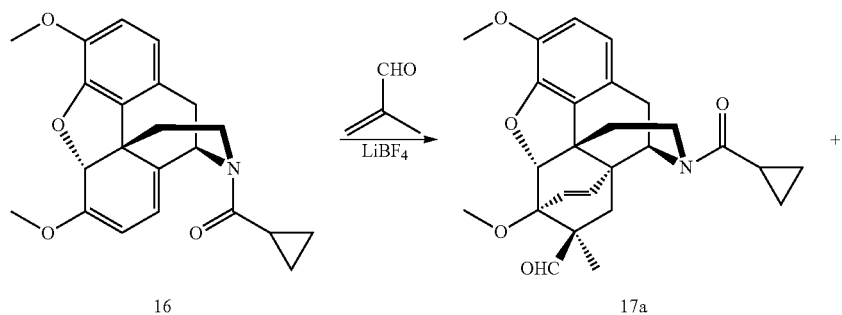
16    17a    +
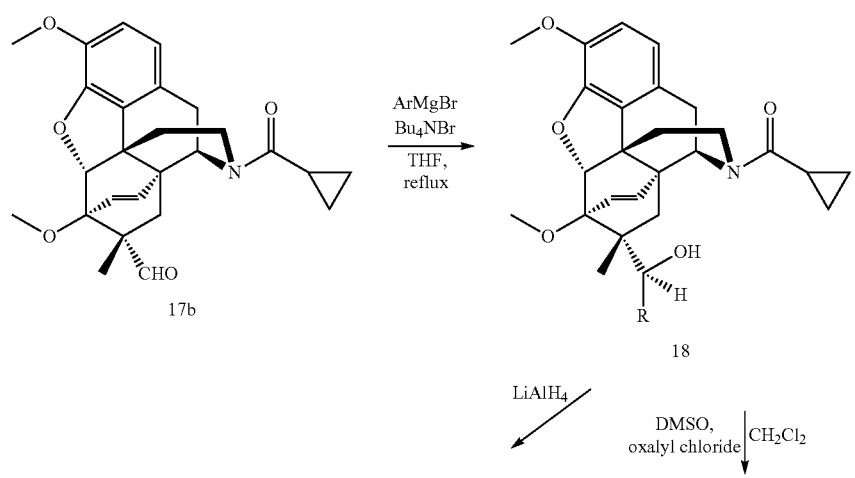
17b    18
LiAlH₄ ↙    DMSO, oxalyl chloride | CH₂Cl₂ ↓

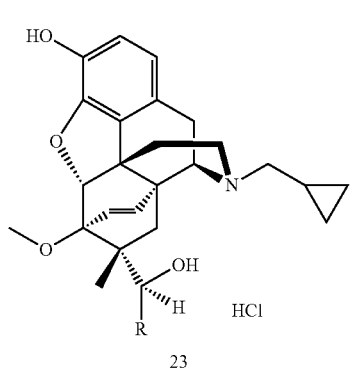
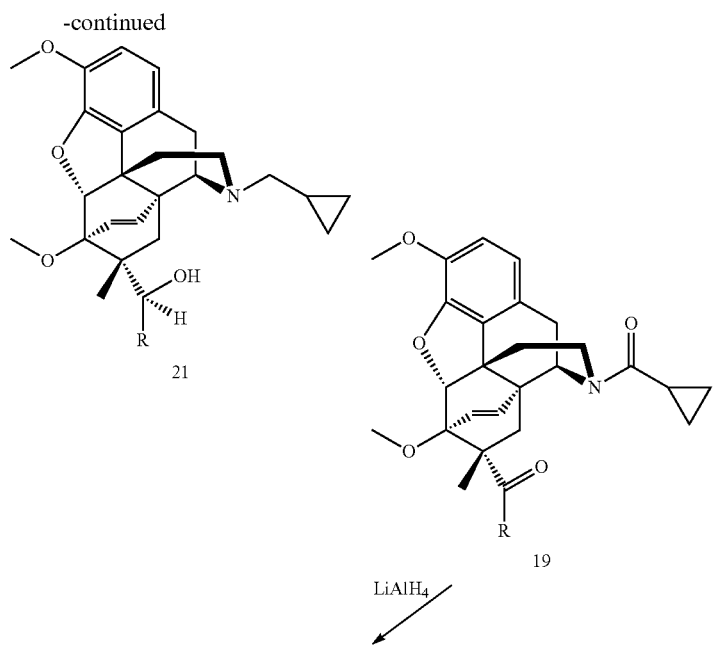
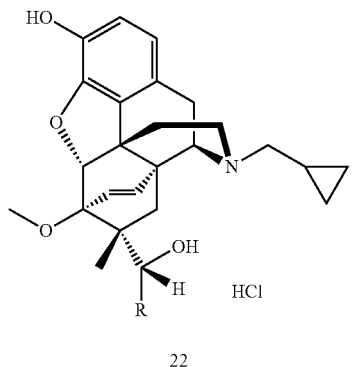
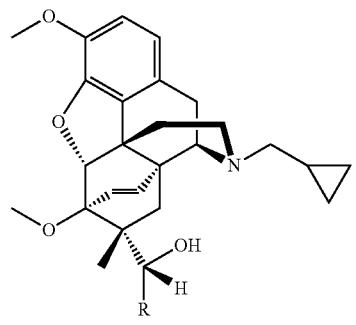
Scheme 4.
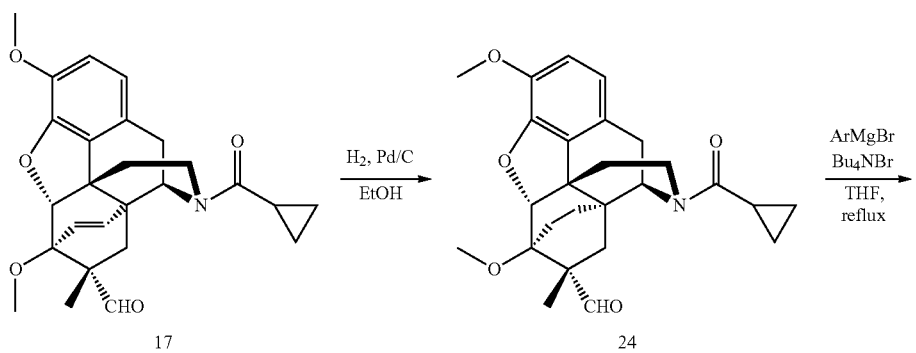

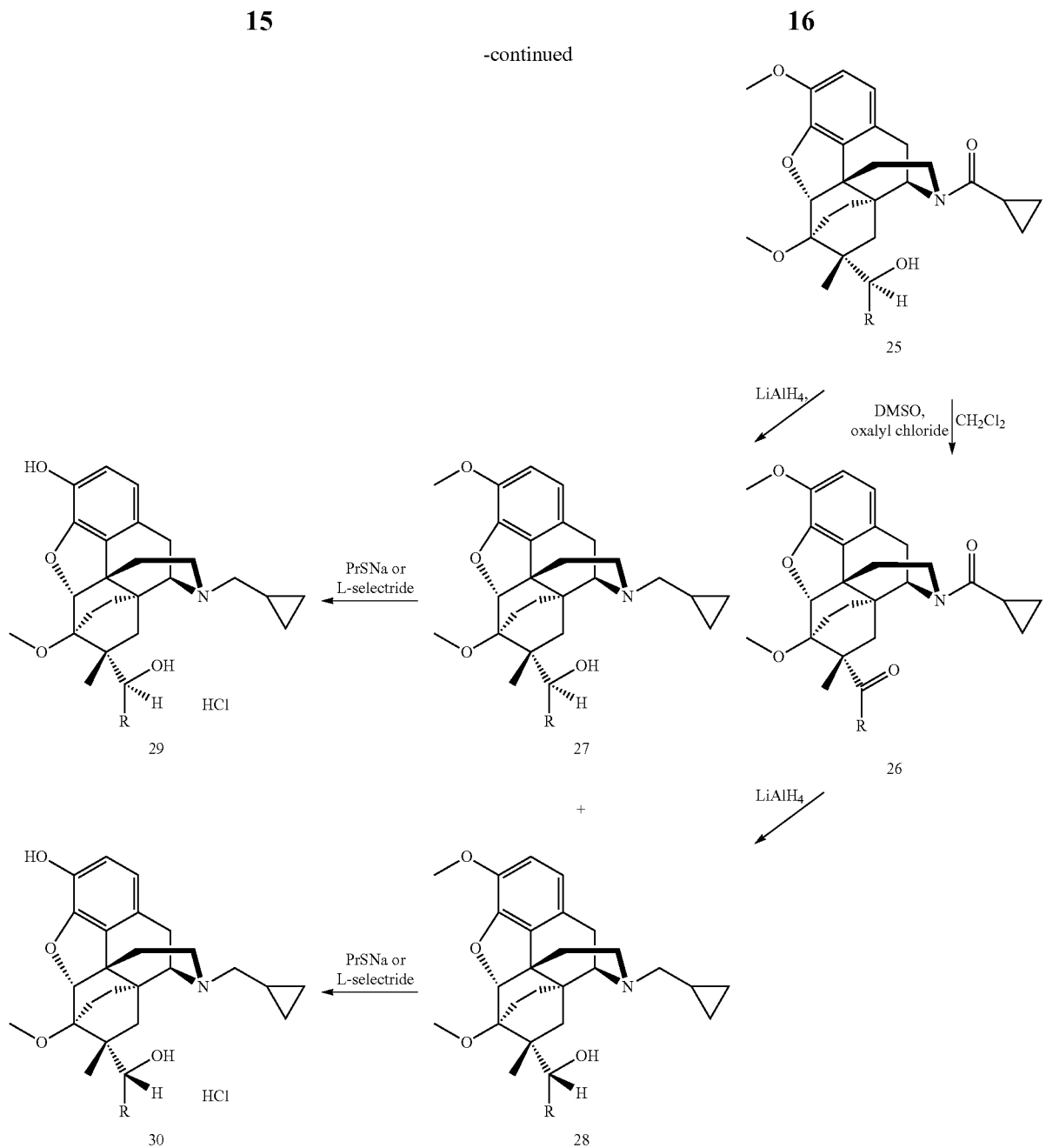

Experimental Data on Compounds
General Procedure A: Grignard Addition (Schemes 1 and 2)

The Grignard reagents were prepared form the corresponding bromides (5 mmol) by reaction with magnesium (182 mg, 7.5 mmol) in anhydrous THF (5 ml) containing a crystal of iodine). The Grignard reagents were titrated prior to use by adding 1 ml of the Grignard solution to a flask containing 1,10-phenanthroline (~2 mg) in anhydrous THF (2 ml) (purple solution) and titrating with 1M 2-butanol (anhydrous) in THF (end point pale yellow solution)]

Grignard reagent (1 M in THF, 1.2 ml, 1.2 mmol) was treated dropwise at room temperature with a solution of 5 (500 mg) or 8 (500 mg) in anhydrous toluene (12 ml). After stirring at room temperature for 20 h, the reaction was quenched by addition of saturated aqueous ammonium chloride solution (20 ml). The phases were separated and the aqueous phase extracted with EtOAc. The combined organic phases were washed with saturated aqueous sodium bicarbonate, dried over $MgSO_4$, filtered and evaporated in vacuo. The residue was purified by column chromatography over silica gel eluting with a gradient from 10% to 30% ethyl acetate in hexane. $R_f$ values are recorded from TLC eluted with 30:1:69 ethyl acetate/ammonia solution/hexane.

General Procedure B. Grignard Addition (Schemes 3 and 4)

To a solution of aldehyde 17b or 24 in dry THF (10 mL/mmol of aldehyde) were added 3 eq of $Bu_4NBr$ followed by 2 eq of arylmagnesium halide as solution in THF. The solution was heated at reflux for 48 h. cooled to RT and quenched with 0.05 mL of water. The mixture was allowed to stir for 5 min then filtered over Celite. The solids were washed with hot THF, and the solution was removed of its solvent by rotary evaporation. The remaining residue was partitioned between EtOAc (20 mL) and water (10 mL). The water layer was extracted twice with 5 mL of EtOAc. The pooled organic solvent was washed twice with 5 mL of water, once with brine, dried over $MgSO_4$, filtered and dried under reduced pressure. The residue was dissolved in a minimum amount of $Et_2O$ to induce crystallization. The crystals were collected by filtration, and dried under vacuum.

General Procedure C. Swern Oxidation:

A solution of oxalyl chloride (1.25 eq) in $CH_2Cl_2$ (3 mL/mmol) was cooled to –78° C. in a one neck flask. Into this flask was added dropwise, a solution of dry DMSO (2.6 eq) in $CH_2Cl_2$ (3 mL/mmol). The solution stirred for 5 min and then a solution 9, 18 or 25 in $CH_2Cl_2$ (2 ml/mmol) was added. The mixture stirred for 20 min and then $Et_3N$ (5 eq) was added. The reaction was removed from the cold bath, stirred for 1 h and water was added. The mixture was shaken, the organic layer was separated and washed with a saturated solution of $NH_4Cl$, then with a concentrated solution of $NaHCO_3$. The solution was washed once more with brine, dried over magnesium sulfate, filtered, and the solvents removed under reduced pressure to yield crude 11, 19 or 26 as a clear residue.

General Procedure D. $LiAlH_4$ Reduction

Substrate (11, 18, 19, 25 or 26) was dissolved in dry THF (10 mL/mmol) and added to a stirring suspension of $LiAlH_4$ (4 eq) in dry THF (5 mL/mmol) at 0° C. The suspension was allowed to warm up to RT and was stirred for 24 h. The reaction was cooled to 0° C. and quenched with water in THF. The mixture was filtered, rinsing the solids with hot THF. The solution was subjected to rotary evaporation to yield an oil that was subjected to silica gel column chromatography eluting with 15% EtOAc in petroleum ether to yield product.

General Procedure E. O-Demethylation Using NaSPr/HMPA:

A solution of 6, 9, 12, 14, 20, 21, 27 or 28 in dry HMPA (6 ml/mmol) was added sodium propanethiolate (6 eq). The reaction was stirred for 3 h at 115° C., then cooled to RT and quenched with 7 mL/mmol of a concentrated solution of $NH_4Cl$. The mixture was extracted three times with $Et_2O$. The organic layer was then extracted five times with water, once with brine, dried over $MgSO_4$, filtered and the solvents were removed under reduced pressure. The residue was then subjected to silica gel flash column chromatography eluting with a gradient of EtOAc in petroleum ether. The fractions containing the compound of interest were then evaporated to dryness and dissolved in a 2 M solution of HCl in EtOH, and then induced to crystallize upon addition of EtOAc. The crystals were collected by filtration, and dried under vacuum.

General Procedure F. O-Demethylation Using L-Selectride:

L-Selectride® in THF (5 equivalents of a 1M solution) was added to the starting material (6, 9, 12, 14, 20, 21, 27 or 28) under nitrogen and the resulting solution heated to 80° C. and stirred for 14 hours, during which time a change from clear to white and opaque was observed. Excess L-Selectride® was quenched with water and solvent removed under vacuum. The resulting residue was extracted into dichloromethane, washed with distilled water and saturated brine solution, dried ($MgSO_4$) and solvents again removed under vacuum.

N-Cylcopropylmethyl-6,14-endo-ethanonorthevinone (5a) [Marton et at 1997]

A solution of 4a (6 g, 14.8 mmol) in anhydrous DMF (36 ml) was treated sequentially at room temperature with sodium bicarbonate (5 g, 60 mmol) and (bromomethyl)cyclopropane (1.87 ml, 19.3 mmol). The resulting suspension was heated to 90° C. and stirred for 20 h. On cooling, the DMF was removed in vacuo and the residue dissolved in water and rendered basic with 2 M NaOH solution. The product was extracted into chloroform and the organic phases washed with brine, dried over $MgSO_4$, filtered and evaporated to dryness. The resulting yellow solid was purified by column chromatography over silica gel (50% ethyl acetate in hexane, $R_f$=0.50) affording 6.15 g 5a as a white solid (98%). Mp 105-106° C. $^1H$ NMR (270 MHz, $CDCl_3$) δ 0.04-0.10 (2H, m), 0.43-0.49 (2H, m), 0.63-0.80 (1H, m), 1.22-1.34 (1H, m), 1.49-1.75 (4H, m), 1.96-2.08 (1H, m), 2.20-2.38 (4H, m), 2.25 (3H, s), 2.58-2.77 (2H, m), 2.93-3.11 (3H, m), 3.42 (3H, s), 3.86 (3H, s), 4.47 (1H, s), 6.55 (1H, d, J=8.0 Hz), 6.63 (1H, s), 3.86 (3H, s), 4.47 (1H, s), 6.55 (1H, d, J=8.0 Hz), 6.63 (1H, d, J=8.0 Hz). $^{13}C$ NMR (68 MHz, $CDCl_3$) δ 3.4, 4.2, 9.6, 17.6, 22.8, 28.8, 30.5, 33.9, 35.4, 35.5, 43.8, 46.6, 49.8, 52.4, 56.8, 58.4, 59.9, 77.8, 94.8, 113.9, 119.2, 128.9, 132.8, 141.8, 146.8, 211.1. HRMS ($ESI^+$) calcd for $C_{26}H_{34}NO_4$ ($MH^+$), 424.2488; found 424.2485.

N-Cyclopropylmethyl-6,14-dihydronorthevinal (8a) and N-cyclopropylmethylnorthevinal (8b)

N-CPMnorthebaine (3) (1 equiv.) and acrolein (1.2 equiv.) were heated to reflux in toluene (4 mL/mmol) overnight. The solvent and excess dienophile were removed in vacuo and the product purified by silica gel chromatography (8b: 74%), Rf (EtOAc:NH4OH, 99.5:0.5) 0.58,. $^1H$ NMR (270 MHz, $CDCl_3$) δ (0.14 (2H, m), 0.50 (2H, m), 0.83 (1H, m), 1.45 (1H, dd), 2.98 (1H, dd), 3.11 (1H, d), 3.57 (1H, d), 3.62 (3H, s), 3.82 (3H, s), 4.64 (1H, d), 5.59 (1H, d), 5.89 (1H, d), 6.52 (1H, d), 6.62 (1H, d), 9.43 (1H, d); $^{13}C$ NMR (68 MHz, $CDCl_3$) δ 3.43, 4.17, 9.44, 23.21, 26.76, 33.45, 42.92, 43.97, 48.05, 49.87, 52.70, 56.56, 57.11, 59.80, 80.92, 93.62, 113.39, 119.51, 126.47, 128.15, 133.96, 137.45, 141.93, 147.93, 201.96; LRMS (EI) 407 (M+). HRMS found 407.2096, $C_{25}H_{29}NO_4$ requires 407.2097.

This adduct 8b (6.0 g, 14.7 mmol) was dissolved in EtOH (45 mL) and treated with 10% Pd/C (60 mg) under a $H_2$ atmosphere at 65 psi at 50° C. for 24 h. After cooling to rt the catalyst was removed by filtration through Celite and the solvent removed in vacuo. 5.9 g (8a: 98%), Rf (Hexane:EtOAc:NH4OH, 33:66:1) 0.48;. $^1H$ NMR (270 MHz, $CDCl_3$) δ 0.09 (2H, m), 0.49 (2H, m), 0.76 (1H, m), 3.00 (1H, d), 3.51 (3H, s), 3.87 (3H, s), 4.58 (1H, d), 6.58 (1H, d), 6.72 (1H, d), 9.92 (1H, d); $^{13}C$ NMR (68 MHz, $CDCl_3$) δ 3.40, 4.11, 9.46, 19.95, 22.79, 26.72, 28.64, 35.33, 35.46, 43.70, 46.02, 48.80, 51.67, 56.68, 58.45, 59.86, 77.37, 92.37, 113.86, 119.10, 119.32, 128.58, 132.39, 141.82, 203.33; m/z (EI) 409 ($M^+$); HRMS (EI) found 409.2263, $C_{25}H_{31}NO_4$ requires 409.2253.

Series 1, Scheme 1: R=Ph (1'S,5α,6R,7R,14α)-1'-phenyl-1'-(4,5-epoxy-7,8-dihydro-3-hydroxy-6-methoxy-17-cyclopropylmethyl-6,14-ethano-morphinan-7-yl)-ethan-1'-ol (BU127)

5 was treated as in procedure A with phenylmagnesium bromide followed by procedure E or F. White solid, ($R_f$=0.21; 0.5% $NH_4OH$, 30% EtOAc in hexane; column ran in 30% EtOAc in hexane). $^1H$ NMR (400 MHz, $CDCl_3$) δ −0.10-0.00 (2H, m), 0.31-0.42 (2H, m), 0.55-0.62 (1H, m), 0.69-0.77 (1H, m), 0.91 (1H, dd, J=13.5 and 9.5 Hz), 1.02-1.10 (1H, m), 1.58 (1H, dd, J=12.5 and 2.5 Hz), 1.76-1.90 (3H, m), 1.80 (3H, s), 1.94-2.02 (1H, m), 2.10-2.20 (5H, m), 2.45 (1H, dd, J=11.5 and 5.0 Hz), 2.85-2.93 (2H, m), 3.57 (3H, s), 4.45 (1H, d, J=2.0 Hz), 5.49 (1H, s), 6.48 (1H, d, J=8.0 Hz), 6.66 (1H, d, J=8.0 Hz), 7.23-7.26 (1H, m), 7.32-7.36 (2H, m), 7.51-7.53 (2H, m). $^{13}C$ NMR (100.6 MHz, $CDCl_3$) δ 3.3, 4.2, 9.4, 18.0, 22.9, 23.7, 30.0, 32.7, 35.6, 36.2, 43.6, 47.3, 48.5, 52.9, 58.1, 59.6, 77.5, 80.9, 97.6, 116.4, 119.7, 126.2, 126.9, 128.0, 128.5, 132.5, 137.3, 145.5, 147.2. HRMS (ESI+) calcd for C$_{31}$H$_{38}$NO$_4$ (MH+), 488.2795; found 488.2794 (100%).

Series 1, Scheme 1, R=2-thienyl: (1'S,5α,6R,7R, 14α)-1'-(2-thienyl)-1'-(4,5-epoxy-7,8-dihydro-3-hydroxy-6-methoxy-17-cyclopropyimethyl-6,14-ethano-morphinan-7-yl)-ethan-1'-ol (BU08026)

5 was treated as in procedure A with 2-thienyl magnesiumbromide followed by procedure E or F. Rf (30% EtoAc-Pet.Ether-0.5% NH$_3$) 0.5. δ$_H$ (270 MHz; CDCl$_3$) 7.2 (1H, d, J 4.2, 1×2-thienyl.CH), 6.9 (1H, t, J 3.6, 1×2-thienyl.CH), 6.9 (1H, d, J 4.9, 1 ×2-thienyl.CH). 6.7 (1H, d, J 8.2, CH), 6.5 (1H, d, J 8.9, CH), 5.8 (1H, s, 21-OH), 4.4 (1H, s, 5α-H), 3.9 (3H, s, 3-OCH$_3$), 3.6 (3H, s, 6-OCH$_3$), 2.9 (1H, d, J 19.0, 10β-H), 2.9 (1H, d, J 7.2, 9α-H), 0.6-0.7 (1H, m, N—CH$_2$CH(CH$_2$—CH$_2$—)), 0.3-0.4 (2H, m, N—CH$_2$CH(CH$_2$—CH$_2$—)), 0 (2H, m, N—CH$_2$CH(CH$_2$—CH$_2$—)).
By a similar method the following ligands were prepared:

Series 1, Scheme 1, R=m-tolyl: (1'S,5α,6R,7R,14α)-1'-(3-methylphenyl)-1'-(4,5-epoxy-7,8-dihydro-3-hydroxy-6-methoxy-17-cyclopropylmethyl-6,14-ethano-morphinan-7-yl)-ethan-1'-ol (BU10092)

Rf (30% EtoAc-Pet.Ether-0.5% NH$_3$) 0.8. δ$_H$ (270 MHz; CDCl$_3$) 7.5-7.6 (1H, m, 4×aryl.CH), 7.1 (3H, d, J 3.3, 2-methylphenyl), 6.7 (1H, d, J 8.3, CH). 6.6 (1H, d, J 8.2, CH), 5.9 (1H, s, 21-OH), 4.4 (1H, s, 5α-H), 3.9 (3H, s, 3-OCH$_3$), 3.3 (3H, s, 6-OCH$_3$), 2.9 (2H, d, J 19.0, 10β-H), 2.9 (1H, d, J 7.2, 9α-H), 0.6-0.7 (1H, m, N—CH$_2$CH(CH$_2$—CH$_2$—)), 0.3-0.4 (2H, m, N—CH$_2$CH(CH$_2$—CH$_2$—)), −0.1-0 (2H, m, N—CH$_2$CH(CH$_2$—CH$_2$—)).

Series 1, Scheme 1, R=p-t-butylphenyl: (1'S,5α,6R, 7R,14α)-1'-(4''-t-butylphenyl)-1'-(4,5-epoxy-7,8-dihydro-3-hydroxy-6-methoxy-17-cyclopropylmethyl-6,14-ethanomorphinan-7-yl)-ethan-1'-ol (BU08024)

R$_f$ 0.33 $^1$H NMR (400 MHz, CDCl$_3$) δ −0.07 (2H, m), 0.31-0.33 (2H, d, J=8.0 Hz), 068-072 (1H, m), 0.73-0.86 (1H, m), 0.86-0.92 (1H, m), 0.99-1.03 (1H, m), 1.31 (10H, s), 1.52-1.55 (1H, d, J=12.5 Hz), 1.77 (5H, s), 1.81-1.84 (1H,m), 2.03-2.10 (1H, m), 2.13-2.20 (5H, m), 2.46-2.48 (1H, m), 2.77-278 (1H, m), 2.87-2.91 (1H, d, J=18.3 Hz), 3.54 (3H, s), 4.43 (1H, s), 5.44 (1H, s), 6.44-6.46 (2H, d, J=8.0 Hz), 6.61-6.63 (2H, d, J=8.0 Hz), 7.32-7.33 (2H, d, J=4.7 Hz), 7.34 (2H, d, J=4.7 Hz); $^{13}$C NMR (100.6 MHz, CDCl$_3$) δ 3.4, 3.5, 9.1, 17.8, 23.0, 23.4, 29.8, 31.3, 32.4, 34.3, 35.5, 36.0, 43.2, 47.0, 48.3, 52.7, 58.5, 59.2, 80.7, 97.2, 116.3, 119.4, 124.6, 125.6, 128.1, 132.3, 137.2, 144.0, 145.4, 149.3; ESIMS m/z: 544 [M+1]+.

Series 1, Scheme 1, R=p-i-propylphenyl: (1'S,5α,6R, 7R,14α)-1'-(4-isopropylphenyl)-1'-(4,5-epoxy-7,8-dihydro-3-hydroxy-6-methoxy-17-cyclopropylmethyl-6,14-ethanomorphinan-7-yl)-ethan-1'-ol (BU10096)

$^1$H NMR (CDCl$_3$) δ −0.09--0.04 (2H, m), 0.31-0.0.35 (2H, m), 0.57-0.60 (1H, m), 0.68-0.75 (1H, m), 0.86-0.92 (1H, m), 1.00-1.05 (1H, m), 1.24 (6H, d, J=6.88 Hz), 1.56 (1H, s), 1.78 (3H, s), 1.79-1.85 (3H, m), 1.98-2.04 (2H, m), 2.10-2.23 (4H, m), 2.45-2.49 (1H, m), 2.78 (1H, d, J=6.40 Hz), 2.88-2.93 (2H, m), 3.56 (3H, s), 4.45 (1H, s), 4.61 (1H, bd), 5.30 (1H, bd), 6.47 (1H, d, J=8.0 Hz), 6.66 (1H, d, J=8.0 Hz), 7.17 (2H, d, J=8.1 Hz), 7.40 (2H, d, J=8.1 Hz); $^{13}$C NMR, 400 MHz, (CDCl$_3$) δ 3.40, 3.65, 9.29, 17.92, 23.05, 23.59, 23.92, 24.12, 29.87, 32.60, 33.72, 35.61, 36.16, 43.35, 47.25, 48.53, 52.71, 58.56, 59.39, 80.80, 97.56, 116.22, 119.52, 125.81, 125.91, 128.51, 132.52, 137.12, 144.75, 145.48, 147.14. HRMS, m/z for (C$_{34}$H$_{44}$NO$_4$) [MH]+, calcd—530.3270, found—530.3285.

Series 1, Scheme 1, R=p-chlorophenyl: (1'S,5α,6R, 7R,14α)-1'-(4-chlorophenyl)-1'-(4,5-epoxy-7,8-dihydro-3-hydroxy-6-methoxy-17-cyclopropylmethyl-6, 14-ethanomorphinan-7-yl)-ethan-1'-ol (BU10097)

$^1$H NMR (CDCl$_3$) δ −0.03--0.02 (2H, m), 0.37-0.0.41 (2H, m), 0.58-0.62 (1H, m), 0.71-0.74 (1H, m), 0.85-0.90 (1H, m), 0.99-1.05 (1H, m), 1.54 (1H, m), 1.75 (3H, s), 1.77-1.84 (3H, m), 1.99-2.05 (2H, m), 2.14-2.22 (4H, m), 2.44-2.48 (1H, m), 2.86-2.90 (2H, m), 3.58 (3H, s), 4.42 (1H, s), 4.63 (1H, bd), 5.46 (1H, bd), 6.51 (1H, d, J=8.0 Hz), 6.69 (1H, d, J=8.0 Hz), 7.29 (2H, d, J=11.1 Hz), 7.43 (2H, d, J=11.1 Hz); $^{13}$C NMR, 400 MHz, (CDCl$_3$) δ 3.20, 4.03, 9.27, 17.83, 22.79, 23.48, 29.86, 32.60, 35.59, 36.09, 43.45, 47.29, 48.52, 52.81, 57.99, 59.50, 80.85, 97.48, 116.32, 119.60, 127.60, 127.93, 128.49, 132.35, 132.54, 137.13, 145.44, 146.10; HRMS, m/z for (C$_{31}$H$_{37}$ClNO$_4$): [MH]+; calcd 522.2411, found—522.2515.

Series 1, Scheme 1, R=m-chlorophenyl: (1'S,5α,6R, 7R,14α)-1'-(3-chlorophenyl)-1'-(4,5-epoxy-7,8-dihydro-3-hydroxy-6-methoxy-17-cyclopropylmethyl-6, 14-ethanomorphinan-7-yl)-ethan-1'-ol (BU10098)

$^1$H NMR, 400 MHz, (CDCl$_3$) δ −0.05--0.02 (2H, m), 0.36-0.0.42 (2H, m), 0.60-0.62 (1H, m), 0.70-0.76 (1H, m), 0.89-0.93 (1H, m), 1.02-1.07 (1H, m), 1.56 (1H, s), 1.75-1.85 (6H, m), 2.01-2.06 (2H, m), 2.15-2.23 (4H, m), 2.44-2.48 (1H, m), 2.87-2.94 (2H, m), 3.57 (3H, s), 4.43 (1H, s), 4.68 (1H, s), 5.48 (1H, bd), 6.48 (1H, d, J=8.0 Hz), 6.67 (1H, d, J=8.0 Hz), 7.21-7.28 (2H, m), 7.37 (1H, d, J=10.6 Hz), 7.53 (1H, s): $^{13}$C NMR, 400 MHz, (CDCl$_3$) δ 3.21, 4.03, 9.27, 17.87, 22.84, 23.54, 29.84, 32.53, 35.60, 36.10, 43.46, 47.27, 48.44, 52.81, 57.98, 59.44, 80.87, 97.42, 116.34, 119.62, 124.40, 126.50, 126.92, 128.47, 129.05, 132.37, 133.89, 137.14, 145.44, 149.68; HRMS, m/z for (C$_{31}$H$_{37}$FNO$_4$) [MH]+; calcd 522.2411, found—522.2447.

Series 1, Scheme 1, R=3,5-dimethylphenyl: (1'S,5α, 6R,7R,14c)-1'-(3,5-dimethylphenyl)-1'-(4,5-epoxy-7, 8-dihydro-3-hydroxy-6-methoxy-17-cyclopropylmethyl-6,14-ethanomorphinan-7-yl)-ethan-1'-ol (BU10100)

$^1$H NMR (CDCl$_3$) δ −0.04--0.01 (2H, m), 0.34-0.0.42 (2H, m), 0.61-0.65 (1H, m), 0.70-0.76 (1H, m), 0.94-0.99 (1H, m), 1.04-1.11 (1H, m), 1.56 (1H, s), 1.76 (3H, s), 1.79-1.86 (3H, m), 2.00-2.07 (2H, m), 2.14-2.24 (4H, m), 2.33 (6H, s), 2.41-2.45 (1H, m), 2.90-2.94 (2H, m), 3.56 (3H, s), 4.45 (1H, s), 4.80 (1H, bd), 5.41 (1H, bd), 6.48 (1H, d, J=8.0 Hz), 6.66 (1H, d, J=8.0 Hz), 6.87 (1H, s), 7.10 (2H, s): $^{13}$C NMR, 400 MHz, (CDCl$_3$) δ 3.00, 4.23, 9.19, 18.12, 21.59, 22.78, 23.83, 29.87, 32.53, 35.52, 36.09, 43.67, 47.17, 48.16, 52.70, 57.81, 59.27, 80.87, 97.34, 116.29, 119.53, 123.90, 128.29, 128.45, 132.48, 136.93, 137.16, 145.47, 147.41; HRMS, m/z for (C$_{33}$H$_{42}$NO$_4$) [MH]$^+$: calcd 516.3114, found—516.3145.

Series 1, Scheme 1, R=o-tolyl: (1'S,5α,6R,7R,14α)-1'-(2-methylphenyl)-1'-(4,5-epoxy-7,8-dihydro-3-hydroxy-6-methoxy-17-cyclopropylmethyl-6,14-ethanomorphinan-7-yl)-ethan-1'-ol (BU10101)

$^1$H NMR (CDCl$_3$) δ –0.08--0.03 (2H, m), 0.31-0.0.38 (2H, m), 0.56-0.58 (1H, m), 0.69-0.76 (1H, m), 0.83-0.89 (1H, m), 1.02-1.09 (1H, m), 1.59-1.63 (1H, m), 1.79-1.89 (6H, m), 1.98-2.05 (1H, m), 2.13-2.23 (4H, m), 2.45-2.49 (1H, m), 2.62-2.66 (1H, m), 2.75 (3H, s), 2.84-2.93 (2H, m), 3.56 (3H, s), 4.45 (1H, s), 4.62 (1H, bd), 5.06 (1H, bd), 6.48 (1H, d, J=8.0 Hz), 6.67 (1H, d, J=8.0 Hz), 7.07-7.17 (3H, m), 7.22-7.24 (1H, m): $^{13}$C NMR, 400 MHz, (CDCl$_3$) δ 3.17, 4.06, 9.22, 18.24, 22.76, 22.84, 25.93, 29.87, 32.66, 35.63, 36.11, 43.52, 43.72, 47.34, 52.68, 57.92, 59.47, 79.68, 80.85 97.80, 116.27, 119.55, 124.83, 126.84, 127.50, 128.56, 132.43, 132.81, 136.84, 137.11, 143.64, 145.49; HRMS, m/z for (C$_{32}$H$_{40}$NO$_4$), [MH]$^+$, calcd—502.2957, found—502.3017.

Series 1, Scheme 1, R=4-fluorophenyl: (1'S,5α,6R,7R,14α)-1'-(4-fluorophenyl)-1'-(4,5-epoxy-7,8-dihydro-3-hydroxy-6-methoxy-17-cyclopropylmethyl-6,14-ethanomorphinan-7-yl)-ethan-1'-ol (BU10102)

$^1$H NMR (CDCl$_3$) δ –0.06--0.03 (2H, m), 0.35-0.0.40 (2H, m), 0.58-0.62 (1H, m), 0.70-0.76 (1H, m), 0.84-0.89 (1H, m), 0.99-1.06 (1H, m), 1.59 (1H, s), 1.74-1.84 (6H, m), 1.94-2.07 (2H, m), 2.14-2.22 (4H, m), 2.44-2.48 (1H, m), 2.85-2.91 (2H, m), 3.58 (3H, s), 4.44 (1H, s), 4.59 (1H, s), 5.45 (1H, bd), 6.48 (1H, d, J=8.0 Hz), 6.67 (1H, d, J=8.0 Hz), 6.99-7.04 (2H, m), 7.41-7.46 (2H, m): $^{13}$C NMR, 400 MHz, (CDCl$_3$) δ 3.22, 3.99, 9.27, 17.80, 22.83, 23.58, 29.86, 32.64, 35.60, 36.09, 43.45, 47.29, 48.72, 52.81, 58.05, 59.48, 80.83, 97.54, 114.39, 114.60, 116.32, 119.59, 126.64, 127.70, 128.47, 128.98, 132.35, 137.13, 143.35, 145.45, 160.57; HRMS, m/z for (C$_{31}$H$_{37}$FNO$_4$), [MH]$^+$: calcd 506.2707, found—506.2749.

Series 1, Scheme 1, R=3-fluorophenyl: (1'S,5α,6R,7R,14α)-1'-(3-fluorophenyl)-1'-(4,5-epoxy-7,8-dihydro-3-hydroxy-6-methoxy-17-cyclopropylmethyl-6,14-ethanomorphinan-7-yl)-ethan-1'-ol BU10103

$^1$H NMR (CDCl$_3$) δ –0.05--0.03 (2H, m), 0.35-0.0.40 (2H, m), 0.58-0.63 (1H, m), 0.70-0.76 (1H, m), 0.87-0.93 (1H, m), 1.01-1.09 (1H, m), 1.60 (1H, s), 1.75-1.86 (6H, m), 1.97-2.14 (2H, m), 2.17-2.22 (4H, m), 2.45-2.49 (1H, m), 2.81-2.94 (2H, m), 3.58 (3H, s), 4.44 (1H, s), 4.64 (1H, s), 5.45 (1H, bd), 6.48 (1H, d, J=J=8.0 Hz), 6.67 (1H, d, J=J=8.0 Hz), 6.92-6.97 (1H, m), 7.24-7.29 (3H, m): $^{13}$C NMR. 400 MHz, (CDCl$_3$) δ 3.28, 3.94, 9.28, 17.83, 22.85, 23.51, 29.86, 32.51, 35.60, 36.09, 43.40, 47.28, 48.52, 52.81, 58.09, 59.49, 80.84, 97.48, 113.23, 113.45, 113.69, 116.31, 119.61, 121.76, 128.48, 129.17, 132.38, 137.13, 145.44, 150.23, 161.63; HRMS, m/z for (C$_{31}$H$_{37}$FNO$_4$), [MH]$^+$: calcd 506.2707, found—506.2749.

Series 1, Scheme 1 R=3-methyl-2-thienyl: (1'S,5α,6R,7R,14α)-1'-(3-methyl-2-thienyl)-1'-(4,5-epoxy-7,8-dihydro-3-hydroxy-6-methoxy-17-cyclopropylmethyl-6,14-ethanomorphinan-7-yl)-ethan-1'-ol (BU10093)

Rf (30% EtOAc.Pet.Ether-0.5% NH$_3$) 0.17. δ$_H$ (400 MHz; CDCl$_3$) 7.03 (1H, d, J 5.04, 1× thienyl.CH), 6.76 (1H, d, J 5.12, 1× thienyl.CH), 6.68 (1H, d, J 8.04, 2-H), 6.50 (1H, d, J 8.08, 1-H), 5.30 (1H, s, 20-OH), 4.51 (1H, s, 3-OH), 4.46 (1H, s, 5β-H), 3.56 (3H, s, 6-OCH$_3$), 2.93 (1H, d, J 18.04, 10β-H), 2.90 (1H, d, J 6.36, 9α-H), 2.46-2.51 (2H, m, includes 15/16-NCH$_2$, CH$_2$—), 2.48 (3H, s, 1× thienyl.CH$_3$), 2.15-2.31 (5H, m, includes 7β-H, 10α-H, 15/16-NCH$_2$, CH$_2$—), 1.79-1.89 (3H, m, 15/16-NCH$_2$, CH$_2$—, 2×18/19-H), 1.87 (3H, s, 20-CH$_3$), 1.60-1.64 (1H, m, 15/16-NCH$_2$, CH$_2$—), 1.04-1.10 (1H, m, 8α-H), 0.68-0.78 (1H, m, 18/19-H), 0.62-0.68 (1H, m, N—CH$_2$CH(CH$_2$—CH$_2$—)), 0.34-0.45 (2H, m, N—CH$_2$CH(CH$_2$—CH$_2$—)), –0.02-0.01 (2H, m, N—CH$_2$CH(CH$_2$—CH$_2$—)); δ$_C$ (100.56 MHz; CDCl$_3$) 145.49, 144.06, 137.18, 133.14, 132.40, 131.75, 128.47, 121.22, 119.59, 116.35, 97.60, 80.53, 59.45 (NCH$_2$CH(CH$_2$)$_2$), 57.94, 52.78, 47.35, 43.54 (CH$_2$), 36.09, 35.63 (CH$_2$), 32.20 (CH$_2$), 29.84 (CH$_2$), 25.61, 22.80 (CH$_2$), 21.03, 18.00 (CH$_2$), 16.02, 14.20, 9.30, 4.10 (CH$_2$), 3.22 (CH$_2$). m/z 508 (M$^+$+1), (Found M$^+$+1, 508.2572. C$_{30}$H$_{38}$NO$_4$S requires 508.2522).

Series 1, Scheme 1, R=p-Tolyl (1'S,5α,6R,7R,14)-1'-(4-methyl-phenyl)-1'-(4,5-epoxy-7,8-dihydro-3-hydroxy-6-methoxy-17-cyclopropylmethyl-6,14-ethanomorphinan-7-yl)-ethan-1'-ol (BU10135)

Rf (30% EtOAc.Pet.Ether-0.5% NH$_3$) 0.23. δ$_H$ (400 MHz; CDCl$_3$) 7.39 (2H, d, J 8.20, 2× aryl.CH), 7.14 (2H, d, J 7.92, 2× aryl.CH), 6.68 (1H, d, J 8.04, 2-H), 6.49 (1H, d, J 8.08, 1-H), 5.42 (1H, s, 20-OH), 4.62 (1H, s, 3-OH), 4.51 (1H, s, 5β-H), 3.57 (3H, s, 6-OCH$_3$), 2.91 (1H, d, J 18.88, 10β-H), 2.87 (1H, d, J 6.80, 9α-H), 2.43-2.47 (1H, m, 15/16-NCH$_2$, CH$_2$—), 2.35 (3H, s, 1× aryl.CH$_3$), 2.12-2.21 (4H, m, includes 7β-H, 10α-H), 2.07-2.12 (1H, m, 15/16-NCH$_2$, CH$_2$—), 1.95-2.02 (1H, m, 15/16-NCH$_2$, CH$_2$), 1.82-1.88 (1H, m, 15/16-NCH$_2$, CH$_2$—), 1.79-1.83 (1H, m, 8β-H), 1.77 (3H, s, 20-CH$_3$), 1.00-1.09 (1H, m, 18/19-H), 0.87-0.93 (1H, m, 8α-H), 0.69-0.76 (1H, m, 18/19-H), 0.56-0.64 (1H, m, N—CH$_2$CH(CH$_2$—CH$_2$—)), 0.32-0.43 (2H, m, N—CH$_2$CH(CH$_2$—CH$_2$—)), –0.09-0 (2H, m, N—CH$_2$CH(CH$_2$—CH$_2$—)); δ$_C$ (100.56 MHz; CDCl$_3$) 145.34, 137.00, 136.03, 132.38, 128.45, 125.86, 119.45, 116.13, 80.71, 59.41 (NCH$_2$CH(CH$_2$)$_2$), 57.88, 52.72, 48.30, 47.14, 43.42 (CH$_2$), 35.97 (CH$_2$), 32.49, 22.64 (CH$_2$), 20.98, 17.86 (CH$_2$), 9.17, 4.00 (CH$_2$), 3.13 (CH$_2$). m/z 502 (M$^+$+1), (Found M$^+$+1, 502.3048. C$_{32}$H$_{40}$NaO$_4$ requires 502.2957).

Series 1, Scheme 1, R=5-Chloro-2-Thienyl (1'S,5α,5R,7R,14α)-1'-(5-chloro-2-thenyl)-1'-(4,5-epoxy-7,8-dihydro-3-hydroxy-6-methoxy-17-cyclopropylmethyl-6,14-ethanomorphinan-7-yl)-ethan-1'-ol (BU10136)

Rf (30% EtOAc.Pet.Ether-0.5% NH$_3$) 0.12. δ$_H$ (400 MHz; CDCl$_3$) 6.72 (1H, d, J 3.80, 1× thienyl.CH), 6.68 (1H, d, J 8.04, 2-H), 6.61 (1H, d, J 3.84, 1× thienyl.CH), 6.50 (1H, d, J 8.08, 1-H), 5.69 (1H, s, 20-OH), 4.56 (1H, s, 3-OH), 4.42 (1H, s, 5β-H), 3.57 (3H, s, 6-OCH$_3$), 2.94 (1H, d, J 18.56, 10β-H), 2.90 (1H, d, J 6.52, 9α-H), 2.52-2.57 (1H, m, 15/16-NCH$_2$, CH$_2$—), 2.15-2.35 (5H, m, includes 7β-H, 10α-H, 15/16-NCH$_2$, CH$_2$—), 1.77-1.88 (3H, m, 15/16-NCH$_2$, CH$_2$—, 2×18/19-H), 1.76 (3H, s, 20-CH$_3$), 1.59-1.63 (1H, m, 15/16-NCH$_2$, CH$_2$—), 1.00-1.10 (1H, m, 18/19-H), 0.86-0.95 (1H, m, 8α-H), 0.67-0.77 (2H, m, 18/19-H, N—CH$_2$CH(CH$_2$—CH$_2$—)), 0.36-0.47 (2H, m, N—CH$_2$CH(CH$_2$—CH$_2$—)), –0.04-0.06 (2H, m, N—CH$_2$CH(CH$_2$—CH$_2$—)); δ$_C$ (100.56 MHz; CDCl$_3$) 151.81, 146.75, 141.55, 132.47, 129.06, 128.80, 124.93, 122.13, 119.10, 113.84, 96.91, 80.65, 59.52

(NCH$_2$CH(CH$_2$)$_2$), 57.84, 56.76, 52.99, 49.40, 47.00, 43.37 (CH$_2$), 35.90, 35.53 (CH$_2$), 32.59 (CH$_2$), 29.81 (CH$_2$), 23.41, 22.55 (CH$_2$), 17.69 (CH$_2$), 9.27, 4.07 (CH$_2$), 3.25 (CH$_2$). m/z 550 (M$^+$+Na), (Found M$^+$+Na, 550.1774. C$_{29}$H$_{34}$ClNNaO$_4$S requires 550.1795).

Series 1, Scheme 1, R=3-Thienyl (1'S,5α,6R,7R,14α)-1'-(3-thienyl)-1'-(4,5-epoxy-7,8-dihydro-3-hydroxy-6-methoxy-17-cyclopropylmethyl-6,14-ethanomorphinan-7-yl)-ethan-1'-ol (BU11001)

Rf (30% EtOAc.Pet.Ether-0.5% NH$_3$) 0.11. δ$_H$ (400 MHz; CDCl$_3$) 7.26 (1H, d, J 2.96, 1× thienyl.CH), 7.20 (1H, d, J 5.00, 1× thienyl.CH), 7.16 (1H, d, J 2.88, 1× thienyl.CH), 6.68 (1H, d, J 8.04, 2-H), 6.50 (1H, d, J 8.00, 1-H), 5.32 (1H, s, 20-OH), 4.59 (1H, s, 3-OH), 4.46 (1H, s, 5β-H), 3.58 (3H, s, 6-OCH$_3$), 2.93 (1H, d, J 18.40, 10β-H), 2.86 (1H, d, J 6.16, 9α-H), 2.49-2.53 (1H, m, 15/16-NCH$_2$, CH$_2$—), 2.12-2.28 (6H, m, 7β-H, 8β-H, 10α-H, 15/16-NCH$_2$, CH—), 1.81-1.92 (3H, m, 15/16-NCH$_2$, CH$_2$—, 2×18/19-H), 1.79 (3H, s, 20-CH$_3$), 1.58-1.63 (1H, m, 15/16-NCH$_2$, CH$_2$—), 1.04-1.07 (1H, m, 18/19-H), 0.89-0.97 (1H, m, 8α-H), 0.70-0.80 (1H, m, 18/19-H), 0.60-0.70 (1H, m, N—CH$_2$CH(CH$_2$—CH$_2$—)), 0.34-0.45 (2H, m, N—CH$_2$CH(CH$_2$—CH$_2$—)), −0.06-0.03 (2H, m, N—CH$_2$CH(CH$_2$—CH$_2$—)); δ$_C$ (100.56 MHz; CDCl$_3$) 149.44, 137.04, 126.37, 124.94, 120.41, 119.48, 116.18, 97.52, 80.63, 59.47 (NCH$_2$CH(CH$_2$)$_2$), 58.22, 52.67, 48.22, 47.29, 43.33 (CH$_2$), 36.05, 35.57 (CH$_2$), 32.47 (CH$_2$), 29.76 (CH$_2$), 23.90, 22.85 (CH$_2$), 17.79 (CH$_2$), 9.27, 3.79 (CH$_2$), 3.28 (CH$_2$). m/z 494 (M$^+$+1), (Found M$^+$+1,494.2411. C$_{29}$H$_{36}$NO$_4$S requires 494.2365).

Series 2, Scheme 2, R=Ph: (1'R,5α,6R,7R,14α)-1'-phonyl-1'-(4,5-epoxy-7,8-dihydro-3-hydroxy-6-methoxy-17-cyclopropylmethyl-6,14-ethanomorphinan-7-yl)-ethan-1'-ol (BU147)

Using General Procedure A with methylmagnesium bromide on ketone 11 a (R=Ph), followed by General Procedure E or F. White solid. R$_f$=0.5 (MeOH:DCM, 1:10); $^1$H NMR (270 MHz, CDCl$_3$) δ0.10 (2H, m), 0.51 (2H, m), 0.84 (1H, m), 1.55 (3H, s), 2.92 (1H, d), 2.95 (1H, d), 3.41 (3H, s), 4.33 (1H, d), 6.03 (1H, s), 6.41 (1H, d), 6.58 (1H, d), 7.25 (3 h, m), 7.55 (2H, m); $^{13}$C NMR (68 MHz, CDCl$_3$) δ 3.90, 4.12, 9.73, 15.72, 22.97, 29.15, 31.02, 31.28, 35.80, 36.09, 43.98, 47.01, 49.94, 52.73, 59.02, 60.39, 80.86, 98.33, 116.73, 119.67, 126.90, 126.98, 127.70, 128.48, 132.79, 137.81, 145.98, 146.56. HRMS (EI) calcd for C$_{31}$H$_{44}$NO$_4$ (M$^+$), 487.2723; found 487.2323.

Series 2, R=2-pyridyl: (1'R,5α,6R,7R,14α)-1'-(2-pyridyl)-1'-(4,5-epoxy-7,8-dihydro-3-hydroxy-6-methoxy-17-cyclopropylmethyl-6,14-ethanomorphinan-7-yl)-ethan-1'-ol (BU11005)

2-Bromopyridine (0.11 ml, 0.1.13 mmol) was taken in dry diethylether and solution was cooled to −78° C. with dry ice under nitrogen atmosphere. Thereafter a solution of n-butyllithium (1.13 mmol) was dropwise added to it. The reaction mixture was stirred for 10 min. then 5a dissolved in dry THF was added to it. The reaction mixture was allowed to warm to room temperature and stirred for 20 h. After completion, the reaction mixture was quenched with saturated ammonium chloride solution (aqueous) and extracted with ethylacetate. Organic layer was washed with brine, dried over sodium sulfate and vacuum evaporated to obtained crude product which was purified by flash chromatography using methanol:dichloromethane (0.5:99.5).

White Solid; $^1$H NMR (CDCl$_3$) δ 0.08-0.11 (2H, m), 0.40-0.51 (2H, m), 0.80-0.88 (2H, m), 1.20-1.27 (2H, m), 1.62 (1H, d, J=2.68 Hz), 1.67 (3H, s), 2.02-2.41 (8H, m), 2.61 (1H, dd, J=11.72, J=5.12 Hz), 2.78 (1H, dt, J=12.16, J=3.92 Hz), 2.91 (1H, d, J=18.24 Hz), 3.02 (1H, d, J=6.40 Hz), 3.35 (3H, s), 4.39 (1H, s), 4.55 (1H, bd), 5.83 (1H, s), 6.43 (1H, d, J=8.0 Hz), 6.61 (1H, d, J=8.0 Hz), 7.10-7.14 (1H, m), 7.62-7.64 (2H, m), 8.48 (1H, d, J=4.76 Hz), $^{13}$C NMR, 400 MHz, (CDCl$_3$) δ 3.21, 4.33, 9.35, 16.42, 22.45, 28.39, 28.86, 29.92, 35.24, 35.65, 43.81, 46.78, 49.36, 52.28, 57.95, 59.89, 80.1, 97.70, 116.01, 119.37, 120.54, 121.55, 128.54, 132.45, 135.78, 136.93, 145.30, 147.32, 166.46; HRMS, m/z for (C$_{30}$H$_{36}$N$_2$O$_4$), [MH]$^+$: calcd 489.2753, found—489.2821.

Series 2, R=4-pyridyl: (1'R,5α,6R,7R,14α)-1'-(4-pyridyl)-1'-(4,5-epoxy-7,8-dihydro-3-hydroxy-6-methoxy-17-cyclopropylmethyl-6,14-ethanomorphinan-7-yl)-ethan-1'-ol (BU1006)

4-Bromopyridine (0.11 ml, 0.1.13 mmol) was taken in dry diethylether and solution was cooled to −78° C. with dry ice under nitrogen atmosphere. Thereafter a solution of n-butyllithium (1.13 mmol) was dropwise added to it. The reaction mixture was stirred for 10 min. then 5a dissolved in dry THF was added to it. The reaction mixture was allowed to warm to room temperature and stirred for 20 h. After completion, the reaction mixture was quenched with saturated ammonium chloride solution (aqueous) and extracted with ethylacetate. Organic layer was washed with brine, dried over sodium sulfate and vacuum evaporated to obtained crude product which was purified by flash chromatography using methanol:dichloromethane (0.5:99.5).

White Solid; $^1$H NMR (CDCl$_3$) δ 0.10-0.12 (2H, m), 0.24-0.55 (5H, m), 0.82-0.84 (1H, m), 1.49 (1H, dd, J=12.88, J=9.04 Hz), 1.58 (3H, s), 1.65 (1H, dd, J=12.92, J=5.60 Hz), 2.01-2.40 (7H, m), 2.62-2.68 (2H, m), 2.92-3.01 (3H, m), 3.41 (3H, s), 4.33 (1H, s), 6.06 (1H, s), 6.43 (1H, d, J=8.0 Hz), 6.63 (1H, d, J=8.0 Hz), 7.48 (2H, d, J=6.16 Hz), 8.52 (2H, d, J=6.16 Hz); $^{13}$C NMR, 400 MHz, (CDCl$_3$) δ 3.47, 4.11, 9.38, 15.58, 22.49, 28.52 29.22, 31.02, 35.33, 35.66, 36.80, 43.60, 46.75, 49.50, 52.61, 58.24, 59.92, 80.35, 97.62, 116.53, 119.50, 121.97, 127.87, 131.92, 137.41, 145.45, 148.76, 149.21, 155.79; HRMS, m/z for (C$_{30}$H$_{36}$N$_2$O$_4$), [MH]$^+$: calcd 489.2753, found—489.2756.

Series 3, Scheme 2, R=Ph: (1'S,5α,6R,7R,14α)-1'-phenyl-1'-(4,5-epoxy-7,8-dihydro-3-hydroxy-6-methoxy-17-cyclopropylmethyl-6,14-ethanomorphinan-7-yl)-methan-1'-ol (BU126)

From reduction of 11a (R=Ph) followed by general procedure E or F.

$^1$H NMR (CDCl$_3$) δ−0.04-0.06 (2H, m), 0.45 (2H, m), 0.7 (1H, m), 2.93 (1H, d, J 18.5), 3.07 (1H, d, J 6.3), 3.48 (3H, s), 4.46 (1H, d, J 1.8), 5.28 (1H, s), 6.50 (1H, d, J 8.1), 6.68 (1H, d, J 8.1), 7.26-7.40 (5H, m); $^{13}$C NMR (CDCl$_3$) δ 3.36, 4.17, 9.32, 20.6, 22.7, 25.6, 29.1, 35.3, 35.9, 42.1, 43.8, 46.1, 50.6, 58.5, 59.9, 70.1, 77.3, 92.3, 116.6, 119.5, 125.7, 127.0, 128.2, 128.3, 132.6, 137.4, 145.0, 145.5; m/z 473.

13b, Scheme 2, R=Phenyl: (1'S,5α,6R,7R,14α)-1'-phenyl-1'-(4,5-epoxy-7,8-dihydro-3-hydroxy-6-methoxy-17-cyclopropylmethyl-6,14-ethenomorphinan-7-yl)-methan-1'-ol (BU125)

From the treatment of 11b (R=Ph) as per General Procedure D, followed by General Procedure E or F.

NMR (CDCl$_3$) δ 0.4 (2H, m), 0.45 (2H, m), 0.65 (1H, m), 3.01 (1H, d, J 18.7), 3.35 (1H, d, J 6.7), 3.80 (3H, s), 4.35 (1H, d, J 9.0), 4.65 (1H, d, J 1.3), 5.43 (1H, s), 5.56 (1H, d, J 8.9), 6.00 (1H, d, J 9.0), 6.43 (1H, d, J 8.1), 6.55 (1H, d, J 8.1), 7.28 (5H, m); $^{13}$C NMR (CDCl$_3$) δ 3.5, 4.0, 9.2, 23.0, 30.4, 33.0, 42.6, 43.8, 43.9, 47.8, 54.9, 57.0, 59.9, 77.7, 84.5, 97.8, 116.3, 119.8, 124.4, 125.8, 127.7, 128.1, 128.2, 134.3, 137.5, 137.8, 141.7, 146.3; m/z 471.

Series 4, Scheme 2, R=Ph: (1'R,5α,6R,7R,14α)-1'-phenyl-1'-(4,5-epoxy-7,8-dihydro-3-hydroxy-6-methoxy-17-cyclopropylmethyl-6,14-ethanomorphinan-7-yl)-methan-1'-ol (BU106)

As the major product of phenylmagnesium bromide addition to aldehyde 8 (General procedure A) followed by General Procedure E or F. White solid. R$_f$=0.48 (Hexane:EtOAc, 1:1, 0.5% NH4OH), $^1$H NMR (270 MHz, CDCl$_3$) δ 0.05 (2H, m), 0.45 (2H, m), 0.71 (1H, m), 2.93 (1H, d), 3.07 (1H, d), 3.48 (3H, s), 4.46 (1H, d), 5.28 (1H, s), 6.50 (1H, d), 6.68 (1H, d), 7.26-7.40 (2H, m), 7.36-7.43 (3H, m). $^{13}$C NMR (68 MHz, CDCl$_3$) δ 3.4, 4.2, 9.4, 20.4, 22.6, 25.7, 29.3, 35.5, 35.8, 42.5, 43.8, 46.0, 51.0, 56.6, 58.5, 59.9, 70.1, 77.3, 92.3, 116.6, 119.5, 125.7, 127.0, 128.2, 128.3, 132.6, 137.4, 145.0, 145.5. HRMS (ES) calcd for C$_{31}$H$_{44}$NO$_4$ (M$^+$), 473.2566; found 473.2558.

N-Cyclopropylcarbonyl-7α-formyl-7β-methyl-6,14-endo-ethenotetrahydronorthebaine (17b)

To a suspension of 13.61 g (37.29 mmol) N-CPCnorthebaine (16) in 20 mL of methacrolein was added 3.49 g of LiBF$_4$. The resulting solution was stirred for 16 h at RT. Into this solution were added 30 mL of CH$_2$Cl$_2$ and the mixture was extracted with water (10 mL×3) and brine (5 mL). The solution was dried, filtered and removed of solvent on a rotary evaporator to afford a dark red syrup. This material was subjected to silica gel flash column chromatography eluting with 50% EtOAc in petroleum ether to afford 5.91 g of the faster running component 17a (N-Cyclopropylcarbonyl-7β-formyl-7α-methyl-6,14-endo-ethenotetrahydronorthebaine) as white solid $^1$H NMR (CDCl$_3$) δ 9.85 (s, 1H); 6.67 (d, 1H, J=6 Hz); 6.57 (d, 1H, J=6 Hz); 6.14-6.07 (2d, 1H); 5.57 (d, 1H, J=9 Hz); 5.33 (d, 1H, J=6 Hz); 4.76 (d, 1H, 0.4H); 4.57-4.53 (m, 1.6H); 4.15-4.10 (m, 1H); 3.85 (s, 3H); 3.72 (s, 3H); 3.42 (dt, 1H, J$_a$=9 Hz, J$_b$=3 Hz); 3.11-3.05 (dd, 1H, J$_a$=6 Hz, J$_b$=3 Hz); 2.88-2.83 (m, 2H); 2.43-2.35 (dt, 1H, J$_a$=9 Hz, J$_b$=6 Hz); 1.85-1.76 (m, 1H); 1.69-1.65 (m, 1H); 1.09-1.03 (m, 5H); 0.91-0.76 (m, 2H). ESIMS: m/z 436 (M+H$^+$, 100) and 4.11 g of a slower running component N-Cyclopropylcarbonyl-7α-formyl-7β-methyl-,6, 14-endo-ethenotetrahydronorthebaine (17b) as a white solid. $^1$H NMR (CDCl$_3$) δ 9.54 (s, 0.5H); 9.45 (s, 0.5H); 6.69 (d, 1H, J=6 Hz); 6.59 (d, 1H, J =6 Hz); 6.14 (t, 1H); 5.57 (dd, 1H, J$_n$=9 Hz, J$_b$=6 Hz); 5.35 (d, 0.5H, J=3 Hz); 4.93 (s, 1H); 4.80 (d, 0.5H, J=6 Hz); 4.64 (dd, 1H, J$_a$=6 Hz, J$_b$=3 Hz); 4.15 (dd, 1H, J$_a$=6 Hz, J$_b$=3 Hz); 3.85 (s, 3H); 3.72 (2s, 3H); 3.49 (dt, 1H); 3.21-3.31 (m, 2H), 2.37-2.26 (dt, 0.5H), 2.27-2.15 (dt, 0.5H); 2.06-1.72 (m, 3H); 1.35 (s, 3H); 1.08 (m, 2H); 0.82 (m, 2H). At RT the $^1$H NMR spectra of this compound in d$_6$-DMSO has two signals at δ 9.408 (s, 0.5H) and δ 9.375 (s, 0.5H) which coalesce when running the $^1$H NMR experiment at 360° K. ESIMS: m/z 436 (M+H$^+$, 100).

N-Cyclopropylcarbonyl-6,14-endo-etheno-7β-methyl-nornepenthol (18)

General procedure B was followed using 500 mg of 17b to yield 442 mg of 18 as a white solid: $^1$H NMR (CDCl$_3$) δ 7.26-7.19 (m, 5H); 6.68-6.63 (2d, 1H); 6.55-6.49 (2d, 1H); 6.19 (d, 0.55H, J=9 Hz); 5.98 (d, 0.45H, J=6 Hz); 5.41 (d, 0.55H, J=9 Hz); 5.29-5.22 (m, 1H); 5.01 (s, 1H), 4.80 (d, 1H, J=3 Hz); 4.66-4.53 (m, 1H); 4.12 (dd, 0.45H, J=3 Hz, J=6 Hz); 3.84 (2s, 3H); 3.72 (2s, 3H); 3.49-3.39 (m, 0.45H); 3.20-3.11 (dd, 0.55H, J=3 Hz, J=6 Hz); 3.08-2.89 (m, 2H); 2.82-2.78, (d, 0.55H); 2.46 (d, 0.45H); 2.39 (dt, 0.45H); 2.24 (dt, 0.55H); 2.10 (d, 0.55H, J=9 Hz); 2.03 (d, 0.45H, J=9 Hz); 1.89-1.69 (m, 3H); 1.27 (s, 1.35H); 1.12 (s, 1.65H); 1.10-0.91 (m, 2H); 0.88-0.78 (m, 2H). ESIMS: m/z 514 (M+H$^+$, 100).

N-Cyclopropylmethyl-6,14-endo-etheno-7β-methyl-norisonepenthol (20: R=Ph)

General procedures C and D were followed using 439 mg of 18 to yield, after chromatography, 201 mg of the faster eluting component 20a as a colorless oil $^1$H NMR (CDCl$_3$) δ 7.29-7.20 (m, 5H); 6.64 (d, 1H, J=6 Hz); 6.50 (d, 1H, J=6 Hz); 6.20 (dd, 1H, J$_a$=6 Hz, J$_b$=3 Hz); 5.58 (d, 1H, J=6 Hz); 5.28 (s, 1H); 5.08 (s, 1H); 4.69 (s, 1H); 3.85 (s, 6H); 3.40 (d, 1H, J=6 Hz); 3.07 (d, 1H, J=15 Hz); 2.66 (m, 1H); 2.39 (dd, 1H, J$_a$=6 Hz, J$_b$=15 Hz); 2.35-2.22 (m, 4H); 2.01 (d, 1H, J=12 Hz); 1.75-1.71 (m, 1H); 1.53 (s, 1H); 1.41 (s, 3H); 1.32-1.28 (d, 1H, J=12 Hz); 0.73-0.68 (m, 1H); 0.52-0.42 (m, 2H); 0.09-0.02 (m, 2H). ESIMS: m/z 500 (M+H$^+$, 100).

N-Cyclopropylmethyl-6,14-endo-etheno-7β-methyl-nornepenthol (21: R=Ph)

General procedure D was followed using 439 mg of 18 to yield, after chromatography, 139 mg of the slower eluting component 21 as a colourless oil $^1$H NMR (CDCl$_3$) δ 7.29-7.17 (m, 5H); 6.59 (d, 1H, J=6 Hz); 6.46 (d, 1H, J=6 Hz); 6.02 (d, 1H, J=6 Hz); 5.35 (d, 1H, J=6 Hz); 5.01 (s, 1H); 4.78 (s, 1H); 3.82 (s, 3H); 3.70 (s, 3H); 3.52 (d, 1H, J=3 Hz); 3.08 (d, 1H, J=15 Hz); 2.78-2.68 (m, 2H); 2.44-2.25 (m, 6H); 1.94 (d, 1H, J=12 Hz); 1.75-1.72 (m, 1H); 1.21 (s, 3H) 0.85 (m, 1H); 0.54 (m, 2H); 0.14 (m, 2H). ESIMS: m/z 500 (M+H$^+$, 100).

22, R=Ph: (1'R,5α,6R,7R,14α)-1'-phenyl-1'-(4,5-epoxy-7,8-dihydro-3-hydroxy-6-methoxy-7β-methyl 17-cyclopropylmethyl-6,14-etheno-morphinan-7-yl)-methan-1'-ol (BU128)

General procedure E or F was followed using 184 mg of 20 to yield 103 mg of 22 as a white solid: $^1$H NMR (CD$_3$OD) δ 7.37 (d, 1H, J=6 Hz); 7.32-7.23 (m, 3H); 6.62 (d (AB system), 1H); 6.56 (d (AB system), 1H); 6.22 (d, 1H, J=6 Hz); 5.61 (d, 1H, J=9 Hz); 5.22 (s, 1H), 4.47 (s, 1H); 4.35 (d, 1H, J=6 Hz); 3.86 (s, 3H); 3.40-3.30 (m, 3H); 3.15 (dt, 1H, J$_a$=9 Hz, J$_b$=3 Hz); 3.09-2.97 (m, 2H); 2.47 (dt, 1H, J$_b$=9 Hz, J$_a$=3 Hz); 2.10 (dd, 1H, J$_a$=12 Hz, J$_b$=3 Hz); 1.87 (d (AB system), 1H); 1.67 (d, (AB system), 1H); 1.50 (s, 3H); 1.07 (m, 1H); 0.83 (m, 1H); 0.74 (m, 1H); 0.51-0.43 (m, 2H). ESIMS: m/z 486 (M+H$^+$, 100).

23, R=Ph: (1'S,5α,6R,7R,14α)-1'-phenyl-1'-(4,5-epoxy-7,8-dihydro-3-hydroxy-6-methoxy-7β-methyl 17-cyclopropylmethyl-6,14-etheno-morphinan-7-yl)-methan-1'-ol (BU129)

General procedure E or F was followed using 161 mg of 21 to yield 56 mg of 23 as a white solid: $^1$H NMR (CD$_3$OD) δ 7.30-7.18 (m, 5H); 6.59 (AB system, 2H); 6.31 (d, 1H, J=6.7 Hz); 5.51 (d, 1H, J=6.7 Hz); 5.02 (s, 1H); 4.66 (s, 1H); 4.45 (d, 1H, J=5.1 Hz); 3.50-3.40 (m, 3H); 3.38-3.32 (m, 1H); 3.20 (dt, 1H, J$_a$=10.5 Hz, J$_b$=7.3 Hz); 3.16-3.04 (m, 2H); 2.53 (dt, 1H, $J_a$=11.0 Hz, $J_b$=3.9 Hz); 2.16 (AB system, 2H); 2.11 (dd, 1H); 1.28 (s, 3H); 1.21-1.13 (m, 1H); 0.92-0.84 (m, 1H); 0.84-77 (m, 1H); 0.57 (m, 2H). ESIMS: m/z 486 (M+H$^+$, 100).

By a similar method, the following ligands were prepared:

22, R=o-tolyl: (1'R,5α,6R,7R,14α)-1'-(2-methylphenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10111)

$^1$H NMR (CD$_3$OD) δ 7.65 (d, 1H, J=5.5 Hz); 7.25-7.15 (m, 3H); 6.67-6.47 (AB system, 2H); 5.80 (d, 1H, J=6.7 Hz); 5.26 (s, 1H), 5.08 (s, 1H); 4.23 (d, 1H, J=4.8 Hz); 3.94 (s, 3H); 3.43-3.33 (m, 3H); 3.12 (m, 1H); 3.03-2.83 (m, 2H); 2.52 (dt, 1H, $J_b$=10.3 Hz, $J_a$=4.1 Hz); 2.27 (s, 3H); 2.16-2.04 (bd, 1H); 1.95 (d, 1H, J=10.2 Hz); 1.61 (s, 3H); 1.23 (d, 1H, J=10.2 Hz); 1.07 (m, 1H); 0.82 (m, 1H); 0.72 (m, 1H); 0.49-0.37 (m, 2H). ESIMS: m/z 500 (M+H$^+$, 100).

23, R=o-tolyl (1'S,5α,6R,7R,14α)-1'-(2-methylphenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10121)

$^1$H NMR (CD$_3$OD) δ 7.16 (d, 2H, J=6.0 Hz); 7.08 (d, 2H, J=6.0 Hz); 6.59 (d, 1H, J=6.1 Hz); 6.54 (d, 1H, J=6.1 Hz); 6.29 (d, 1H, J=6.5 Hz); 5.49 (s, 1H, J=6.8 Hz); 5.02 (s, 1H); 4.63 (s, 1H); 4.45 (bd, 1H); 3.47 (s, 3H); 3.46-3.31 (m, 2H); 3.32-3.06 (m, 3H); 2.52 (dt, 1H, $J_a$=13.8 Hz, $J_b$=3.8 Hz); 2.30 (s, 3H); 2.14 (s, 2H); 2.10-2.06 (m, 1H); 1.24 (s, 3H); 1.18 (m, 1H); 0.89-0.78 (m, 2H); 0.51 (m, 2H). ESIMS: m/z 500 (M+H$^+$, 100).

22, R=m-totyl: (1'R,5α,6R,7R,14α)-1'-(3-methylphenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10112)

$^1$H NMR (CD$_3$OD) δ 7.45 (d, 1H, J=5.6 Hz); 7.18-7.13 (m, 3H); 6.64-6.57 (AB system, 2H); 6.33 (d, 1H, J=6.7 Hz); 5.54 (d, 1H, J=6.7 Hz); 5.35 (s, 1H), 5.11 (s, 1H); 4.52 (d, 1H, J=5.1 Hz); 3.72 (s, 3H); 3.51-3.32 (m, 3H); 3.29-3.20 (dt, 1H, $J_b$=9.8 Hz, $J_a$=3.1 Hz); 3.17-3.09 (m, 2H); 2.59 (dt, 1H, $J_b$=10.3 Hz, $J_a$=4.1 Hz); 2.45 (d, 1H, J=11.1 Hz); 2.39 (s, 3H); 2.22 (d, 1H, J=11.1 Hz); 2.11 (bd, 1H); 1.23 (m, 1H); 1.11 (s, 3H); 0.92-0.85 (m, 2H); 0.57 (m, 1H). ESIMS: m/z 500 (M+H$^+$, 100).

23, R=m-tolyl: (1'S,5α,6R,7R,14α)-1'-(3-methylphenyl)-1'-(4,5-epoxy-7,8-dihydro-3-hydroxy-6-methoxy-7β-methy 17β-cyclopropylmethyl-6,14-etheno-morphinan-7-yl)-methan-1'-ol (BU10113)

$^1$H NMR (CD$_3$OD) δ 7.17-7.06 (m, 3H); 6.59 (d, 1H, J=6.0 Hz); 6.54 (d, 1H, J=6.0 Hz); 6.31 (d, 1H, J=6.9 Hz); 5.50 (d, 1H, J=6.6 Hz); 5.02 (s, 1H, J=6.8 Hz); 4.64 (s, 1H); 4.44 (bd, 1H); 3.45 (s, 3H); 3.46-3.31 (m, 2H); 3.23-3.05 (m, 3H); 2.52 (dt, 1H, $J_a$=11.7 Hz, $J_b$=4.4 Hz); 2.32 (s, 3H); 2.11 (m, 2H); 1.25 (s, 3H); 1.18 (m, 1H); 0.93-0.77 (m, 2H); 0.53 (m, 2H). ESIMS: m/z 500 (M+H$^+$, 100).

22, R=p-tolyl: (1'R,5α,6R,7R,14α)-1'-(4-methylphenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10117)

$^1$H NMR (CD$_3$OD) δ 7.25 (d, 1H, J=6.0 Hz); 7.12 (d, 1H, J=5.7 Hz); 6.59 (AB system, 2H); 6.23 (d, 1H, J=6.6 Hz); 5.62 (d, 1H, J=6.6 Hz); 5.21 (s, 1H), 4.69 (s, 1H); 4.34 (d, 1H, J=4.8 Hz); 3.87 (s, 3H); 3.40-3.32 (m, 3H); 3.14 (dt, $J_a$=9.9 Hz, $J_a$=1.8 Hz); 3.12-2.99 (m, 2H); 2.48 (dt, 1H, $J_a$=10.8 Hz); 2.30 (s, 3H); 2.10 (dd, $J_a$=10.8 Hz, $J_b$=2.4 Hz); 1.87 (d, AB system, 1H); 1.64 (d, AB system, 1H); 1.50 (s, 3H); 1.07 (m, 1H); 0.83 (m, 1H); 0.74 (m, 1H); 0.52-0.40 (m, 2H). ESIMS: m/z 500 (M+H$^+$, 100).

23, R=p-tolyl: (1'S,5α,6R,7R,14α)-1'-(4-methylphenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10099)

$^1$H NMR (CD$_3$OD) δ 7.16 (d, 2H, J=6.0 Hz); 7.08 (d, 2H, J=6.0 Hz); 6.59 (d, 1H, J=6.1 Hz); 6.54 (d, 1H, J=6.1 Hz); 6.29 (d, 1H, J=6.5 Hz); 5.49 (s, 1H, J=6.8 Hz); 5.02 (s, 1H); 4.63 (s, 1H); 4.45 (bd, 1H); 3.47 (s, 3H); 3.46-3.31 (m, 2H); 3.32-3.06 (m, 3H); 2.52 (dt, 1H, $J_a$=13.8 Hz, $J_b$=3.8 Hz); 2.30 (s, 3H); 2.14 (s, 2H); 2.10-2.06 (m, 1H); 1.24 (s, 3H); 1.18 (m, 1H); 0.89-0.78 (m, 2H); 0.51 (m, 2H). ESIMS: m/z 500 (M+H$^+$, 100).

22, R=p-fluorophenyl: (1'R,5α,6R,7R,14α)-1'-(4-fluorophenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10120)

$^1$H NMR (maleate) (400 MHz, CDCl$_3$) δ 0.40-0.49 (2H, m), 0.72-0.84 (2H, m), 1.00-1.12 (1H, m) 1.48 (3H, s), 1.61 (1H, d, J=13.6 Hz), 1.88 (1H, d, J=13.2 Hz), 2.08 (1H, d, J=14.4 Hz), 2.46 (1H, td, J=14.1, 4.9 Hz), 2.93-3.15 (3H, m), 3.85 (3H, s), 4.29 (1H, s), 5.20 (1H, s), 5.58 (1H, d, J=8.0 Hz), 6.16 (1H, d, J=8.0 Hz), 6.24 (2H, s), 6.54 (1H, d, J=8.0 Hz), 6.61 (1H, d, J=8.4 Hz), 7.01-7.05 (2H, m), 7.36-7.38 (2H, m).

23, R=p-fluorophenyl: (1'S,5α,6R,7R,14α)-1'-(4-fluorophenyl)-1'-(4,5-epoxy-7,8-dihydro-3-hydroxy-6-methoxy-7β-methyl 17-cyclopropylmethyl-6,14-etheno-morphinan-7-yl)-methan-1'-ol (BU10118)

$^1$H NMR (maleate) (CD$_3$OD) δ 7.31-7.27 (m, 2H); 7.01-6.96 (m, 2H); 6.59 (d, 1H, J=6.0 Hz); 6.55 (d, 1H, J=6.0 Hz); 6.31 (d, 1H, J=6.7 Hz); 5.53 (d, 1H, J=6.9 Hz); 5.00 (s, 1H); 4.63 (s, 1H); 4.45 (d, 1H, J=5.1 Hz); 3.48-3.28 (m, 5H); 3.24 (dt, 2H, $J_a$=10.2 Hz, $J_b$=3.3 Hz); 3.11 (d, (d, 1H, J=5.4 Hz); 3.07 (t, J=5.4 Hz); 2.53 (dt, 1H, $J_a$=10.5 Hz, $J_b$=3.9 Hz); 2.21 (d, 1H, J=9.9 Hz); 2.12-2.06 (m, 2H); 1.29 (s, 3H); 1.17 (m, 1H); 0.93-0.78 (m, 2H); 0.53 (m, 2H). ESIMS: m/z 504 (M+H, 100).

22, R=4-PrSPh (1'R,5α,6R,7R,14α)-1'-(4-propylthiophenyl)-1'-(4,5-epoxy-7,8-dihydro-3-hydroxy-6-methoxy-7β-methy 17-cyclopropylmethyl-6,14-etheno-morphinan-7-yl)-methan-1'-ol (BU11020)

$^1$H NMR (maleate) (400 MHz, CDCl$_3$) δ 0.38-0.51 (2H, m), 0.70-0.89 (2H, m), 1.01 (3H, t, J=7.1 Hz), 1.03-1.12 (1H, m), 1.44-1.51 (4H, m), 1.59-164 (3H, m), 1.87 (1H, d, J=13.0 Hz), 2.10 (1H, dd, J=14.8, 3.7 Hz), 2.47 (1H, td, J=13.9, 4.9 Hz), 2.89 (2H, t, J=6.8 Hz), 2.98-3.18 (3H, m), 3.32-3.40 (3H, m), 3.85 (3H, s), 4.34 (1H, d, J =7.2 Hz), 4.68 (1H, s), 5.21 (1H, s), 5.60 (1H, d, J=9.0 Hz), 6.20 (1H, d, J=8.9 Hz), 6.26 (2H, s), 6.56 (1H, d, J=8.1 Hz), 6.61 (1H, d, J=8.1 Hz), 7.25-7.30 (4H, m).

N-Cyclopropylcarbonyl-7α-formyl-7β-methyl-6,14-endo-ethanotetrahydronorthebaine (24)

The aldehyde 17b (500 mg) was dissolved in 15 mL of EtOH. Into this solution was added 30 mg of 10% Pd on carbon. The mixture was shaken in a Parr hydrogenator under 100 psi of $H_2$ for 12 h. The mixture was filtered and the solvents removed under reduced pressure to yield 510 mg of 24 as a white solid.

$^1$H NMR (CDCl$_3$) δ 9.69 (2s, 1H); 6.77 (d, 1H, J=6.1 Hz); 6.61 (d, 1H, J=6.1 Hz); 4.91 (d, 0.47H, J=4.9 Hz); 4.83 (2s, 1H); 4.52 (dd, 0.53H, J=10.6 Hz); 4.35 (d, 0.53H, J=5.2 Hz); 4.08-4.03 (m, 1H); 3.90 (s, 3H); 3.46 (2s, 3H); 3.39-3.30 (m, 0.47H); 3.08-2.95 (m, 1H); 2.90-2.69 (m, 2H); 2.41 (m, 1H); 2.28 (dt, 0.47H); 2.17 (dt, 0.53H); 1.70-1.60 (m, 4H); 1.31 (s, 3H); 1.19-1.1 (m, 1H); 1.01 (m, 2H); 0.77 (m, 2H). ESIMS: m/z 438 (M+H$^+$, 100).

N-Cyclopropylcarbonyl-6,14-endo-ethano-7β-methyl-nornepenthol (25)

General procedure B was followed using 515 mg of 24 to yield 336 mg of 25 as white crystals:

$^1$H NMR (CDCl$_3$) δ 7.36-7.23 (m, 5H); 6.78-6.75 (2d, 1H); 6.61-6.58 (2d, 1H); 5.06 (d, 0.55H, J=2.0 Hz); 4.99 (d, 0.45H, J=2.0 Hz); 4.91-4.87 (m, 1H); 4.51-4.46 (dd, 0.55H, J$_a$=4.1 Hz, Jb=10.3 Hz); 4.35-4.34 (d, 0.55H, J=5.1 Hz); 4.03-3.98 (d, 0.45H, J$_a$=3.7 Hz, J$_b$=10.2 Hz); 3.92-3.914 (2s, 3H); 3.53 (s, 1.65H); 3.48 (s, 1.35H); 3.38-3.30 (dt, 0.55H, J$_a$=2.9 Hz, J$_b$=6.5 Hz); 3.11-3.04 (dd, 0.55H, J$_a$=5.2 Hz, J$_b$=13.8 Hz); 3.02-2.96 (dd, 0.45H, J$_a$=5.2 Hz, J$_b$=13.9 Hz); 2.92-2.88 (d, 0.55H, J=13.8 Hz); 2.49-2.44 (m, 1H); 2.36-2.29 (dt, 0.45 Hz, J$_a$=4.2 Hz, J$_b$=9.7 Hz); 2.25-2.17 (dt, 0.55 Hz, J$_a$=4.5 Hz, J$_b$=9.9 Hz); 2.03-1.90 (m, 2H); 1.86-1.80 (m, 0.55 Hz); 1.76-1.51 (m, 5.45H); 1.10-0.69 (m, 7H).
ESIMS: m/z 516 (M+H$^+$, 100).

(1'R,5α,6R,7R,14α)-1'-phenyl-1'-(4,5-epoxy-7,8-dihydro-3,6-dimethoxy-7β-methyl 17-cyclopropylmethyl-6,14-etheno-morphinan-7-yl)-methan-1'-ol (28: R=Ph)

General procedures C and D were followed using 473 mg of 25 to yield a clear residue after extraction. Crystallization from CH$_2$Cl$_2$/Et$_2$O gave 133 mg of 28 as white crystals $^1$H NMR (CDCl$_3$) δ 7.45 (m, 2H); 7.34-7.30 (m, 2H); 7.27-7.24 (m, 1H); 6.73 (d, 1H, J=6.3 Hz); 6.57 (d, 1H, J=6.0 Hz); 5.76 (s, 1H); 5.03 (s, 1H); 4.96 (s, 1H); 3.91 (s, 3H); 3.64 (s, 3H); 3.01-2.94 (m, 2H); 2.57 (d, 1H, J=5.1 Hz); 2.29 (dd, 1H, J$_a$=5.1 Hz, J$_b$=13.8 Hz); 2.24-2.20 (m, 3H); 1.95 (dd, 1H, J$_a$=3 Hz, J$_b$=10.8 Hz); 1.90-1.77 (m, 2H); 1.60-1.52 (m, 2H); 1.40-1.28 (m, 4H); 0.95 (m, 1H); 0.68 (m, 1H); 0.51-0.39 (m, 2H); 0.08-0.01 (m, 2H). ESIMS: m/z 502 (M+H$^+$, 100).

(1'S,5α,6R,7R,14α)-1'-phenyl-1'-(4,5-epoxy-7,8-dihydro-3-hydroxy-6-methoxy-7β-methyl 17-cyclopropylmethyl-6,14-ethanomorphinan-7-yl)-methan-1'-ol (29: R=Ph) (BU10122)

General procedure E or F was followed using 27 to yield 29 as a white solid:

$^1$H NMR (400 MHz, CDCl$_3$) δ 0.47-0.53 (2H, m), 0.77-0.89 (3H, m), 0.92 (3H, s), 1.12-1.20 (1H, m), 1.62-1.70 (1H, m), 1.79-1.90 (2H, m), 2.00 (1H, dd, J=12.6, 4.2 Hz), 2.15 (1H, t, J=12.2 Hz), 2.50 (1H, td, J=13.8, 5.6 Hz), 2.67 (1H, d, J=12.8 Hz), 2.95 (1H, dd, J=19.4, 7.0 Hz), 3.00-3.12 (2H, m), 3.22-3.39 (3H, m), 3.47 (3H, s), 4.00 (1H, d, J=7.2 Hz), 4.95 (1H, d, J=2.4 Hz), 5.02 (1H, s), 6.64 (1H, d, J=8.0 Hz), 6.74 (1H, d, J=8.4 Hz), 7.21-7.25 (1H, m), 7.27-7.31 (2H, m), 7.36-7.38 (2H, m). HMRS: calc for [C$_{31}$H$_{36}$N$_1$O$_4$]$^+$ ([M+H]$^+$) 488.2796, found 488.2949.

(1'R,5α,6R,7R,14α)-1'-phenyl-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=Ph) (BU10119).

General procedure E or F was followed using 133 mg of 28 to yield 75 mg of 30 as a white solid:

$^1$H NMR (CD$_3$OD) δ 7.55 (d, 2H); 7.38-7.34 (m, 2H); 7.31-7.27 (m, 1H); 6.77 (d, 1H, J=6.0 Hz); 6.67 (d, 1H, J=6.0 Hz); 5.11 (s, 2H); 3.93 (d, 1H, J=5.4 Hz); 3.27-3.18 (m, 2H); 3.6-2.91 (m, 3H); 2.41 (dt, 1H, J$_a$=10.5 Hz, J$_b$=4.2 Hz); 1.95-1.90 (m, 1H); 1.77 (dd, 1H, J$_a$=10.2 Hz, J$_b$=3.3 Hz); 1.66-1.58 (m, 1H); 1.38 (s, 3H); 1.05-1.01 (m, 1H); 0.80 (m, 1H); 0.72 (m, 1H); 0.4-0.34 (m, 2H). ESIMS: m/z 488 (M+H$^+$, 100).

By a similar method the following compounds were prepared:

(1'R,5α,6R,7R,14α)-1'-(2-methylphenyl)-1'-(4,5-epoxy-7,8-dihydro-3-hydroxy-6-methoxy-7β-methyl 7-cyclopropylmethyl-6,14-ethanomorphinan-7-yl)-methan-1'-ol (30: R=2-MePh) (BU12004)

$^1$H NMR (400 MHz, CDCl$_3$) δ (−0.02)-0.07 (2H, m), 0.38-0.48 (2H, m), 0.62-0.71 (1H, m), 0.83-0.95 (1H, m), 1.25 (1H, d, J=14.3 Hz), 1.33-1.43 (4H, m), 1.56 (1H, d, J=10.1 Hz), 1.83-1.87 (2H, m), 1.99 (1H, dd, J=14.3, 3.9 Hz), 2.18-2.31 (5H, m), 2.47 (3H, s), 2.57-2.61 (1H, m), 2.93 (1H, d, J=6.5 Hz), 2.94 (1H, d, J=18.1 Hz), 3.61 (3H, s), 4.83 (1H, bs), 5.04 (1H, s), 5.47 (1H, s), 5.49 (1H, s), 6.52 (1H, d, J=8.0 Hz), 6.69 (1H, d, J=8.0 Hz), 7.13 (1H, dd, J=7.5, 1.7 Hz), 7.17 (1H, td, J=7.3, 1.5 Hz), 7.22 (1H, td, J=7.4, 1.5 Hz), 7.69 (1H, dd, J=7.8, 1.2 Hz). $^{13}$C NMR (101 MHz, CDCl$_3$) δ 3.8, 4.3, 9.6, 17.7, 18.3, 21.8, 23.1, 28.9, 33.6, 35.9, 38.6, 43.8, 44.5, 46.2, 53.5, 53.7, 59.3, 60.3, 73.8, 82.6, 94.8, 116.8, 119.9, 125.7, 127.4, 128.4, 130.6, 130.8, 133.4, 136.1, 137.7, 139.7, 145.4. HMRS: calc for [C$_{32}$H$_{40}$N$_1$O$_4$]$^+$ ([M+H]$^+$) 502.2952, found 502.3045.

(1'R,5α,6R,7R,14α)-1'-(3-methylphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=3-MePh) (BU12005)

$^1$H NMR (400 MHz, CDCl$_3$) δ 0.00-0.08 (2H, m), 0.39-0.50 (2H, m), 0.64-0.74 (1H, m), 0.86-0.96 (1H, m), 1.26-1.35 (4H, m), 1.54-1.58 (2H, m), 1.76-1.87 (2H, m), 1.96 (1H, dd, J=14.3, 4.9 Hz), 2.19-2.30 (5H, m), 2.36 (3H, s), 2.54-2.62 (1H, m), 2.95 (1H, d, J=19.7 Hz), 2.99 (1H, d, J=6.9 Hz), 3.61 (3H, s), 4.75 (1H, bs), 5.00 (2H, s), 5.72 (1H, s), 6.53 (1H, d, J=8.0 Hz), 6.70 (1H, d, J=8.0 Hz), 7.07 (1H, d, J=6.8 Hz), 7.18-7.23 (2H, m), 7.29 (1H, s). $^{13}$C NMR (101 MHz, CDCl$_3$) δ 3.8, 4.4, 9.6, 17.2, 18.2, 21.9, 23.1, 29.7, 33.7, 35.9, 39.8, 43.4, 43.9, 46.2, 53.4, 59.3, 60.3, 80.4, 82.4, 94.8, 116.8, 120.0, 127.5, 127.6, 128.4, 128.5, 131.0, 133.4, 137.2, 137.7, 141.2, 145.4. HMRS: calc for [C$_{32}$H$_{40}$N$_1$O$_4$]$^+$ ([M+H]) 502.2952, found 502.3086.

(1'R,5α,6R,7R,14α)-1'-(4-methylphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=4-MePh) (BU12006)

$^1$H NMR (400 MHz, CDCl$_3$) δ 0.00-0.07 (2H, m), 0.41-0.50 (2H, m), 0.64-0.72 (1H, m), 0.86-0.94 (1H, m), 1.25-1.32 (4H, m), 1.50-1.55 (2H, m), 1.76-1.84 (2H, m), 1.95 (1H, dd, J=14.0, 4.0 Hz), 2.18-2.28 (5H, m), 2.34 (3H, s), 2.55-

2.61 (1H, m), 2.94 (1H, d, J=18.5 Hz), 2.98 (1H, d, J=6.5 Hz), 3.60 (3H, s), 4.97 (1H, s), 5.01 (1H, s), 5.47 (1H, bs), 5.85 (1H, s), 6.50 (1H, d, J=8.0 Hz), 6.66 (1H, d, J=8.0 Hz), 7.12 (2H, d, J=8.0 Hz), 7.33 (2H, d, J=8.0 Hz). $^{13}$C NMR (125 MHz, CDCl$_3$) δ 3.4, 4.0, 9.2, 16.8, 17.8, 21.0, 22.6, 23.8, 29.3, 33.3, 35.5, 39.4, 43.0, 43.5, 45.7, 53.0, 58.9, 60.0, 79.9, 81.9, 94.2, 116.5, 119.5, 127.8, 128.0, 129.9, 132.9, 136.8, 137.5, 137.7, 145.0. HMRS: calc for $[C_{32}H_{40}N_1O_4]^+$ ([M+H]$^+$) 502.2952, found 502.3104; calc for $[C_{32}H_{39}N_1O_4Na_1]^+$ ([M+Na]$^+$) 524.2777, found 524.2812.

(1'R,5α,6R,7R,14α)-1'-(4-fluorophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=4-FPh) (BU12007)

$^1$H NMR (400 MHz, CDCl$_3$) δ 0.00-0.08 (2H, m), 0.40-0.50 (2H, m), 0.64-0.72 (1H, m), 0.87-0.97 (1H, m), 1.23-1.29 (4H, m), 1.46 (1H, d, J=14.5 Hz), 1.51-1.58 (1H, m), 1.73-1.85 (2H, m), 1.95 (1H, dd, J=14.0, 4.0 Hz), 2.19-2.28 (5H, m), 2.54-2.61 (1H, m), 2.94 (1H, d, J=18.5 Hz), 2.99 (1H, d, J=6.5 Hz), 3.59 (3H, s), 4.95 (1H, d, J=2.0 Hz), 5.03 (1H, s), 6.00 (1H, s), 6.49 (1H, d, J=8.5 Hz) 6.62 (1H, d, J=8.0 Hz), 7.00 (2H, t, J=8.8 Hz), 7.42 (2H, dd, J=8.5, 5.5 Hz). $^{13}$C NMR (125 MHz, CDCl$_3$) δ 3.4, 4.0, 9.1, 16.7, 17.7, 22.6, 29.3, 33.3, 35.4, 39.4, 42.9, 43.5, 45.6, 58.8, 59.9, 79.4, 81.9, 93.9, 114.0, 114.2, 116.62, 119.5, 127.6, 131.3, 131.4, 132.8, 137.6, 145.0, 161.1, 163.0. HMRS: calc for $[C_{31}H_{37}N_1O_4F_1]^+$ ([M+H]$^+$) 506.2701, found 506.2682.

(1'R,5α,6R,7R,14α)-1'-(3-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=3-thiophenyl-) (BU12015)

White Solid; $^1$H NMR (CDCl$_3$) δ 0.04-0.06 (2H, m), 0.44-0.49 (2H, m), 0.69-0.73 (1H, m), 0.88-0.93 (1H, m), 1.18-1.21 (1H, m), 1.30 (3H, s), 1.49-1.56 (2H, m), 1.71-1.83 (2H, m), 2.08 (1H, dd, J=14.20 Hz & J=4.04 Hz), 2.16-2.30 (5H, m), 2.58 (1H, d, J=6.72 Hz), 2.93 (1H, d, J=18.40 Hz), 2.98 (1H, d, J=6.36 Hz), 3.60 (3H, s), 4.68 (1H, bd), 4.98 (1H, s), 5.14 (1H, s), 5.64 (1H, s), 6.52 (1H, d, J=8.08 Hz), 6.69 (1H, d, J=8.08 Hz), 7.17-7.19 (1H, m), 7.22-7.25 (2H, m); $^{13}$C NMR, 400 MHz, (CDCl$_3$) δ 3.28, 4.09, 9.21, 16.89, 17.81, 22.66, 29.34, 33.35, 35.54, 40.09, 42.97, 43.56, 45.72, 53.03, 58.79, 59.92, 76.62, 81.78, 94.21, 116.38, 119.58, 123.55, 123.96, 128.06, 128.81, 132.90, 137.26, 142.54, 145.11. HRMS, m/z for (C$_{29}$H$_{35}$NO$_4$SNa) [MNa]$^+$, calcd—516.2184, found—516.2212. Anal. (C$_{29}$H$_{35}$NO$_4$S.HCl) C, H, N.

(1'R,5α,6R,7R,14α)-1'-(3-methyl-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=(3-methyl-2-thiophenyl) (BU12016)

White Solid; $^1$H NMR (CDCl$_3$) δ 0.02-0.04 (2H, m), 0.41-0.46 (2H, m), 0.66-0.72 (1H, m), 0.87-0.97 (1H, m), 1.24-1.28 (2H, m), 1.52 (3H, s), 1.55-1.61 (1H, m), 1.77-1.85 (2H, m), 2.11 (1H, dd, J=14.20 Hz & J=4.04 Hz), 2.21-2.29 (8H, m), 2.59 (1H, m), 2.92-2.96 (2H, m), 3.58 (3H, s), 4.80 (1H, bd), 5.01 (1H, s), 5.45 (2H, s), 6.51 (1H, d, J=8.08 Hz), 6.68 (1H, d, J=8.08 Hz), 6.76 (1H, d, J=5.12 Hz), 7.20 (1H, d, J=5.12 Hz); $^{13}$C NMR, 400 MHz, (CDCl$_3$) δ 3.38, 3.93, 9.18, 15.67, 17.09, 17.94, 22.68, 29.01, 33.33, 35.50, 39.27, 43.43, 44.10, 45.87, 53.08, 58.90, 59.91, 73.50, 81.90, 94.22, 116.40, 119.57, 124.09, 127.99, 128.75, 132.87, 134.55, 137.29, 138.41, 144.92. HRMS, m/z for (C$_{30}$H$_{38}$NO$_4$S) [MH]$^+$, calcd—508.2521, found—508.2571. Anal. (C$_{30}$H$_{37}$NO$_4$S.HCl) C, H, N.

(1'R,5α,6R,7R,14c)-1'-(5-chloro-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=(5-chloro-2-thiophenyl) (BU12018)

White Solid; $^1$H NMR (CDCl$_3$) δ 0.06-0.07 (2H, m), 0.46-0.50 (2H, m), 0.73-0.75 (1H, m), 0.87-0.94 (1H, m), 1.14-1.19 (1H, m), 1.32 (3H, s), 1.44-1.52 (2H, m), 1.65-1.68 (1H, m), 1.77-1.80 (1H, m), 2.23-2.28 (6H, m), 2.61 (1H, d, J=7.08 Hz), 2.93 (1H, d, J=18.40 Hz), 2.98 (1H, d, J=6.36 Hz), 3.57 (3H, s), 4.63 (1H, bd), 4.96 (1H, s), 5.16 (1H, s), 5.87 (1H, s), 6.52 (1H, d, J=8.08 Hz), 6.69 (1H, d, J=8.08 Hz), 6.76 (1H, d, J=3.80 Hz), 6.79 (1H, d, J=3.80 Hz); $^{13}$C NMR, 400 MHz, (CDCl$_3$) δ 3.39, 3.98, 9.25, 16.80, 17.69, 22.85, 29.27, 33.38, 35.58, 40.39, 42.99, 43.45, 45.73, 53.05, 58.82, 59.94, 77.58, 81.67, 94.04, 116.44, 119.67, 124.82, 125.23, 128.05, 129.14, 132.76, 137.25, 144.32, 144.87. HRMS, m/z for (C$_{29}$H$_{34}$NO$_4$SClNa) [MNa]$^+$, calcd—550.1795, found—550.1823. Anal. (C$_{29}$H$_{34}$NO$_4$SCl.HCl) C, H, N.

(1'R,5α,6R,7R,14α)-1'-(2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol (30: R=(2-thiophenyl) (BU12025)

White Solid; $^1$H NMR (CDCl$_3$) δ 0.05-0.06 (2H, m), 0.42-0.51 (2H, m), 0.70-0.75 (1H, m), 0.86-0.95 (1H, m), 1.17-1.21 (2H, m), 1.35 (3H, s), 1.47-1.52 (1H, m), 1.71-1.84 (2H, m), 2.18-2.31 (6H, m), 2.59 (1H, d, J=6.72 Hz), 2.93 (1H, d, J=18.40 Hz), 2.99 (1H, d, J=6.36 Hz), 3.59 (3H, s), 4.68 (1H, bd), 4.98 (1H, s), 5.31 (1H, s), 5.85 (1H, s), 6.52 (1H, d, J=8.08 Hz), 6.69 (1H, d, J=8.08 Hz), 6.95-6.98 (1H, m), 7.03-7.04 (1H, m), 7.24-7.26 (1H, m); $^{13}$C NMR, 400 MHz, (CDCl$_3$) δ 3.34, 4.04, 9.23, 16.77, 17.77, 22.70, 29.28, 33.38, 35.59, 40.39, 43.10, 43.51, 45.74, 53.05, 58.79, 59.92, 76.62, 81.75, 94.15, 116.40, 119.62, 124.66, 125.71, 126.22, 128.08, 132.86, 137.25, 144.90, 145.27. HRMS, m/z for (C$_{29}$H$_{35}$NO$_4$SNa) [MNa]$^+$, calcd—516.2184, found—519.2155. Anal. (C$_{29}$H$_{35}$NO$_4$S.HCl.1.4H$_2$O) C, H, N.

(1'R,5α,6R,7R,14α)-1'-(4-methoxyphenyl)-1'(4,5-epoxy-7,8-dihydro-3-hydroxy-6-methoxy-7δ-methyl 17-cyclopropylmethyl-6,14-ethanomorphinan-7-yl)-methan-1'-ol (30: R=(4-methoxyphenyl) (BU12027)

White Solid; $^1$H NMR (CDCl$_3$) δ 0.02-0.05 (2H, m), 0.42-0.47 (2H, m), 0.64-0.67 (1H, m), 0.91-0.94 (1H, m), 1.23-1.29 (4H, m), 1.48 (1H, d, J=14.10 Hz), 1.51-1.53 (1H, m), 1.78-1.82 (2H, m), 1.91-1.94 (1H, m), 2.20-2.30 (5H, m), 2.56 (1H, d, J=5.88 Hz), 2.93-2.99 (2H, m), 3.59 (3H, s), 3.81 (3H, s), 4.98-5.01 (2H, m), 5.77 (1H, s), 6.50 (1H, d, J=8.00 Hz), 6.68 (1H, d, J=8.00), ), 6.84 (2H, d, J=8.68);, ), 7.34 (2H, d, J=8.68); $^{13}$C NMR. 400 MHz, (CDCl$_3$) δ 3.42, 4.02, 9.18, 16.72, 17.78, 22.60, 29.28, 33.29, 35.47, 39.42, 43.09, 43.46, 45.71, 53.06, 55.20, 58.86, 59.96, 79.55, 81.89, 94.27, 112.70, 116.40, 119.54, 127.94, 130.91, 132.92, 137.33, 144.91, 158.76. HRMS, m/z for ($C_{32}H_{39}NO_5Na$) $[MNa]^+$, calcd—540.2726, found—540.2731.

(1'R,5α,6R,7R,14α)-1'-(4-methoxyphenyl)-1'-(4,5-epoxy-7,8-dihydro-3,6-dimethoxy-7β-methyl 17-cyclopropylmethyl-6,14-ethanomorphinan-7-yl)-methan-1'-ol (28: R=(4-methoxyphenyl)

White Solid; $^1$H NMR (CDCl$_3$) δ 0.01-0.05 (2H, m), 0.42-0.47 (2H, m), 0.66-0.69 (1H, m), 0.91-0.94 (1H, m), 1.23-1.29 (4H, m), 1.47 (1H, d, J=14.10 Hz), 1.53 (1H, d, J=9.88 Hz), 1.79-1.85 (2H, m), 1.91 (1H, dd, J=14.20 Hz & J=3.88 Hz), 2.20-2.30 (5H, m), 2.56 (1H, d, J=5.88 Hz), 2.93 (1H, d, J=19.44 Hz), 2.97 (1H, d, J=7.08 Hz), 3.62 (3H, s), 3.81 (3H, s), 3.90 (3H, s), 4.95 (1H, s), 4.96 (1H, s), 5.75 (1H, s), 6.56 (1H, d, J=8.08 Hz), 6.71 (1H, d, J=8.08), ), 6.84 (2H, d, J=8.68);, ), 7.35 (2H, d, J=8.68); $^{13}$C NMR, 400 MHz, (CDCl$_3$) δ 3.41, 4.05, 9.18, 16.71, 17.80, 22.53, 29.37, 33.38, 35.38, 39.43, 43.02, 43.46, 45.38, 53.09, 55.21, 56.88, 58.84, 59.98, 79.57, 81.80, 93.74, 112.67, 114.14, 119.13, 128.51, 130.92, 133.08, 133.24, 141.75, 146.38, 158.72. HRMS, m/z for ($C_{33}H_{41}NO_5Na$) $[MNa]^+$, calcd—554.2882, found—554.2916.

Receptor Binding and [$^{35}$S]GTPγS Assays

Cell Culture: C6 glioma cells stably expressing the rat MOR (C6μ) or DOR (C6δ) were grown in Dulbecco's modified eagle medium (DMEM) supplemented with 10% fetal bovine serum (FBS), 90 units/ml penicillin, 90 μg/ml streptomycin, and 0.5 mg/ml geneticin. Chinese hamster ovary cells stably expressing the human KOR (CHO$_K$) or human NOP receptor CHO-NOP were maintained similarly, except that DMEM-F12 medium was used. All cells were grown under 5% CO$_2$ at 37° C.

Preparation of Cell Membranes: Cells were washed three times with PBS and detached from plates using harvesting buffer (20 mM HEPES, pH 7.4, 150 mM NaCl, and 0.68 mM EDTA). After centrifugation at 200×g for 3 min, the cell pellet was resuspended in 50 mM Tris-HCl, pH 7.4 and homogenized with a Tissue Tearor (Biospec Products, Inc). The homogenate was pelleted at 20,000×g for 20 min at 4° C. and the pellet resuspended in 50 mM Tris-HCl, pH 7.4 and re-homogenized. The final pellet was resuspended in 50 mM Tris-HCl, pH 7.4 and frozen in aliquots at −80° C. Protein concentration was determined using the BCA protein assay.

Ligand Binding Assays: As Alt et al., 2002. Membranes (20 μg) are incubated in 50 mM Tris-HCl, pH 7.4 with [$^3$H] diprenorphine or [$^3$H]nociceptin in the absence or presence of varying concentrations of test compounds for 60 min in a shaking water bath at 25° C. Nonspecific binding is measured using 10 μM naloxone (MOR, DOR, KOR) or N/OFQ (NOP). Samples are filtered through GF/C glass-fiber filtermats mounted on a Brandel cell harvester and rinsed four times with 4° C. 50 mM Tris-HCl, pH 7.4 buffer. Filtermats are dried and 0.1 ml EcoLume scintillation cocktail added to each sample area to soak the filter. Each filtermat in a heat-sealed bag, is counted in a Wallac 1450 MicroBeta Liquid Scintillation and Luminescence Counter. IC50 values for test compounds are determined from concentration effect curves and converted to $K_i$ values using GraphPad Prism.

[$^{35}$S]GTPγS Binding Assays: As described previously (Traynor and Nahorski, 1995), membranes (20 μg) from cells expressing MOR, DOR, KOR or NOP receptors are incubated in 20 mM Tris-HCl, pH 7.4, 5 mM MgCl$_2$, 100 mM NaCl, 2.2 mM dithiothreitol (prepared freshly), 30 μM GDP, 0.1 nM [$^{35}$S]GTPγS, with or without 10 μM of test compound or 10 μM standard (DAMGO, SNC80, U50488H or N/OFQ as appropriate) or H$_2$O for 60 min at 25° C. Samples are filtered through GF/C glass-fiber filtermats mounted on a Brandel cell harvester and rinsed four times with ice-cold 50 mM Tris-HCl, pH 7.4 containing 5 mM MgCl$_2$, and 100 mM NaCl. Filtermats are processed as described for ligand binding above.

Mouse Warm Water Tail Withdrawal Assay. For all of the tail-withdrawal data a minimum of five mice is used in each group. Each mouse (is placed in a cylindrical restraint (Harvard Apparatus, South Natick, Mass., USA) with the tail fully exposed. Approximately one-third of the tail is immersed in water at 48° C. and latency to tail-withdrawal is measured (Janssen et al, 1963). The low temperature is to ensure that compounds with at delta or kappa agonism can be identified. Standards, test compounds or vehicle (usually sterile water) are be administered i.p. and tail-withdrawal latencies measured 25 min later. For antagonist studies compounds are administered 30 min before the first agonist dose. Baseline latencies vehicle injected mice) are typically 2-4 s. A cut-off latency of 20 s is used to prevent injury to the tail. Mice that do not respond within this time are removed and assigned a score of 20 s.

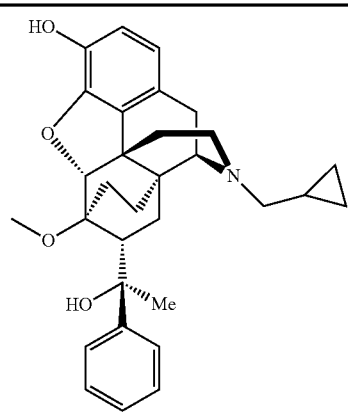

| | Binding affinities (Ki/nm) at opioid and NOP receptors | | | |
|---|---|---|---|---|
| | Mu | Kappa | Delta | NOP |
| 7a, R = Ph-BU127 | 0.71 | 0.49 | 1.91 | 43.2 |

| | Binding affinities (Ki/nm) at opiod and NOP receptors | | | | |
|---|---|---|---|---|---|
| | | Mu | Kappa | Delta | NOP |
| 15a, R = Ph-BU147 | 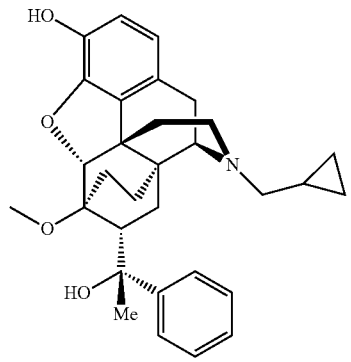 | | | | |
| 13a, R = Ph-BU126 | 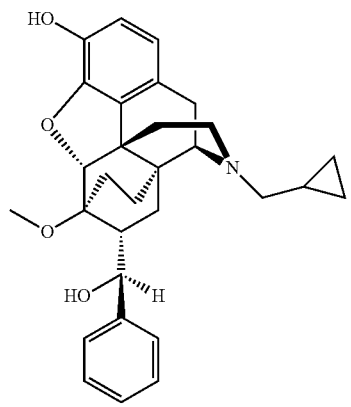 | 1.25 | 4.40 | 2.55 | |
| 10a, R = Ph-BU106 | 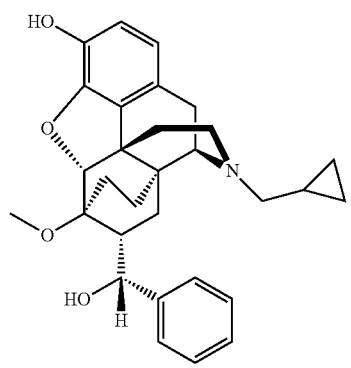 | | | | |
| 22, R = Ph-BU128 | 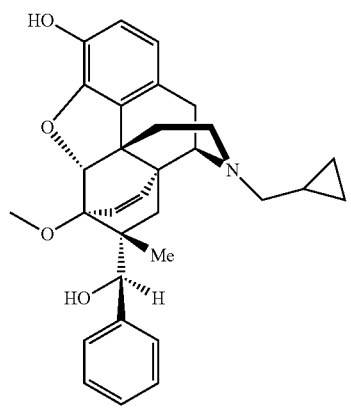 | 0.08 | 0.08 | 0.48 | 97 |

-continued

| Binding affinities (Ki/nm) at opiod and NOP receptors | | | | |
|---|---|---|---|---|
| | Mu | Kappa | Delta | NOP |
| 23, R = Ph-BU129 | 0.60 | 3.02 | 1.08 | |
| 13b, R = Ph-BU125 | 4.03 | 3.84 | 3.21 | |
| 7a, R = 2-thienyl-BU08026 | 0.60 | | | 34.5 |

| Binding affinities (Ki/nm) at opiod and NOP receptors | | | | |
|---|---|---|---|---|
| | Mu | Kappa | Delta | NOP |
7a, R = 4-t-BuPh-
BU08024
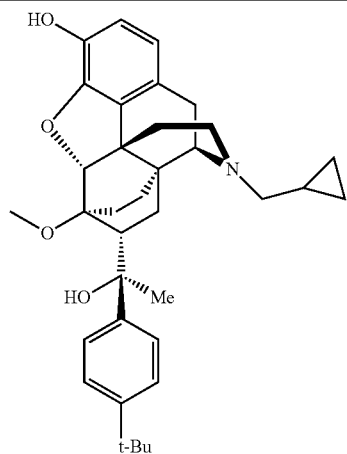
7a, R = m-tolyl-
BU10092
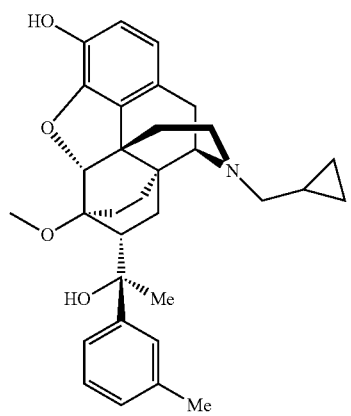
BU10093
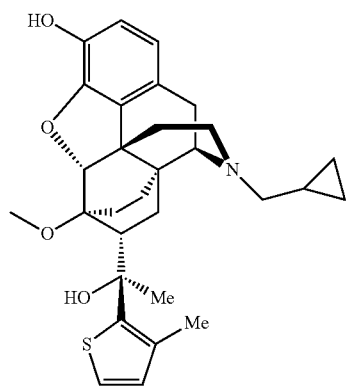

-continued
| | Binding affinities (Ki/nm) at opiod and NOP receptors | | | |
|---|---|---|---|---|
| | Mu | Kappa | Delta | NOP |
7a, R = 4-i-PrPh-
BU10096
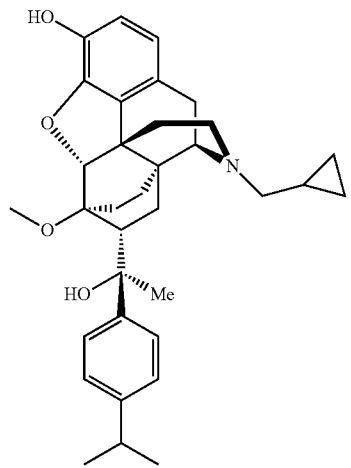
7a, R = 4-ClPh-
BU10097
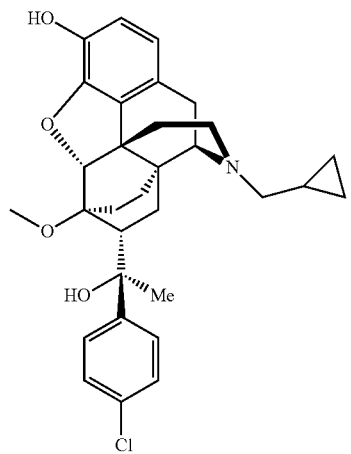
7a, R = 3-ClPh-
BU10098
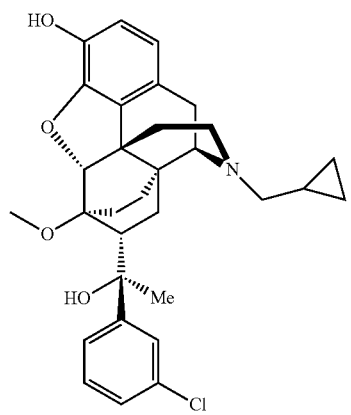

| | Binding affinities (Ki/nm) at opiod and NOP receptors | | | |
|---|---|---|---|---|
| | Mu | Kappa | Delta | NOP |
23, R = 4-MePh-
BU10099
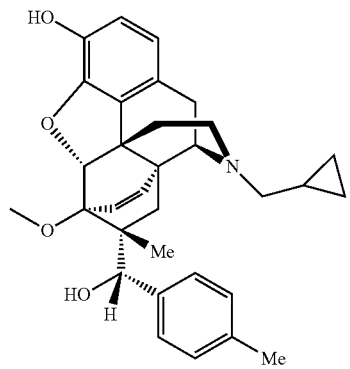
7a, R = 3,5-diMePh-
BU10100
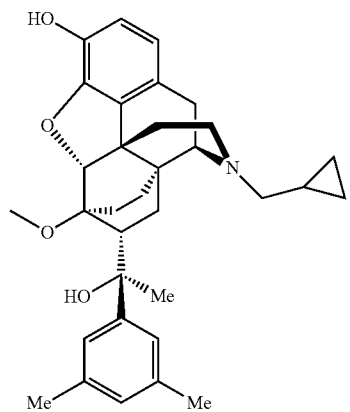
0.28    0.10
7a, 2-MePh-
BU10101
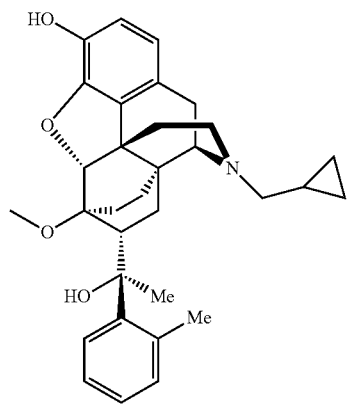
0.19    0.16

-continued
| Binding affinities (Ki/nm) at opiod and NOP receptors | | | | |
|---|---|---|---|---|
| | Mu | Kappa | Delta | NOP |
7a, 4-FPH-BU10102
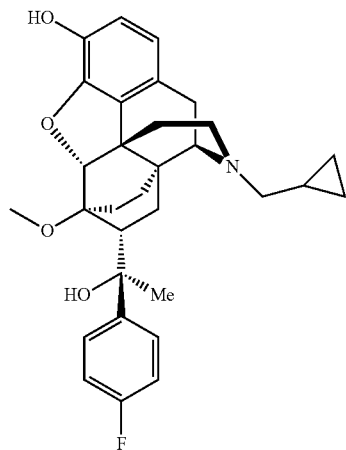
7a, 3-FPH-BU10103
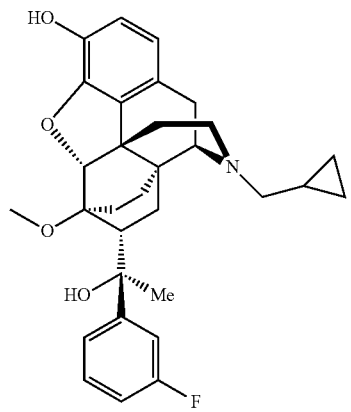
22, R = 2-MePh-BU10111
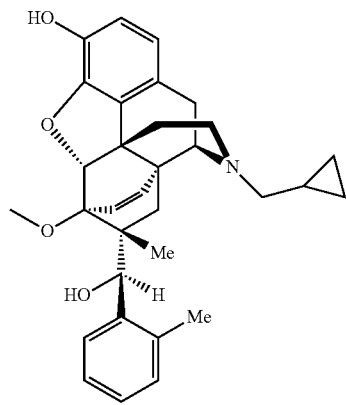

-continued
| | Binding affinities (Ki/nm) at opiod and NOP receptors | | | |
|---|---|---|---|---|
| | Mu | Kappa | Delta | NOP |
| 22, R = 3-MePh-BU10112 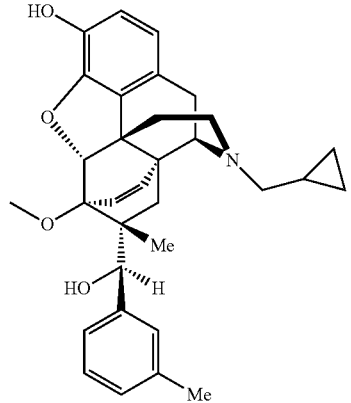 | 0.17 | 0.04 | 0.40 | 79 |
| 23, R = 3-MePh-BU10113 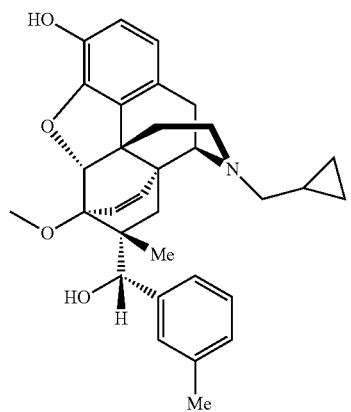 | | | | |
| 22, R = 4-MePh-BU10117 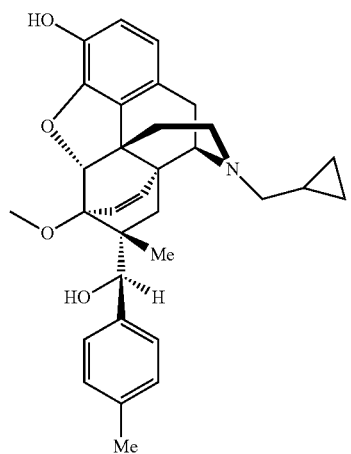 | | | | |

-continued
| | Binding affinities (Ki/nm) at opiod and NOP receptors | | | |
|---|---|---|---|---|
| | Mu | Kappa | Delta | NOP |
| 23, R = 4-FPh-BU10118 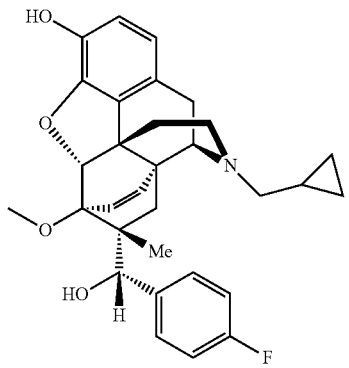 | | | | |
| 30, R = Ph-BU10119 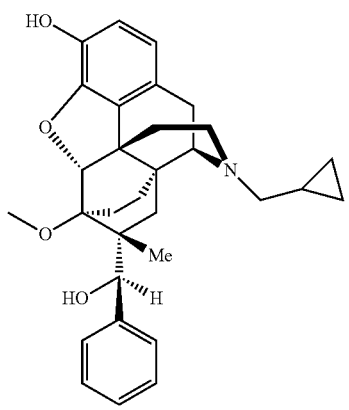 | 0.10 | 0.04 | 0.25 | 80 |
| 22, R = 4-FPh-BU10120 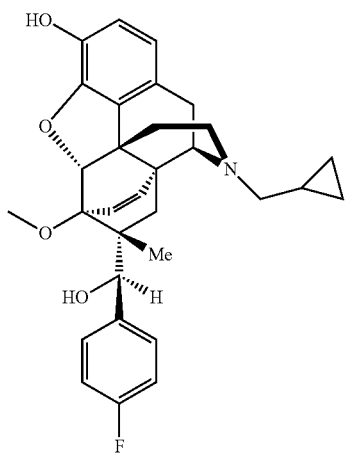 | 0.16 | 0.05 | 0.47 | 34 |

-continued
| Binding affinities (Ki/nm) at opiod and NOP receptors | | | | |
|---|---|---|---|---|
| | Mu | Kappa | Delta | NOP |
23, R = 2-MePh-BU10121
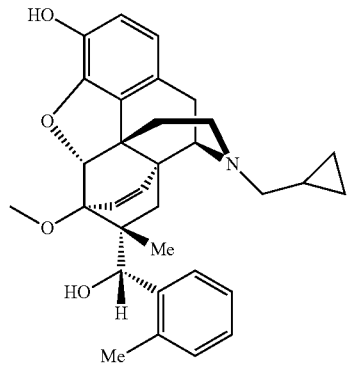
29, R = Ph-BU10122
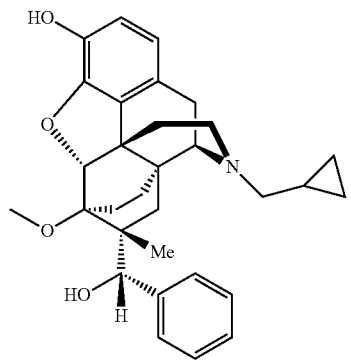
7a, R = 4-MePh-BU10135
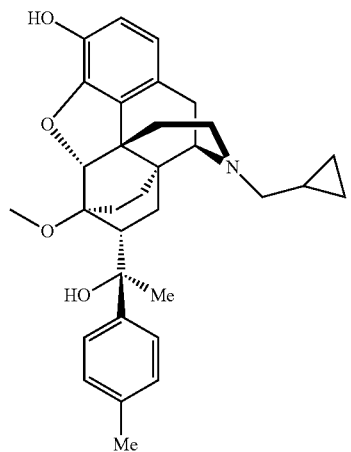

-continued
| Binding affinities (Ki/nm) at opiod and NOP receptors | | | | |
|---|---|---|---|---|
| | Mu | Kappa | Delta | NOP |
7a, (3-Cl)-
2-thiophenyl-
BU10136
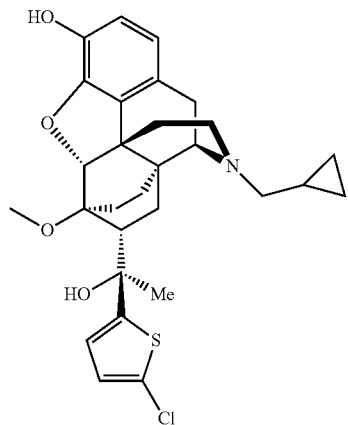
7a, R = 3-
thiophenyl-
BU11001
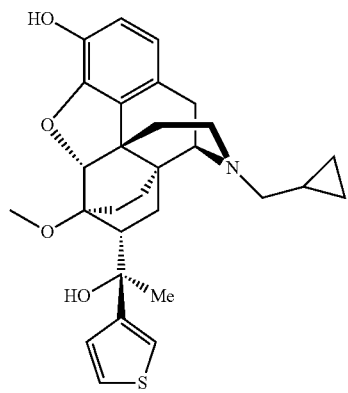
15a, R = 2-pyridyl-
BU11005
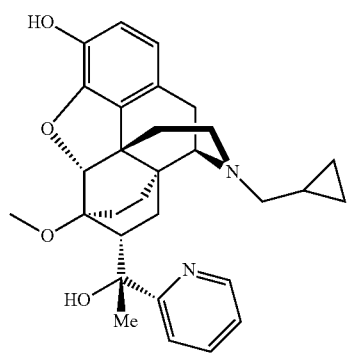
15a, R = 4-pyridyl-
BU11006
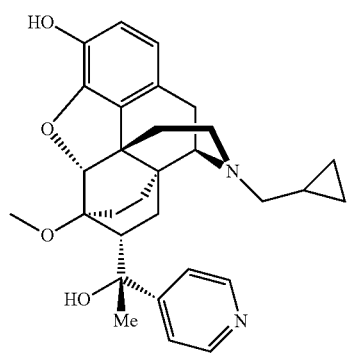

Binding affinities (Ki/nm) at opiod and NOP receptors
| | Mu | Kappa | Delta | NOP |
|---|---|---|---|---|
22, R = 4-PrSPh-
BU11020
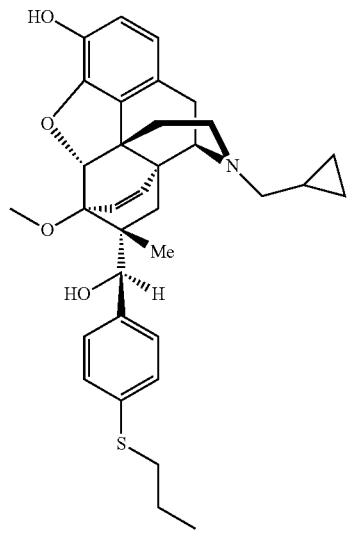
30, R = 2-MePh-
BU12004
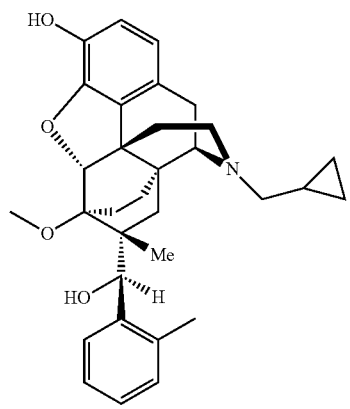
30, 3-MePh-
BU12005
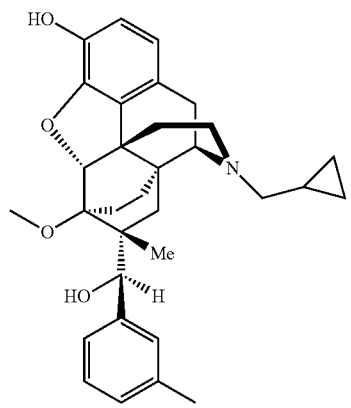

| Binding affinities (Ki/nm) at opiod and NOP receptors | | | | |
|---|---|---|---|---|
| | Mu | Kappa | Delta | NOP |
30, 4-MePh-BU12006
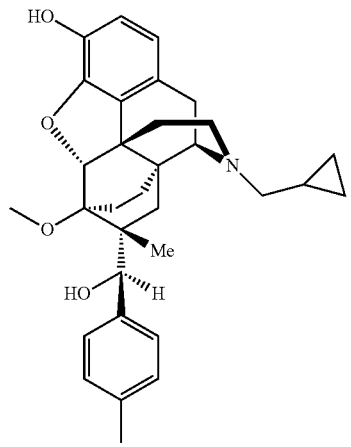
30, 4-FPh-BU12007
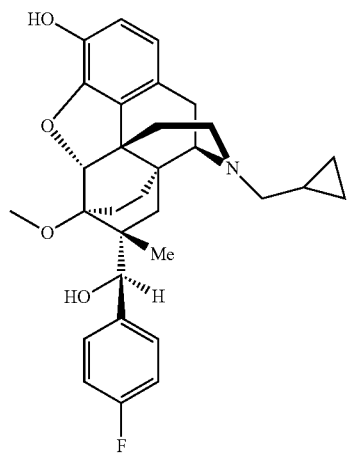
30, R = 3-thiophenyl-BU12015
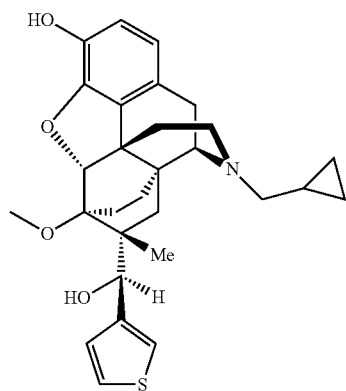

| Binding affinities (Ki/nm) at opiod and NOP receptors | | | | |
|---|---|---|---|---|
| | Mu | Kappa | Delta | NOP |
30, R = (3-Me)-2-thiophenyl-BU12016
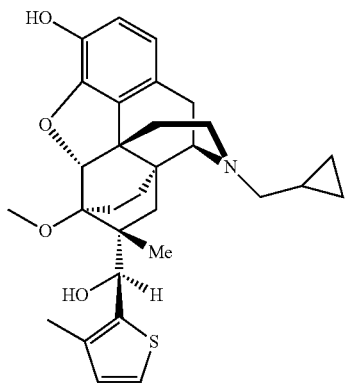
30, R = 3-Cl-2-thiophenyl-BU12018
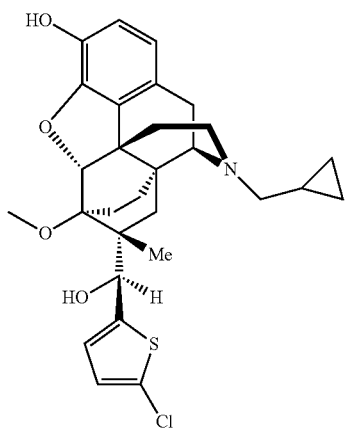
30, R = 2-thiophenyl-BU12025
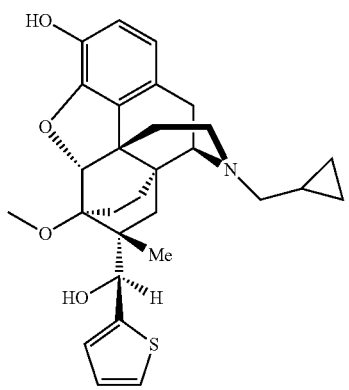

| Binding affinities (Ki/nm) at opiod and NOP receptors | | | | |
|---|---|---|---|---|
| | Mu | Kappa | Delta | NOP |
| 30, R = 4-MeOPh-BU12027 | | | | |
| 28, R = 4-MeOPh | | | | |

Binding affinities at MOPr, KOPr, DOPr and NOPr were measured using [$^3$H]diprenorphine (MOP, KOP, DOP) and [$^3$H]N/OFQ (NOP) binding to membranes derived from CHO cells transfected with human receptors (KOP and NOP receptors) and C6 glioma cells stably expressing rat receptors (MOP and DOP). All compounds tested have high affinity at opioid receptors and selected compounds display affinity at NOP receptors.

TABLE 2

Efficacy (% stimulation$^a$) and/or antagonist potency (Ke/nM) at mu, kappa and NOP receptors

| | Mu | | Kappa | | NOP |
|---|---|---|---|---|---|
| | % stim$^a$ | Ke/nM | % stim$^a$ | Ke/nM | % stim$^a$ |
| 7a, R = Ph | — | 0.47 | — | 0.27 | 14 |
| 22, R = Ph | 4 | 0.47 | 3 | 0.41 | 39 |
| 22, R = 3-MePh | 22 | — | 6 | — | 43 |
| 30, R = Ph | 2 | 0.28 | 0 | 0.09 | 57 |
| 15a, R = 4-pyridyl | 1 | — | −17 | — | 4 |
| 30, 3-MePh | 9 | — | −1 | — | 21 |
| 30, 4-FPh | 17 | — | −5 | — | 13 |

$^a$% stimulation at a single concentration (10 μM) versus the standards DAMGO (MOP), U69,593 (KOP) and nociceptin (NOP)

In a measure of functional activity, selected compounds have been evaluated in the [$^{35}$S]GTPγS assay in the same cell lines used for the binding assays (Table 2). Assays were performed as previously described by Traynor and Nahorski.[21] Agonist efficacy at MOR, KOR and NOP receptors was determined at a single concentration (10 μM) in comparison to the standard selective agonists DAMGO (MOR), and U69593 (KOR) and nociceptin (NOP) and antagonist Ke values determined against these standard agonists. For example, both 22, R=Ph (Ke$_{(MOR)}$ 0.47 nM, Ke$_{(KOR)}$ 0.41 nM) and 7a, R=Ph (Ke$_{(MOR)}$ 0.47 nM, Ke$_{(KOR)}$ 0.27 nM) are antagonists at MOR and KOR and have partial agonist activity at NOP receptors (40% and 14% of nociceptin's efficacy). 30, R=Ph also has no efficacy at MOR and KOR and is a partial agonist (57% of nociceptin) at NOP receptors.

Furthermore, it has been confirmed that 7a, R=Ph, 22, R=Ph and 30, R=Ph display no opioid agonist actions in vivo, in assays where even a low efficacy opioid agonist would be expected to be active. Thus they display no agonist activity in the anti-writhing assay (abdominal stretch assay) or in the 50° C. tail withdrawal assay.

REFERENCES

Alt, A., Clark, M., Woods, J. H., and Traynor, J. R. Brit J Pharmacol. 2002, 135, 217-225

Auriacombe, M.; Fatseas, M.; Dubemet, J.; Daulouede, J. P.; Trignol, J. French field experience with buprenorphine. Am. J. Addict., 2004, 13, Suppl 1. S17-28.

Beardsley, P. M.; Howard, J. L., Shelton, K. L. & Carroll, F. I. Differential effects of the novel kappa opioid receptor antagonist, JDTic, on reinstatement of cocaine-seeking induced by footshock stressors vs cocaine primes and its antidepressant-like effects in rats. Psychopharmacology (Berl.) 2005, 183, 118-126.

Bloms-Funke P, Gillen C, Schuettler A J and Wnendt S. Agonistic effects of the opioid buprenorphine on the nociceptin/OFQ receptor. Peptides 2000, 21, 1141-1146.

Ciccocioppo R, Economidou D, Rimondini R, Sommer W, Massi M and Heilig M. Buprenorphine Reduces Alcohol Drinking Through Activation of the Nociceptin/Orphanin FQ-NOP Receptor System. Biol Psychiatry. 2007, 61, 4-12.

Comer, S. D.; Sullivan, M. A.; Yu, E.; Rothenberg, J. L.; Kleber, H. D.; Kampman, K.; Dackis, C.; O'Brien, C. P. Injectable, sustained release naltrexone for the treatment of opioid dependence: a randomized, placebocontrolled trial. Archives of General Psychiatry, 2006, 63, 210-218.

Corkery, J. M.; Schifano, F.; Ghodse, A. H.; Oyefeso, A. The effects of methadone and its role in fatalities. Hum. Psychopharmacol., 2004, 19, 565-576.

Cowan A, Lewis J W and Macfarlane I R. Agonist and antagonist properties of buprenorphine, a new antinociceptive agent. Br J Pharmacol. 1977b, 60, 537-545.

Cowan A.; Doxey J. C.; Harry E. J. The animal pharmacology of buprenorphine, an oripavine analgesic agent. Br J Pharmacol., 1977a, 60, 547-554.

Cowan, A. Update on the general pharmacology of buprenorphine. In 'Buprenorphine: Combating drug abuse with a unique opioid. Eds. Cowan and Lewis, Wiley-Liss, New York, 1995, 31-47.

Cowan, A.; Friderichs, E.; Strasburger, W.; Raffa, R. B. Basic pharmacology of buprenorphine, in "Buprenorphine—the unique opioid analgesic" ed.s. Budd. K.; Raffa, R., Thieme, New York, 2005.

DAWN—Drug Abuse Warning Network. 2003: Area Profiles of Drug-Related Mortality, DAWN Series D-27, DHHS Publication No. (SMA) 05-4023, Rockville, Md., March 2005.

Gerra, G., Fantoma, A. & Zaimovic, A. Naltrexone and buprenorphino combination in the treatment of opioid dependence. J. Psychopharmacol. 2006, 20, 806-814.

Gonzalez G, Oliveto A, Kosten T R. Combating opiate dependence: a comparison among the available pharmacological options. Expert Opinion On Pharmacotherapy, 2004, 5, 713-725.

Gorelick, D. A. Regarding "Buprenorphine reduces alcohol drinking through activation of the nociceptin/orphanin FQ-NOP receptor system". Biol. Psychiatry 2007, 62, 702.

Huang, P.; Kehner, G. B.; Cowan, A.; Liu-Chen, L-Y. Comparison of pharmacological activities of buprenorphine and norbuprenorphine; norbuprenorphine is a potent opioid agonist. J. Pharmacol. Exp. Ther., 2001, 297, 688-695.

Knoll, A. T.; Meloni, E. G.; Thomas, J. B.; Carroll, F. I.; Carlezon Jr, W. A. Anxiolytic-like effects of kappa-opioid receptor anagonists in models of unlearned and learned fear in rats. J. Pharmacol. Exp. Ther., 2007, 323, 838-845.

Kosten, T. R., Kleber, H. D. & Morgan, C. Treatment of cocaine abuse with buprenorphine. Biol. Psychiatry 1989, 26, 637-639.

Kotlinska, J., Wichmann, J., Legowska, A., Rolka, K. & Silberring, J. Orphanin FQ/nociceptin but not Ro 65-6570 inhibits the expression of cocaine-induced conditioned place preference. Behav. Pharmacol. 2002, 13, 229-235.

Kovacs, K. M.; Szakall I.; O'Brien D.; Wang R.; Vinod K. Y.; Saito M.; Simonin F.;

Kieffer B. L.; Vadasz C.; Decreased oral self administration of alcohol in KOR knockout mice. Alcohol Clin. Exp. Res., 2005, 29, 730-738.

Lewis, J. W. Ring C-bridged derivatives of thebaine and oripavine. Adv. Biochem. Psychopharmacol., 1973, 8, 123-36

Lewis, J. W.; Bentley, K. W.; Cowan, A. Narcotic analgesics and antagonists. *Ann. Rev. Pharmacol.,* 1971, 11, 241-270.

Lewis, J. W.; Husbands, S. M. The Orvinols and Related Opioids—High Affinity Ligands with Diverse Efficacy Profiles. *Current Pharmaceutical Design*, 2004, 10, 717-732.

Lobmaier, P.; Komor, H.; Kunoe, N.; Bjomdal, A. Sustained-release naltrexone for opioid dependence (Cochrane review). The Cochrane Library, 2008, Issue 3, pp 1-58.

Lutfy K, Eitan S, Bryant C D, Yang Y C, Saliminejad N, Walwyn W, Kieffer B L, Takeshima H, Carroll F I, Maidment N T and Evans C J. Buprenorphine-induced antinociception is mediated by mu-opioid receptors and compromised by concomitant activation of opioid receptor-like receptors. J Neurosci 2003, 23:10331-10337.

Mague, S. D.; Pliakas, A. M.; Todtenkopf, M. S.; Tomasiewicz, H. C.; Zhang, Y.; Stevens, W. C.; Jones, R. M.; Portoghese, P. S.: Carlezon, W. A. Antidepressant-like effects of kappa-opioid receptor antagonists in the forced swim test in rats. J. Pharmacol. Exp. Ther., 2003, 305, 323-330.

Marquez, P.; Nguyen, A. T.; Hamid, A.; Lutfy, K. The endogenous OFQ/N/ORL-1 receptor system regulates the rewarding effects of acute cocaine. Neuropharmacology, 2008, 54, 564-568.

Marton, J.; Simon, C.; Hosztafi, S.; Szabó, Z.; Márki, Á.; Borsodi, A.; Makleit, S. New nepenthone and thevinone derivatives. Bloorg. Med. Chem., 1997, 369-382

McAleer, S. D.; Mills, R. J.; Polack, T.; Hussain, T.; Rolan, P. E.; Gibbs, A. D.; Mullins, F. G. P.; Hussein, Z. Pharmacokinetics of high dose buprenorphine following single administration of sublingual tablet formulations in opioid naive healthy male volunteers under a naltrexone block. Drug and Alcohol Dependence, 2003, 72, 75-83.

McCann, D. J. Potential of buprenorphine/naltrexone in treating polydrug addiction and co-occurring psychiatric disorders. Clinical Pharmacology & Therapeutics. 2008, 83, 627-630.

McLaughlin, J. P., Marton-Popovici M. & Chavkin C. Kappa opioid receptor antagonism and prodynorphin gene disruption block stress-induced behavioral responses. J. Neurosci. 2003, 23, 5674-5683.

Mello, N. K., Mendelson, J. H. Buprenorphine treatment of cocaine and heroin abuse. in 'Buprenorphine: Combatting drug abuse with a unique opioid.' eds Lewis and Cowan, New York, N. Y., US: Wiley-Liss, 1995, 241-287.

Mello, N. K., Mendelson, J. H., Bree, M. P. & Lukas, S. E. Buprenorphine suppresses cocaine self-administration by rhesus monkeys. Science 1989, 245, 859-862.

Minozzi, S.; Amato, L.; Vecchi, S.; Davoli, M.; Kirchmayer, U.; Verster, A. Oral naltrexone maintenance treatment for opioid dependence (Cochrane review). The Cochrane Library. 2006, Issue 1, ppl-27.

Montoya, I. D.; Gorelick, D. A.; Preston, K. L.; Schroeder, J. R.; Umbricht, A.; Cheskin, L. J.; Lange, W. R.; Contoreggi, C.; Johnson, R. E.; Fudala, P. J. Randomized trial of buprenorphine for treatment of concurrent opiate and cocaine dependence. Clin. Pharmacol. Ther., 2004, 75, 34-48.

Negus, S. S.; Woods, J. H. Reinforcing effects, discriminative stimulus effects and physical dependence liability of buprenorphine, in "Buprenorphine—combating drug abuse with a unique opioid" ed.s. Cowan, A and Lewis, J. W. Wiley-Liss, New York, 1995, p 71-101.

Redila. V. A.; Chavkin, C. Stress-induced reinstatement of cocaine seeking is mediated by the kappa opioid system. Psychopharmacology, 2008, 200, 59-70.

Rothman, R. B. A review of the role of anti-opioid peptides in morphine tolerance and dependence. Synapse, 1992, 12, 129-138.

Rothman, R. B. Gorelick, D. A.; Heishman, S. J.; Eichmiller, P. R.; Hill, B. H.; Norbeck, J.; Liberto, J. G. I. An openlabel study of a functional opioid kappa antagonist in the treatment of opioid dependence. J. Subst. Abuse Treat. 2000, 18, 277-281.

Rothman, R. B.; Long, J. B.; Bykov, V.; Xu, H.; Jacobson. A. E.; Rice, K. C.; Holaday, J. W. Upregulation of the opioid receptor complex by the chronic administration of morphine: A biochemical marker related to the development of tolerance and dependence. Peptides, 1991, 12, 151-160.

Rothman, R. B. Gorelick, D. A.; Heishman, S. J.; Eichmiller, P. R.; Hill, B. H.; Norbeck, J.; Liberto, J. G. I. An openlabel study of a functional opioid kappa antagonist in the treatment of opioid dependence. J. Subst. Abuse Treat. 2000, 18, 277-281.

Schottenfeld, R. S., Pakes, J., Ziedonis, D. & Kosten, T. R. Buprenorphine: dose-related effects on cocaine and opioid use in cocaine-abusing opioid-dependent humans. Biol. Psychiatry 1993, 34, 66-74.

Shoblock, J. R.; Wichmann, J.; Maidment, N. T. The effect of a systemically active ORL-1 agonist, Ro64-6198, on the acquisition, expression, extinction and reinstatement of morphine conditioned place preference. Neuropharmacology, 2005, 49, 439-446.

Shoblock, J. R. The pharmacology of Ro-64-6198, a systemically active, nonpeptide NOP receptor (opiate receptor-like 1, ORL-1) agonist with diverse preclinical therapeutic activity. CNS Drug Reviews, 2007, 13, 107-136.

Spagnolo, B.; Calo, G.; Polgar. W. E.; Jiang, F.; Olsen, C. M.; Berzatei-Gurske, I.; Khroyan, T. V.; Husbands, S. M.; Lewis, J. W.; Toll, L.; Zaveri, N. T. Activities of mixed NOP and; □-opioid receptor ligands. Br, J. Pharmacol., 2008, 153, 609-619.

Srisurapanont, M.; Jarusuraisin, N. Opioid antagonists for alcohol dependence (Cochrane review), The Cochrane Library, 2008, issue 3, pp 1-92.

Traynor, J. R., and Nahorski, S. R. Modulation by mu-opioid agonists of guanosine-5'-O-(3-[35S]thio)triphosphate binding to membranes from human neuroblastoma SH-SY5Y cells. Mol. Pharmacol. 1995, 47, 848-854.

Walker, B. M.; Koob, G. F. Pharmacological evidence for a motivational role of kappa-opioid systems in ethanol dependence, Neuropsychopharmacology, 2008, 33, 643-652.

Wnendt S, Kruger T, Janocha E, Hildebrandt D and Englberger W. Agonistic effect of buprenorphine in a nociceptin/OFQ receptor-triggered reporter gene assay. Mol Pharmacol 1999, 56, 334-338.

Zaveri N, Polgar W E, Olsen C M, Kelson A B, Grundt P, Lewis J W and Toll L. Characterization of opiates, neuroleptics, and synthetic analogs at ORL1 and opioid receptors. Eur J Pharmacol 2001, 428, 29-36.

Zhao, R-J.; Woo, R-S.; Jeong, M-S.; Shin, B-S.; Kim, D-G.; Kim, K-W. Orphanin FQ/nociceptin blocks methamphetamine place preference in rats. Molecular Neuroscience, 2003, 14, 2383-2385.

The invention claimed is:

1. A method of treating depression in a subject, the method comprising administering to said subject an effective amount of a compound of formula 2:

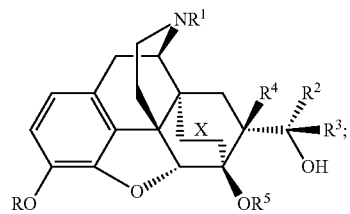

wherein:
R is H or alkyl;
$R^1$ is cyclopropylmethyl;
$R^2$ is H;
$R^4$ and $R^5$ are each methyl;
$R^3$ is aryl or heteroaryl, either of which may be substituted or unsubstituted; and
X is —CH$_2$CH$_2$— or —CH═CH—,
or a pharmaceutically acceptable salt or solvate thereof.

2. The method according to claim 1, wherein X is —CH$_2$CH$_2$—.

3. The method according to claim 1, wherein $R^3$ is substituted phenyl.

4. The method according to claim 1, wherein $R^3$ is phenyl and X is —CH═CH—.

5. The method according to claim 1, wherein $R^3$ is phenyl and X is —CH$_2$CH$_2$—.

6. The method according to claim 1, wherein $R^3$ is m-tolyl and X is —CH═CH—.

7. The method according to claim 1, wherein $R^3$ is 4-fluorophenyl and X is —CH═CH—.

8. The method according to claim 1, wherein the compound of formula 2 is selected from the group consisting of:
(1'R, 5α, 6R, 7R, 14α)-1'-(2-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol; and
(1'R, 5α, 6R, 7R, 14α)-1'-(5-chloro-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol,
or a pharmaceutically acceptable salt or solvate thereof.

9. A method of treating depression in a subject, the method comprising administering to said subject an effective amount of a compound selected from the group consisting of:
(1'S, 5α, 6R, 7R, 14α)-1'-(2-thienyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3-methylphenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(4"-t-butylphenyl)-1'-(4,5-epoxy-7,8-dihydro-3-hydroxy-6-methoxy-17-cyclopropylmethyl-6,14-ethanomorphinan-7-yl)-ethan-1'-ol;

(1'S, 5α, 6R, 7R, 14α)-1'-(4-isopropylphenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(4-chlorophenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3-chlorophenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3,5-dimethylphenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(2-methylphenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(4-fluorophenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3-fluorophenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3-methyl-2-thienyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(4-methylphenyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(5-chloro-2-thienyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-(3-thienyl)-1'-(4,5-epoxy-7,8-dihydro-3-hydroxy-6-methoxy-17-cyclopropylmethyl-6,14-ethanomorphinan-7-yl)-ethan-1'-ol;
(1'R, 5α, 6R, 7R, 14α)-1'-phenyl-1'-(4,5-epoxy-7,8-dihydro-3-hydroxy-6-methoxy-17-cyclopropylmethyl-6,14-ethanomorphinan-7-yl)-ethan-1'-ol;
(1'R, 5α, 6R, 7R, 14α)-1'-(2-pyridyl)-1'-(4,5-epoxy-7,8-dihydro-3-hydroxy-6-methoxy-17-cyclopropylmethyl-6,14-ethanomorphinan-7-yl)-ethan-1'-ol;
(1'R, 5α, 6R, 7R, 14α)-1'-(4-pyridyl)-1'-(4,5-epoxy-7,8-dihydro-3-hydroxy-6-methoxy-17-cyclopropylmethyl-6,14-ethanomorphinan-7-yl)-ethan-1'-ol;
(1'S, 5α, 6R, 7R, 14α)-1'-phenyl-1'-(4,5-epoxy-7,8-dihydro-3-hydroxy-6-methoxy-17-cyclopropylmethyl-6,14-ethanomorphinan-7-yl)-methan-1'-ol;
(1'S, 5α, 6R, 7R, 14α)-1'-phenyl-1'-(4,5-epoxy-7,8-dihydro-3-hydroxy-6-methoxy-17-cyclopropylmethyl-6,14-ethenomorphinan-7-yl)-methan-1'-ol;
(1'R, 5α, 6R, 7R, 14α)-1'-phenyl-1'-(4,5-epoxy-7,8-dihydro-3-hydroxy-6-methoxy-17-cyclopropylmethyl-6,14-ethanomorphinan-7-yl)-methan-1'-ol;
(1'R, 5α, 6R, 7R, 14α)-1'-phenyl-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'S, 5α, 6R, 7R, 14α)-1'-phenyl-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(2-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'S, 5α, 6R, 7R, 14α)-1'-(2-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'R, 5α, 6R, 7R, 14α)-1'-(3-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'S, 5α, 6R, 7R, 14α)-1'-(3-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'R, 5α, 6R, 7R, 14α)-1'-(4-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'S, 5α, 6R, 7R, 14α)-1'-(4-methylphenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'R, 5α, 6R, 7R, 14α)-1'-(4-fluorophenyl)-1'-(4,5-epoxy-7,8-dihydro-3-hydroxy-6-methoxy-7-methyl 17-cyclopropylmethyl-6,14-ethanomorphinan-7-yl)-methan-1'-ol;
(1'S, 5α, 6R, 7R, 14α)-1'-(4-fluorophenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'R, 5α, 6R, 7R, 14α)-1'-(4-propylthiophenyl)-1'-(4,5-epoxy-7,8-dihydro-3-hydroxy-6-methoxy-7β-methyl 17-cyclopropylmethyl-6,14-ethenomorphinan-7-yl)-methan-1'-ol;
(1'S, 5α, 6R, 7R, 14α)-1'-phenyl-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-phenyl-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(2-methylphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(3-methylphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(4-methylphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(4-fluorophenyl)-1'-(4,5-epoxy-7,8-dihydro-3-hydroxy-6-methoxy-7-methyl 17-cyclopropylmethyl-6,14-ethanomorphinan-7-yl)-methan-1'-ol;
(1'R, 5α, 6R, 7R, 14α)-1'-(3-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(3-methyl-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(5-chloro-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;
(1'R, 5α, 6R, 7R, 14α)-1'-(2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol; and (1′R, 5α, 6R, 7R, 14α)-1′-(4-methoxyphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol, or a pharmaceutically acceptable salt or solvate thereof.

10. The method according to claim 9, wherein the compound is selected from the group consisting of:

(1′S, 5α, 6R, 7R, 14α)-1′-phenyl-1′-(4,5-epoxy-7,8-dihydro-3-hydroxy-6-methoxy-17-cyclopropylmethyl-6,14-ethenomorphinan-7-yl)-methan-1′-ol;

(1′R, 5α, 6R, 7R, 14α)-1′-phenyl-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′S, 5α, 6R, 7R, 14α)-1′-phenyl-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′R, 5α, 6R, 7R, 14α)-1′-(2-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′S, 5α, 6R, 7R, 14α)-1′-(2-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′R, 5α, 6R, 7R, 14α)-1′-(3-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′S, 5α, 6R, 7R, 14α)-1′-(3-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′R, 5α, 6R, 7R, 14α)-1′-(4-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′S, 5α, 6R, 7R, 14α)-1′-(4-methylphenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′R, 5α, 6R, 7R, 14α)-1′-(4-fluorophenyl)-1′-(4,5-epoxy-7,8-dihydro-3-hydroxy-6-methoxy-7β-methyl 17-cyclopropylmethyl-6,14-ethenomorphinan-7-yl)-methan-1′-ol;

(1′S, 5α, 6R, 7R, 14α)-1′-(4-fluorophenyl)-1′-(4,5-epoxy-7,8-dihydro-3-hydroxy-6-methoxy-7β-methyl 17-cyclopropylmethyl-6,14-ethenomorphinan-7-yl)-methan-1′-ol; and (1′R, 5α, 6R, 7R, 14α)-1′-(4-propylthiophenyl)-1′-(4,5-epoxy-7,8-dihydro-3-hydroxy-6-methoxy-7β-methyl 17-cyclopropylmethyl-6,14-ethenomorphinan-7-yl)-methan-1′-ol, or a pharmaceutically acceptable salt or solvate thereof.

11. The method according to claim 9, wherein the compound is selected from the group consisting of:

(1′S, 5α, 6R, 7R, 14α)-1′-(2-thienyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3-methylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(4″-t-butylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(4-isopropylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(4-chlorophenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3-chlorophenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3,5-dimethylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(2-methylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(4-fluorophenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3-fluorophenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3-methyl-2-thienyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(4-methylphenyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(5-chloro-2-thienyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-(3-thienyl)-1′-(4,5-epoxy-7,8-dihydro-3-hydroxy-6-methoxy-17-cyclopropylmethyl-6,14-ethanomorphinan-7-yl)-ethan-1′-ol;

(1′R, 5α, 6R, 7R, 14α)-1′-phenyl-1′-(4,5-epoxy-7,8-dihydro-3-hydroxy-6-methoxy-17-cyclopropylmethyl-6,14-ethanomorphinan-7-yl)-ethan-1′-ol;

(1′R, 5α, 6R, 7R, 14α)-1′-(2-pyridyl)-1′-(4,5-epoxy-7,8-dihydro-3-hydroxy-6-methoxy-17-cyclopropylmethyl-6,14-ethanomorphinan-7-yl)-ethan-1′-ol;

(1′R, 5α, 6R, 7R, 14α)-1′-(4-pyridyl)-1′-(4,5-epoxy-7,8-dihydro-3-hydroxy-6-methoxy-17-cyclopropylmethyl-6,14-ethanomorphinan-7-yl)-ethan-1′-ol;

(1′S, 5α, 6R, 7R, 14α)-1′-phenyl-1′-(4,5-epoxy-7,8-dihydro-3-hydroxy-6-methoxy-17-cyclopropylmethyl-6,14-ethanomorphinan-7-yl)-methan-1′-ol;

(1′R, 5α, 6R, 7R, 14α)-1′-phenyl-1′-(4,5-epoxy-7,8-dihydro-3-hydroxy-6-methoxy-17-cyclopropylmethyl-6,14-ethanomorphinan-7-yl)-methan-1′-ol;

(1′S, 5α, 6R, 7R, 14α)-1′-phenyl-1′-(4,5-epoxy-7,8-dihydro-3-hydroxy-6-methoxy-7β-methyl 17-cyclopropylmethyl-6,14-ethanomorphinan-7-yl)-methan-1′-ol;

(1′R, 5α, 6R, 7R, 14α)-1′-phenyl-1′-(4,5-epoxy-7,8-dihydro-3-hydroxy-6-methoxy-7β-methyl 17-cyclopropylmethyl-6,14-ethanomorphinan-7-yl)-methan-1′-ol;

(1′R, 5α, 6R, 7R, 14α)-1′-(2-methylphenyl)-1′-(4,5-epoxy-7,8-dihydro-3-hydroxy-6-methoxy-7β-methyl 17-cyclopropylmethyl-6,14-ethanomorphinan-7-yl)-methan-1′-ol;

(1′R, 5α, 6R, 7R, 14α)-1′-(3-methylphenyl)-1′-(4,5-epoxy-7,8-dihydro-3-hydroxy-6-methoxy-7β-methyl 17-cyclopropylmethyl-6,14-ethanomorphinan-7-yl)-methan-1′-ol;

(1′R, 5α, 6R, 7R, 14α)-1′-(4-methylphenyl)-1′-(4,5-epoxy-7,8-dihydro-3-hydroxy-6-methoxy-7β-methyl 17-cyclopropylmethyl-6,14-ethanomorphinan-7-yl)-methan-1′-ol;

(1′R, 5α, 6R, 7R, 14α)-1′-(4-fluorophenyl)-1′-(4,5-epoxy-7,8-dihydro-3-hydroxy-6-methoxy-7β-methyl 17-cyclopropylmethyl-6,14-ethanomorphinan-7-yl)-methan-1′-ol;

(1'R, 5α, 6R, 7R, 14α)-1'-(3-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;

(1'R, 5α, 6R, 7R, 14α)-1'-(3-methyl-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;

(1'R, 5α, 6R, 7R, 14α)-1'-(5-chloro-2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol;

(1'R, 5α, 6R, 7R, 14α)-1'-(2-thiophenyl)-1'-(4,5-epoxy-7,8-dihydro-3-hydroxy-6-methoxy-7β-methyl 17-cyclopropylmethyl-6,14-ethanomorphinan-7-yl)-methan-1'-ol; and (1'R, 5α, 6R, 7R, 14α)-1'-(4-methoxyphenyl)-1'-(4,5-epoxy-7,8-dihydro-3-hydroxy-6-methoxy-7β-methyl 17-cyclopropylmethyl-6,14-ethanomorphinan-7-yl)-methan-1'-ol, or a pharmaceutically acceptable salt or solvate thereof.

* * * * *